US010344341B2

(12) United States Patent
Carrick et al.

(10) Patent No.: US 10,344,341 B2
(45) Date of Patent: *Jul. 9, 2019

(54) METHOD FOR DETECTING CHIKUNGUNYA VIRUS

(71) Applicant: GEN-PROBE INCORPORATED, San Diego, CA (US)

(72) Inventors: James M. Carrick, Lanham, MD (US); Jeffrey M. Linnen, Poway, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 303 days.

This patent is subject to a terminal disclaimer.

(21) Appl. No.: 15/054,313

(22) Filed: Feb. 26, 2016

(65) Prior Publication Data

US 2016/0168651 A1    Jun. 16, 2016

Related U.S. Application Data

(63) Continuation of application No. 12/386,832, filed on Apr. 21, 2009, now Pat. No. 9,273,365.

(60) Provisional application No. 61/046,734, filed on Apr. 21, 2008.

(51) Int. Cl.
    *C12Q 1/68*    (2018.01)
    *C12Q 1/70*    (2006.01)

(52) U.S. Cl.
    CPC ............ *C12Q 1/701* (2013.01); *C12Q 1/702* (2013.01); *Y02A 50/51* (2018.01)

(58) Field of Classification Search
    None
    See application file for complete search history.

(56) References Cited

U.S. PATENT DOCUMENTS

| 5,952,202 A | 9/1999 | Aoyagi et al. |
| 9,273,365 B2 | 3/2016 | Carrick et al. |
| 2010/0055676 A1 | 3/2010 | Saito et al. |

FOREIGN PATENT DOCUMENTS

| CN | 101270394 A | 9/2008 |
| WO | 07/105111 A | 9/2007 |
| WO | 08/130519 A | 11/2007 |
| WO | 08/026225 A | 3/2008 |
| WO | 09/044085 A | 4/2009 |

OTHER PUBLICATIONS

Carletti et al. Short Report: Rapid Detection and Quantification of Chikungunya Virus by a One-Step Reverse Transcription-Polymerase Chain Reaction Real-Time Assay. Am. J. Trop. Med. Hyg. 77(3):521-524. (Year: 2007).*

Edwards et al. Molecular diagnosis and analysis of Chikungunya virus. J. Clin. Vir. 39:271-275. (Year: 2007).*
Hasebe et al. Combined Detection and Genotyping of Chikungunya Virus by a Specific Reverse Transcription-Polymerase Chain Reaction. J. Med. Vir. 67:370-374. (Year: 2002).*
Khan et al. Complete nucleotide sequence of chikungunya virus and evidence for an internal polyadenylation site. J. Gen. Vir. 83:3075-3084. (Year: 2002).*
Lanciotti et al. Chikungunya Virus in US Travelers Returning from India, 2006. Emerging Infectious Diseases 13(5):764-767. (Year: 2007).*
Laurent et al. Development of a Sensitive Real-Time Reverse Transcriptase PCR Assay with an Internal Control to Detect and Quantify Chikungunya Virus. Clin. Chem. 53(8):1408-1414. (Year: 2007).*
Panda et al. Rapid and Real-Time Detection of Chikungunya Virus by Reverse Transcription Loop-Mediated Isothermal Amplificatioin Assay. J. Clin. Microbiol. 45(2):351-357. (Year: 2007).*
Pastorino et al. Development of a TaqMan RT-PCR assay without RNA extraction step for the detection and quantification of African Chikungunya viruses. Journal of Virological Methods 124:65-71. (Year: 2005).*
Pfeffer et al. Specific Detection of Chikungunya Virus Using a RT-PCR/Nested PCR Combination. J. Vet. Med. B 49:49-54. (Year: 2002).*
Santhosh et al. Development and evaluation of SYBR Green I-based one-step real-time RT-PCR assay for detection and quantification of Chikungunya virus. J. Clin. Virol. 39:188-193. (Year: 2007).*
Chan et al., "NASBA and other transcription-based amplification methods for research and diagnositc microbiology," Review in Med. Microbiol., 1999, 10(4)185-196, Lippincott Williams & Wilkins, USA.
Database Genbank, Accession AF369024, "Chikungunya virus strain S27-African prototype, complete genome," Jan. 2003, 83(12)3075-3084.
Grivard et al., "Molecular and serological diagnosis of Chikungunya virus infection," Pathol Biol , 2007, 55:490-494, Elsevier, FR.
Rezza et al., "Infection with Chikungunya virus in Italy: an outbreak in a temperate region," The Lancet, 2007, 370:1805-1846, Lancet Publishing Group, USA.
Schuffenecker et al., "Genome Microevolution of Chikungunya Viruses Causing the Indian Ocean Outbreak," PLoS Med., 2006, 3(7):1058-1071, Public Library of Science, USA.
Abd-Eisalam, "Boinformatic tools and guideline for PCR primer design," African Journal of Biotechnology, 2003, 2(5):91-95, Academic Journals, USA.
Lowe et al., "A computer program for selection of oligonucleotide primers for polymerase chain reactions," Nucleic acid research, 1990, vol. 1897, p. 1757-1761.
Nucleic Acid Sequence Search Reports (AC AOJ21250, AOJ21293, AOJ21291), 45 pp.
USPTO Non-Final Rejection, U.S. Appl. No. 12/386,832, dated Nov. 21, 2011.

(Continued)

*Primary Examiner* — Samuel C Woolwine
(74) *Attorney, Agent, or Firm* — Michael J. Gilly; Brian S. Sun

(57) ABSTRACT

Compositions, methods and kits for detecting Chikungunya viral nucleic acids. Particularly described are methods for detecting very low levels of the viral nucleic acids using nucleic acid amplification.

23 Claims, 1 Drawing Sheet
Specification includes a Sequence Listing.

(56) References Cited

OTHER PUBLICATIONS

USPTO Final Rejection, U.S. Appl. No. 12/386,832, dated Jul. 20, 2012.
USPTO Non-Final Rejection, U.S. Appl. No. 12/386,832, dated May 7, 2013.
USPTO Non-Final Rejection, U.S. Appl. No. 12/386,832, dated Nov. 22, 2013.
USPTO Final Rejection, U.S. Appl. No. 12/386,832, dated Jul. 8, 2014.
USPTO Notice of Allowance, U.S. Appl. No. 12/386,832, dated Jul. 8, 2014.
PCT International Preliminary Report on Patentability, PCT Patent Application No. PCT/US2009/002504, dated Oct. 26, 2010.
PCT Search Report and Written Opinion, PCT Patent Application No. PCT/US2009/002504, dated Dec. 3, 2010.
APO Patent Examination Report No. 1, European Patent Application No. 2009239586, dated Jan. 29, 2014.
CIPO Examination Report, Canadian Patent Application No. 2,721,536, dated Feb. 27, 2015.
JPO Official Action, Japanese Patent Application No. 2011-506292, dated Jan. 8, 2014.
EPO Communication pursuant to Article 94(3) EPC, European Patent Application No. 09735119.1, dated Jul. 15, 2013.
EPO Communication under Rule 71(3) EPC, European Patent Application No. 09735119.1, dated Aug. 4, 2014.
EPO extended European search report, European Patent Application No. 14175653.6, dated Nov. 10, 2014.
EPO Communication under Rule 71(3) EPC, European Patent Application No. 14175653.6, dated Nov. 2, 2016.
EPO extended European search report, European Patent Application No. 14175658.5, dated Nov. 5, 2014.
EPO Communication pursuant to Article 94(3) EPC, European Patent Application No. 14 175 658.5, dated Oct. 14, 2016.
EPO Communication under Rule 71(3) EPC, European Patent Application No. 14 175 658.5, dated Dec. 13, 2017.
EPO extended European search report, European Patent Application No. 18174077.0, dated Jul. 4, 2018.
Ho, Phui San et al. "Establishment of one-step SYBR green-based real time-PCR assay for rapid detection and quantification of chikungunya virus infection," Virology Journal, Jan. 21, 2010, p. 13, vol. 7, No. 1, Jan. 21, 2010, Biomed Central, London, GB.
Khan, A H et al. "Chikungunya virus strain S27 prototype, complete genome", Genbank Host—Genbank, Jan. 14, 2003.
Nakoune, E. et al. "Le virus Chikungunya" Ann Biol Clin, Jul-Aug. 2007, pp. 349-356, vol. 65, No. 4.
Parola et al. "Novel Chikungunya Virus Variant in Travelers Returning from Indian Ocean Islands", Emerging Infectious Diseases, Oct. 2006, pp. 1493-1499, vol. 12, No. 10, www.cdc.gov/eid.
Santhosh et al., "Comparative full genome analysis revealed E1:A226V shift in 2007 Indian Chikungunya virus isolates", Virus Research, Apr. 1, 2008, pp. 36-41, vol. 135, http://dx.doi.org/10.1016/j.virusres.2008.02.004, Elsevier.
Arankalle et al., "Genetic divergence of Chikungunya viruses in India (1963-2006) with special reference to the 2005-2006 explosive epidemic," Journal of General Virology, 2007, pp. 1967-1976, vol. 88, DOI 10.1099/vir.0.82714-0, SGM, Great Britain.

* cited by examiner

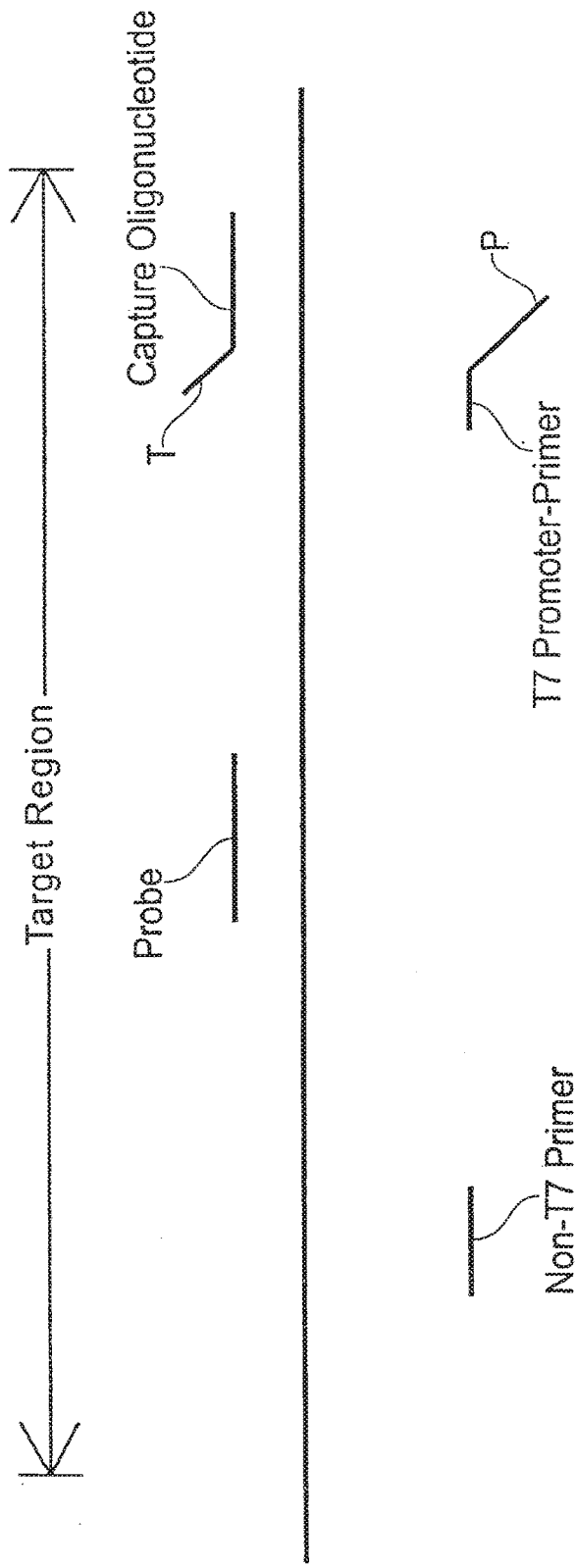

SEQUENCE LISTING

<160> NUMBER OF SEQ ID NOS: 191

<210> SEQ ID NO 1
<211> LENGTH: 152
<212> TYPE: DNA
<213> ORGANISM: Chikungunya virus
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t

<400> SEQUENCE: 1
nacatgcagg gtgcctaaag caaggaaccc caccgtgacg tacgggaaaa accaagtcat    60
catgctnctg tatcctgacc acccaacact cctgtcctac cggaatatgg gagaagaacc   120
aaactatcaa gaagagtggg tgangcataa ga                                 152

<210> SEQ ID NO 2
<211> LENGTH: 148
<212> TYPE: DNA
<213> ORGANISM: Chikungunya virus
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (54)..(55)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t

<400> SEQUENCE: 2
tgggagaaga accaaactat caagaagagt gggtgangca taagaaggaa gtcnngntaa    60
ccgtgccgac tgaagggctc gaggtcacgt ggggcaacaa cgagccgtan aagtattggc   120
cgcagttatc tacaaacggt acagccca                                      148

<210> SEQ ID NO 3
<211> LENGTH: 156
<212> TYPE: DNA
<213> ORGANISM: Chikungunya virus
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (148)..(148)
<223> OTHER INFORMATION: n is a, c, g, or t

<400> SEQUENCE: 3
taagtangac cttgaatgcg cgcagatacc cgtgcacatg aagtccgacg cttcgaagtt 60
cacccatgag aaaccggagg ggtactacaa ctggcaccac ggagcagtac agtactcagg 120
aggccggttc accatcccta caggtgcngg caaacc 156

<210> SEQ ID NO 4
<211> LENGTH: 84
<212> TYPE: DNA
<213> ORGANISM: Chikungunya virus
<220> FEATURE:
<221> NAME/KEY: misc_feature
<222> LOCATION: (82)..(82)
<223> OTHER INFORMATION: n is a, c, g, or t

<400> SEQUENCE: 4
cggtgcccac actgtgagcg cgtacgaaca cgtaacagtg atcccgaaca cggtgggagt 60
accgtataag actctagtca anag 84

<210> SEQ ID NO 5
<211> LENGTH: 108
<212> TYPE: DNA
<213> ORGANISM: Chikungunya virus
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 5
cagnggggat gtgcatgtgt gcacgacgca gatgcatnac accgtangaa ctgacaccag 60
gagctaccgt ccctttcctg cttagcctaa tatgctgcat nagaacag 108

<210> SEQ ID NO 6
<211> LENGTH: 134
<212> TYPE: DNA
<213> ORGANISM: Chikungunya virus
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t

<400> SEQUENCE: 6
tacctgacta cagctgtaag gtcttcaccg gcgtctaccc attnatgtgg ggcggcgcct 60
actgcttctg cgacnctgaa aanacgcant tgagcgaagc acatgtggag aagtccgaat 120
catgcaaaac agaa 134

<210> SEQ ID NO 7
<211> LENGTH: 88
<212> TYPE: DNA

```
<213> ORGANISM: Chikungunya virus
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (82)..(82)
<223> OTHER INFORMATION: n is a, c, g, or t

<400> SEQUENCE: 7
aaantgggcn gatgagcagg tactgaaggc taagaacata ggattatgtt caacagacct      60
gacggaaggt agacgaggca anttgtct                                        88

<210> SEQ ID NO 8
<211> LENGTH: 81
<212> TYPE: DNA
<213> ORGANISM: Chikungunya virus
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t

<400> SEQUENCE: 8
gagaaagctn gcatctgccg caggaaaagt cctggacaga acatctctg gaaagatcgg       60 ggacttacaa gcngtnatgg c                                               81

<210> SEQ ID NO 9
<211> LENGTH: 138
<212> TYPE: DNA
<213> ORGANISM: Chikungunya virus
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t

<400> SEQUENCE: 9
ggcaanctna gcttcacatg ccgctgtgan acagtggttt cgtgtgaggg ctacgtcgtt      60
aagagaataa cgatgagccc aggcctttat ggaaaaacca cagggtatgc ggtaacccac     120
cacgcagacg gattcntg                                                  138

<210> SEQ ID NO 10
<211> LENGTH: 151
<212> TYPE: DNA
<213> ORGANISM: Chikungunya virus
```

<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 10
aaaccacagg gtatgcggta acccaccacg cagacggatt cntgatgtgc aagactaccg    60
acacggttga cggcgaaaga gtgtcattct cggtgtgcac ntacgtgccg gcgaccattt   120
gtgatcaaat gaccggcatc cttgctacag a                                  151

<210> SEQ ID NO 11
<211> LENGTH: 146
<212> TYPE: DNA
<213> ORGANISM: Chikungunya virus
<220> FEATURE:
<221> NAME/KEY: misc_feature
<222> LOCATION: (53)..(53)
<223> OTHER INFORMATION: n is a, c, g, or t

<400> SEQUENCE: 11
gcaagactac cgacacggtt gacggcgaaa gagtgtcatt ctcggtgtgc acntacgtgc    60
cggcgaccat ttgtgatcaa atgaccggca tccttgctac agaagtcacg ccggaggatg   120
cacagaagct gttggtgggg ctgaac                                        146

<210> SEQ ID NO 12
<211> LENGTH: 97
<212> TYPE: DNA
<213> ORGANISM: Chikungunya virus
<220> FEATURE:
<221> NAME/KEY: misc_feature
<222> LOCATION: (40)..(40)
<223> OTHER INFORMATION: n is a, c, g, or t

<400> SEQUENCE: 12
gaacacacta cagaatgtac tggcagcagc cacgaaaagn aactgcaacg tcacacagat    60
gagggaatta cccactttgg actcagcagt attcaac                            97

<210> SEQ ID NO 13
<211> LENGTH: 91
<212> TYPE: DNA
<213> ORGANISM: Chikungunya virus
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t

<400> SEQUENCE: 13
aagaacactn acctgctgct gtctatgggc attnaagaag cagaaaacac acacggtcta    60
caagaggcct gatacccagt caatncagaa g                                  91

<210> SEQ ID NO 14
<211> LENGTH: 167
<212> TYPE: DNA

```
<213> ORGANISM: Chikungunya virus
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (116)..(116)
<223> OTHER INFORMATION: n is a, c, g, or t

<400> SEQUENCE: 14
acccgaagca gtgcggcttc ttcaatatga tgcagatgaa agtcaactan aatcanaaca      60
tctgcaccca agtgtaccac aaaagtatct ccaggcggtg tacactgcct gtgacngcca     120
ttgtgtcatc gttgcattac gaaggcaaaa tgcgcactac gaatgag                   167

<210> SEQ ID NO 15
<211> LENGTH: 120
<212> TYPE: DNA
<213> ORGANISM: Chikungunya virus
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t

<400> SEQUENCE: 15
nggtaatgtc catggccacc tttgcaagct ccagatccaa cttcgagaag ctcagaggac      60
ccgtcataac tttgtacggc ggtcctaaat aggtacgcac tacagctacc tattttgnca    120

<210> SEQ ID NO 16
<211> LENGTH: 132
<212> TYPE: DNA
<213> ORGANISM: Chikungunya virus
<220> FEATURE:
<221> NAME/KEY: misc_feature
<222> LOCATION: (57)..(57)
<223> OTHER INFORMATION: n is a, c, g, or t

<400> SEQUENCE: 16
gtgcctaaag caaggaaccc caccgtgacg tacgggaaaa accaagtcat catgctnctg      60
tatcctgacc acccaacact cctgtcctac cggaatatgg gagaagaacc aaactatcaa    120
gaagagtggg tg                                                         132

<210> SEQ ID NO 17
<211> LENGTH: 127
<212> TYPE: DNA
<213> ORGANISM: Chikungunya virus
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
```

<222> LOCATION: (99)..(99)
<223> OTHER INFORMATION: n is a, c, g, or t

<400> SEQUENCE: 17
ccaaactatc aagaagagtg ggtgangcat aagaaggaag tcnngntaac cgtgccgact    60
gaagggctcg aggtcacgtg gggcaacaac gagccgtana agtattggcc gcagttatct   120
acaaacg                                                              127

<210> SEQ ID NO 18
<211> LENGTH: 136
<212> TYPE: DNA
<213> ORGANISM: Chikungunya virus

<400> SEQUENCE: 18
cttgaatgcg cgcagatacc cgtgcacatg aagtccgacg cttcgaagtt cacccatgag    60
aaaccggagg ggtactacaa ctggcaccac ggagcagtac agtactcagg aggccggttc   120
accatcccta caggtg                                                   136

<210> SEQ ID NO 19
<211> LENGTH: 64
<212> TYPE: DNA
<213> ORGANISM: Chikungunya virus

<400> SEQUENCE: 19
actgtgagcg cgtacgaaca cgtaacagtg atcccgaaca cggtgggagt accgtataag    60
actc                                                                 64

<210> SEQ ID NO 20
<211> LENGTH: 88
<212> TYPE: DNA
<213> ORGANISM: Chikungunya virus
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t

<400> SEQUENCE: 20
gtgcatgtgt gcacgacgca gatgcatnac accgtangaa ctgacaccag gagctaccgt    60 cccttctcctg cttagcctaa tatgctgc                                      88

<210> SEQ ID NO 21
<211> LENGTH: 115
<212> TYPE: DNA
<213> ORGANISM: Chikungunya virus
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t

<400> SEQUENCE: 21
cagctgtaag gtcttcaccg gcgtctaccc attnatgtgg ggcggcgcct actgcttctg    60
cgacnctgaa aanacgcant tgagcgaagc acatgtggag aagtccgaat catgc        115

<210> SEQ ID NO 22
<211> LENGTH: 68
<212> TYPE: DNA
<213> ORGANISM: Chikungunya virus

<400> SEQUENCE: 22
gatgagcagg tactgaaggc taagaacata ggattatgtt caacagacct gacggaaggt    60
agacgagg                                                              68

<210> SEQ ID NO 23
<211> LENGTH: 62
<212> TYPE: DNA
<213> ORGANISM: Chikungunya virus

<400> SEQUENCE: 23
gcatctgccg caggaaaagt cctggacaga aacatctctg gaaagatcgg ggacttacaa    60
gc                                                                    62

<210> SEQ ID NO 24
<211> LENGTH: 118
<212> TYPE: DNA
<213> ORGANISM: Chikungunya virus
<220> FEATURE:
<221> NAME/KEY: misc_feature
<222> LOCATION: (20)..(20)
<223> OTHER INFORMATION: n is a, c, g, or t

<400> SEQUENCE: 24
gcttcacatg ccgctgtgan acagtggttt cgtgtgaggg ctacgtcgtt aagagaataa    60
cgatgagccc aggcctttat ggaaaaacca cagggtatgc ggtaacccac cacgcaga     118

<210> SEQ ID NO 25
<211> LENGTH: 131
<212> TYPE: DNA
<213> ORGANISM: Chikungunya virus
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t

<400> SEQUENCE: 25
gtatgcggta acccaccacg cagacggatt cntgatgtgc aagactaccg acacggttga    60
cggcgaaaga gtgtcattct cggtgtgcac ntacgtgccg gcgaccattt gtgatcaaat   120
gaccggcatc c                                                         131

<210> SEQ ID NO 26
<211> LENGTH: 124
<212> TYPE: DNA
<213> ORGANISM: Chikungunya virus
<220> FEATURE:
<221> NAME/KEY: misc_feature
<222> LOCATION: (42)..(42)
<223> OTHER INFORMATION: n is a, c, g, or t

<400> SEQUENCE: 26

```
gacacggttg acggcgaaag agtgtcattc tcggtgtgca cntacgtgcc ggcgaccatt    60
tgtgatcaaa tgaccggcat ccttgctaca gaagtcacgc cggaggatgc acagaagctg   120
ttgg                                                                124
```

<210> SEQ ID NO 27
<211> LENGTH: 77
<212> TYPE: DNA
<213> ORGANISM: Chikungunya virus
<220> FEATURE:
<221> NAME/KEY: misc_feature
<222> LOCATION: (30)..(30)
<223> OTHER INFORMATION: n is a, c, g, or t

<400> SEQUENCE: 27

```
cagaatgtac tggcagcagc cacgaaaagn aactgcaacg tcacacagat gagggaatta    60
cccactttgg actcagc                                                   77
```

<210> SEQ ID NO 28
<211> LENGTH: 71
<212> TYPE: DNA
<213> ORGANISM: Chikungunya virus
<220> FEATURE:
<221> NAME/KEY: misc_feature
<222> LOCATION: (24)..(24)
<223> OTHER INFORMATION: n is a, c, g, or t

<400> SEQUENCE: 28

```
acctgctgct gtctatgggc attnaagaag cagaaaacac acacggtcta caagaggcct    60
gatacccagt c                                                         71
```

<210> SEQ ID NO 29
<211> LENGTH: 147
<212> TYPE: DNA
<213> ORGANISM: Chikungunya virus
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t

<400> SEQUENCE: 29

```
gtgcggcttc ttcaatatga tgcagatgaa agtcaactan aatcanaaca tctgcaccca    60
agtgtaccac aaaagtatct ccaggcggtg tacactgcct gtgacngcca ttgtgtcatc   120
gttgcattac gaaggcaaaa tgcgcac                                       147
```

<210> SEQ ID NO 30
<211> LENGTH: 100
<212> TYPE: DNA
<213> ORGANISM: Chikungunya virus

<400> SEQUENCE: 30

```
catggccacc tttgcaagct ccagatccaa cttcgagaag ctcagaggac ccgtcataac    60
tttgtacggc ggtcctaaat aggtacgcac tacagctacc                         100
```

<210> SEQ ID NO 31

```
<211> LENGTH: 44
<212> TYPE: DNA
<213> ORGANISM: Chikungunya virus
<220> FEATURE:
<221> NAME/KEY: misc_feature
<222> LOCATION: (9)..(9)
<223> OTHER INFORMATION: n is a, c, g, or t

<400> SEQUENCE: 31
tcttatgcnt cacccactct tcttgatagt ttggttcttc tccc            44

<210> SEQ ID NO 32
<211> LENGTH: 46
<212> TYPE: DNA
<213> ORGANISM: Chikungunya virus
<220> FEATURE:
<221> NAME/KEY: misc_feature
<222> LOCATION: (39)..(39)
<223> OTHER INFORMATION: n is a, c, g, or t

<400> SEQUENCE: 32
tgggctgtac cgtttgtaga taactgcggc caatacttnt acggct            46

<210> SEQ ID NO 33
<211> LENGTH: 43
<212> TYPE: DNA
<213> ORGANISM: Chikungunya virus

<400> SEQUENCE: 33
ccggcctcct gagtactgta ctgctccgtg gtgccagttg tag              43

<210> SEQ ID NO 34
<211> LENGTH: 40
<212> TYPE: DNA
<213> ORGANISM: Chikungunya virus
<220> FEATURE:
<221> NAME/KEY: misc_feature
<222> LOCATION: (9)..(9)
<223> OTHER INFORMATION: n is a, c, g, or t

<400> SEQUENCE: 34
ggtttgccng cacctgtagg gatggtgaac cggcctcctg               40

<210> SEQ ID NO 35
<211> LENGTH: 43
<212> TYPE: DNA
<213> ORGANISM: Chikungunya virus
<220> FEATURE:
<221> NAME/KEY: misc_feature
<222> LOCATION: (3)..(3)
<223> OTHER INFORMATION: n is a, c, g, or t

<400> SEQUENCE: 35
ctnttgacta gagtcttata cggtactccc accgtgttcg gga              43

<210> SEQ ID NO 36
<211> LENGTH: 51
<212> TYPE: DNA
<213> ORGANISM: Chikungunya virus
<220> FEATURE:
<221> NAME/KEY: misc_feature
<222> LOCATION: (8)..(8)
<223> OTHER INFORMATION: n is a, c, g, or t

<400> SEQUENCE: 36
ctgttctnat gcagcatatt aggctaagca ggaaagggac ggtagctcct g        51
```

```
<210> SEQ ID NO 37
<211> LENGTH: 37
<212> TYPE: DNA
<213> ORGANISM: Chikungunya virus

<400> SEQUENCE: 37
ttctgttttg catgattcgg acttctccac atgtgct                              37

<210> SEQ ID NO 38
<211> LENGTH: 40
<212> TYPE: DNA
<213> ORGANISM: Chikungunya virus
<220> FEATURE:
<221> NAME/KEY: misc_feature
<222> LOCATION: (7)..(7)
<223> OTHER INFORMATION: n is a, c, g, or t

<400> SEQUENCE: 38
agacaanttg cctcgtctac cttccgtcag gtctgttgaa                           40

<210> SEQ ID NO 39
<211> LENGTH: 42
<212> TYPE: DNA
<213> ORGANISM: Chikungunya virus
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 39
gccatnacng cttgtaagtc cccgatcttt ccagagatgt tt                        42

<210> SEQ ID NO 40
<211> LENGTH: 40
<212> TYPE: DNA
<213> ORGANISM: Chikungunya virus

<400> SEQUENCE: 40
ctgcgtggtg ggttaccgca taccctgtgg tttttccata                           40

<210> SEQ ID NO 41
<211> LENGTH: 45
<212> TYPE: DNA
<213> ORGANISM: Chikungunya virus
<220> FEATURE:
<221> NAME/KEY: misc_feature
<222> LOCATION: (3)..(3)
<223> OTHER INFORMATION: n is a, c, g, or t

<400> SEQUENCE: 41
cangaatccg tctgcgtggt gggttaccgc ataccctgtg gtttt                     45

<210> SEQ ID NO 42
<211> LENGTH: 42
<212> TYPE: DNA
<213> ORGANISM: Chikungunya virus
<220> FEATURE:
<221> NAME/KEY: misc_feature
<222> LOCATION: (36)..(36)
<223> OTHER INFORMATION: n is a, c, g, or t

<400> SEQUENCE: 42
ccggtcattt gatcacaaat ggtcgccggc acgtangtgc ac                        42
```

<210> SEQ ID NO 43
<211> LENGTH: 47
<212> TYPE: DNA
<213> ORGANISM: Chikungunya virus

<400> SEQUENCE: 43
tctgtagcaa ggatgccggt catttgatca caaatggtcg ccggcac 47

<210> SEQ ID NO 44
<211> LENGTH: 41
<212> TYPE: DNA
<213> ORGANISM: Chikungunya virus

<400> SEQUENCE: 44
tcagccccac caacagcttc tgtgcatcct ccggcgtgac t 41

<210> SEQ ID NO 45
<211> LENGTH: 43
<212> TYPE: DNA
<213> ORGANISM: Chikungunya virus

<400> SEQUENCE: 45
ttcagcccca ccaacagctt ctgtgcatcc tccggcgtga ctt 43

<210> SEQ ID NO 46
<211> LENGTH: 44
<212> TYPE: DNA
<213> ORGANISM: Chikungunya virus

<400> SEQUENCE: 46
gttgaatact gctgagtcca aagtgggtaa ttccctcatc tgtg 44

<210> SEQ ID NO 47
<211> LENGTH: 46
<212> TYPE: DNA
<213> ORGANISM: Chikungunya virus
<220> FEATURE:
<221> NAME/KEY: misc_feature
<222> LOCATION: (7)..(7)
<223> OTHER INFORMATION: n is a, c, g, or t

<400> SEQUENCE: 47
cttctgnatt gactgggtat caggcctctt gtagaccgtg tgtgtt 46

<210> SEQ ID NO 48
<211> LENGTH: 48
<212> TYPE: DNA
<213> ORGANISM: Chikungunya virus

<400> SEQUENCE: 48
ctcattcgta gtgcgcattt tgccttcgta atgcaacgat gacacaat 48

<210> SEQ ID NO 49
<211> LENGTH: 38
<212> TYPE: DNA
<213> ORGANISM: Chikungunya virus
<220> FEATURE:
<221> NAME/KEY: misc_feature
<222> LOCATION: (10)..(10)
<223> OTHER INFORMATION: n is a, c, g, or t

<400> SEQUENCE: 49
cacaatggcn gtcacaggca gtgtacaccg cctggaga 38

<210> SEQ ID NO 50
<211> LENGTH: 47
<212> TYPE: DNA
<213> ORGANISM: Chikungunya virus
<220> FEATURE:
<221> NAME/KEY: misc_feature
<222> LOCATION: (3)..(3)
<223> OTHER INFORMATION: n is a, c, g, or t

<400> SEQUENCE: 50
tgncaaaata ggtagctgta gtgcgtacct atttaggacc gccgtac       47

<210> SEQ ID NO 51
<211> LENGTH: 40
<212> TYPE: DNA
<213> ORGANISM: Chikungunya virus
<220> FEATURE:
<221> NAME/KEY: misc_feature
<222> LOCATION: (10)..(10)
<223> OTHER INFORMATION: n is a, c, g, or t

<400> SEQUENCE: 51
catcatgctn ctgtatcctg accacccaac actcctgtcc       40

<210> SEQ ID NO 52
<211> LENGTH: 38
<212> TYPE: DNA
<213> ORGANISM: Chikungunya virus
<220> FEATURE:
<221> NAME/KEY: misc_feature
<222> LOCATION: (1)..(1)
<223> OTHER INFORMATION: n is a, c, g, or t

<400> SEQUENCE: 52
nacatgcagg gtgcctaaag caaggaaccc caccgtga       38

<210> SEQ ID NO 53
<211> LENGTH: 44
<212> TYPE: DNA
<213> ORGANISM: Chikungunya virus
<220> FEATURE:
<221> NAME/KEY: misc_feature
<222> LOCATION: (36)..(36)
<223> OTHER INFORMATION: n is a, c, g, or t

<400> SEQUENCE: 53
gggagaagaa ccaaactatc aagaagagtg ggtgangcat aaga       44

<210> SEQ ID NO 54
<211> LENGTH: 39
<212> TYPE: DNA
<213> ORGANISM: Chikungunya virus
<220> FEATURE:
<221> NAME/KEY: misc_feature
<222> LOCATION: (7)..(7)
<223> OTHER INFORMATION: n is a, c, g, or t

<400> SEQUENCE: 54
taagtangac cttgaatgcg cgcagatacc cgtgcacat       39

<210> SEQ ID NO 55
<211> LENGTH: 44
<212> TYPE: DNA
<213> ORGANISM: Chikungunya virus

<400> SEQUENCE: 55
gatacccgtg cacatgaagt ccgacgcttc gaagttcacc catg       44

```
<210> SEQ ID NO 56
<211> LENGTH: 41
<212> TYPE: DNA
<213> ORGANISM: Chikungunya virus

<400> SEQUENCE: 56
cggtgcccac actgtgagcg cgtacgaaca cgtaacagtg a                    41

<210> SEQ ID NO 57
<211> LENGTH: 44
<212> TYPE: DNA
<213> ORGANISM: Chikungunya virus
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t

<400> SEQUENCE: 57 cagngggat gtgcatgtgt gcacgacgca gatgcatnac accg                  44

<210> SEQ ID NO 58
<211> LENGTH: 38
<212> TYPE: DNA
<213> ORGANISM: Chikungunya virus

<400> SEQUENCE: 58
tacctgacta cagctgtaag gtcttcaccg gcgtctac                        38

<210> SEQ ID NO 59
<211> LENGTH: 39
<212> TYPE: DNA
<213> ORGANISM: Chikungunya virus
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 59
aaantgggcn gatgagcagg tactgaaggc taagaacat                       39

<210> SEQ ID NO 60
<211> LENGTH: 39
<212> TYPE: DNA
<213> ORGANISM: Chikungunya virus
<220> FEATURE:
<221> NAME/KEY: misc_feature
<222> LOCATION: (10)..(10)
<223> OTHER INFORMATION: n is a, c, g, or t

<400> SEQUENCE: 60
gagaaagctn gcatctgccg caggaaaagt cctggacag                       39

<210> SEQ ID NO 61
<211> LENGTH: 38
<212> TYPE: DNA
<213> ORGANISM: Chikungunya virus
<220> FEATURE:
<221> NAME/KEY: misc_feature
<222> LOCATION: (6)..(6)
<223> OTHER INFORMATION: n is a, c, g, or t
```

```
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t

<400> SEQUENCE: 61
ggcaanctna gcttcacatg ccgctgtgan acagtggt                           38

<210> SEQ ID NO 62
<211> LENGTH: 43
<212> TYPE: DNA
<213> ORGANISM: Chikungunya virus
<220> FEATURE:
<221> NAME/KEY: misc_feature
<222> LOCATION: (42)..(42)
<223> OTHER INFORMATION: n is a, c, g, or t

<400> SEQUENCE: 62
aaaccacagg gtatgcggta acccaccacg cagacggatt cnt                    43

<210> SEQ ID NO 63
<211> LENGTH: 42
<212> TYPE: DNA
<213> ORGANISM: Chikungunya virus

<400> SEQUENCE: 63
caagactacc gacacggttg acggcgaaag agtgtcattc tc                     42

<210> SEQ ID NO 64
<211> LENGTH: 38
<212> TYPE: DNA
<213> ORGANISM: Chikungunya virus
<220> FEATURE:
<221> NAME/KEY: misc_feature
<222> LOCATION: (29)..(29)
<223> OTHER INFORMATION: n is a, c, g, or t

<400> SEQUENCE: 64
gcgaaagagt gtcattctcg gtgtgcacnt acgtgccg                          38

<210> SEQ ID NO 65
<211> LENGTH: 40
<212> TYPE: DNA
<213> ORGANISM: Chikungunya virus
<220> FEATURE:
<221> NAME/KEY: misc_feature
<222> LOCATION: (40)..(40)
<223> OTHER INFORMATION: n is a, c, g, or t

<400> SEQUENCE: 65
gaacacacta cagaatgtac tggcagcagc cacgaaaagn                        40

<210> SEQ ID NO 66
<211> LENGTH: 43
<212> TYPE: DNA
<213> ORGANISM: Chikungunya virus
<220> FEATURE:
<221> NAME/KEY: misc_feature
<222> LOCATION: (34)..(34)
<223> OTHER INFORMATION: n is a, c, g, or t

<400> SEQUENCE: 66
actacagaat gtactggcag cagccacgaa aagnaactgc aac                    43
```

<210> SEQ ID NO 67
<211> LENGTH: 37
<212> TYPE: DNA
<213> ORGANISM: Chikungunya virus
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t

<400> SEQUENCE: 67
aagaacactn acctgctgct gtctatgggc attnaag                         37

<210> SEQ ID NO 68
<211> LENGTH: 39
<212> TYPE: DNA
<213> ORGANISM: Chikungunya virus

<400> SEQUENCE: 68
acccgaagca gtgcggcttc ttcaatatga tgcagatga                       39

<210> SEQ ID NO 69
<211> LENGTH: 39
<212> TYPE: DNA
<213> ORGANISM: Chikungunya virus
<220> FEATURE:
<221> NAME/KEY: misc_feature
<222> LOCATION: (1)..(1)
<223> OTHER INFORMATION: n is a, c, g, or t

<400> SEQUENCE: 69
nggtaatgtc catggccacc tttgcaagct ccagatcca                       39

<210> SEQ ID NO 70
<211> LENGTH: 39
<212> TYPE: DNA
<213> ORGANISM: Chikungunya virus

<400> SEQUENCE: 70
acccaacact cctgtcctac cggaatatgg gagaagaac                       39

<210> SEQ ID NO 71
<211> LENGTH: 39
<212> TYPE: DNA
<213> ORGANISM: Chikungunya virus

<400> SEQUENCE: 71
cctgtcctac cggaatatgg gagaagaacc aaactatca                       39

<210> SEQ ID NO 72
<211> LENGTH: 42
<212> TYPE: DNA
<213> ORGANISM: Chikungunya virus
<220> FEATURE:
<221> NAME/KEY: misc_feature
<222> LOCATION: (41)..(41)
<223> OTHER INFORMATION: n is a, c, g, or t

<400> SEQUENCE: 72
ctgaagggct cgaggtcacg tggggcaaca acgagccgta na                   42

<210> SEQ ID NO 73
<211> LENGTH: 44

```
<212> TYPE: DNA
<213> ORGANISM: Chikungunya virus

<400> SEQUENCE: 73
gttcacccat gagaaaccgg aggggtacta caactggcac cacg                    44

<210> SEQ ID NO 74
<211> LENGTH: 40
<212> TYPE: DNA
<213> ORGANISM: Chikungunya virus

<400> SEQUENCE: 74
gtacgaacac gtaacagtga tcccgaacac ggtgggagta                         40

<210> SEQ ID NO 75
<211> LENGTH: 37
<212> TYPE: DNA
<213> ORGANISM: Chikungunya virus
<220> FEATURE:
<221> NAME/KEY: misc_feature
<222> LOCATION: (7)..(7)
<223> OTHER INFORMATION: n is a, c, g, or t

<400> SEQUENCE: 75
accgtangaa ctgacaccag gagctaccgt ccctttc                            37

<210> SEQ ID NO 76
<211> LENGTH: 34
<212> TYPE: DNA
<213> ORGANISM: Chikungunya virus
<220> FEATURE:
<221> NAME/KEY: misc_feature
<222> LOCATION: (27)..(27)
<223> OTHER INFORMATION: n is a, c, g, or t

<400> SEQUENCE: 76
ggggcggcgc ctactgcttc tgcgacnctg aaaa                               34

<210> SEQ ID NO 77
<211> LENGTH: 38
<212> TYPE: DNA
<213> ORGANISM: Chikungunya virus

<400> SEQUENCE: 77
taagaacata ggattatgtt caacagacct gacggaag                           38

<210> SEQ ID NO 78
<211> LENGTH: 38
<212> TYPE: DNA
<213> ORGANISM: Chikungunya virus

<400> SEQUENCE: 78
caggaaaagt cctggacaga aacatctctg gaaagatc                           38

<210> SEQ ID NO 79
<211> LENGTH: 38
<212> TYPE: DNA
<213> ORGANISM: Chikungunya virus

<400> SEQUENCE: 79
tgagggctac gtcgttaaga gaataacgat gagcccag                           38

<210> SEQ ID NO 80
<211> LENGTH: 38
<212> TYPE: DNA
```

<213> ORGANISM: Chikungunya virus
<220> FEATURE:
<221> NAME/KEY: misc_feature
<222> LOCATION: (29)..(29)
<223> OTHER INFORMATION: n is a, c, g, or t

<400> SEQUENCE: 80
gcgaaagagt gtcattctcg gtgtgcacnt acgtgccg                              38

<210> SEQ ID NO 81
<211> LENGTH: 39
<212> TYPE: DNA
<213> ORGANISM: Chikungunya virus

<400> SEQUENCE: 81
gtgccggcga ccatttgtga tcaaatgacc ggcatcctt                             39

<210> SEQ ID NO 82
<211> LENGTH: 39
<212> TYPE: DNA
<213> ORGANISM: Chikungunya virus
<220> FEATURE:
<221> NAME/KEY: misc_feature
<222> LOCATION: (8)..(8)
<223> OTHER INFORMATION: n is a, c, g, or t

<400> SEQUENCE: 82
cgaaaagnaa ctgcaacgtc acacagatga gggaattac                             39

<210> SEQ ID NO 83
<211> LENGTH: 38
<212> TYPE: DNA
<213> ORGANISM: Chikungunya virus
<220> FEATURE:
<221> NAME/KEY: misc_feature
<222> LOCATION: (8)..(8)
<223> OTHER INFORMATION: n is a, c, g, or t

<400> SEQUENCE: 83
gggcattnaa gaagcagaaa acacacacgg tctacaag                              38

<210> SEQ ID NO 84
<211> LENGTH: 40
<212> TYPE: DNA
<213> ORGANISM: Chikungunya virus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 84
tanaatcana acatctgcac ccaagtgtac cacaaaagta                            40

<210> SEQ ID NO 85
<211> LENGTH: 40
<212> TYPE: DNA
<213> ORGANISM: Chikungunya virus

<400> SEQUENCE: 85
tccaacttcg agaagctcag aggacccgtc ataactttgt                            40

<210> SEQ ID NO 86
<211> LENGTH: 48

```
<212> TYPE: RNA
<213> ORGANISM: Chikungunya virus
<220> FEATURE:
<221> NAME/KEY: misc_feature
<222> LOCATION: (42)..(42)
<223> OTHER INFORMATION: n is a, c, g, or u

<400> SEQUENCE: 86
uuguguagaa cagacuugua cgcggaauuc ggcgcuggcu anggccgu         48

<210> SEQ ID NO 87
<211> LENGTH: 51
<212> TYPE: RNA
<213> ORGANISM: Chikungunya virus
<220> FEATURE:
<221> NAME/KEY: misc_feature
<222> LOCATION: (46)..(46)
<223> OTHER INFORMATION: n is a, c, g, or u
<220> FEATURE:
<221> NAME/KEY: misc_feature
<222> LOCATION: (49)..(49)
<223> OTHER INFORMATION: n is a, c, g, or u

<400> SEQUENCE: 87
ggauacaacu gcaucuauga ucuucacuuc cauguucauc caagungcnc a       51

<210> SEQ ID NO 88
<211> LENGTH: 48
<212> TYPE: RNA
<213> ORGANISM: Chikungunya virus

<400> SEQUENCE: 88
gcaaacgccu cgucuacgua caacacgucg acuggucugu ugcaucca          48

<210> SEQ ID NO 89
<211> LENGTH: 46
<212> TYPE: RNA
<213> ORGANISM: Chikungunya virus
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: misc_feature
<222> LOCATION: (6)..(7)
<223> OTHER INFORMATION: n is a, c, g, or u
<220> FEATURE:
<221> NAME/KEY: misc_feature
<222> LOCATION: (10)..(10)
<223> OTHER INFORMATION: n is a, c, g, or u
<220> FEATURE:
<221> NAME/KEY: misc_feature
<222> LOCATION: (46)..(46)
<223> OTHER INFORMATION: n is a, c, g, or u

<400> SEQUENCE: 89
agunannuun uuccuuggu aaaggacgcg gagcuuagcu gaugcn             46

<210> SEQ ID NO 90
<211> LENGTH: 27
<212> TYPE: DNA
<213> ORGANISM: Artificial
<220> FEATURE:
<223> OTHER INFORMATION: Synthetic promoter for T7 RNA polymerase

<400> SEQUENCE: 90
aatttaatac gactcactat agggaga                                27

<210> SEQ ID NO 91
```

```
<211> LENGTH: 24
<212> TYPE: DNA
<213> ORGANISM: Chikungunya virus

<400> SEQUENCE: 91
cacccactct tcttgatagt ttgg                                          24

<210> SEQ ID NO 92
<211> LENGTH: 26
<212> TYPE: DNA
<213> ORGANISM: Chikungunya virus

<400> SEQUENCE: 92
cgtttgtaga taactgcggc caatac                                        26

<210> SEQ ID NO 93
<211> LENGTH: 23
<212> TYPE: DNA
<213> ORGANISM: Chikungunya virus

<400> SEQUENCE: 93
gagtactgta ctgctccgtg gtg                                           23

<210> SEQ ID NO 94
<211> LENGTH: 20
<212> TYPE: DNA
<213> ORGANISM: Chikungunya virus

<400> SEQUENCE: 94
cacctgtagg gatggtgaac                                               20

<210> SEQ ID NO 95
<211> LENGTH: 23
<212> TYPE: DNA
<213> ORGANISM: Chikungunya virus

<400> SEQUENCE: 95
gagtcttata cggtactccc acc                                           23

<210> SEQ ID NO 96
<211> LENGTH: 31
<212> TYPE: DNA
<213> ORGANISM: Chikungunya virus

<400> SEQUENCE: 96
gcagcatatt aggctaagca ggaaagggac g                                  31

<210> SEQ ID NO 97
<211> LENGTH: 18
<212> TYPE: DNA
<213> ORGANISM: Chikungunya virus

<400> SEQUENCE: 97
gcatgattcg gacttctc                                                 18

<210> SEQ ID NO 98
<211> LENGTH: 20
<212> TYPE: DNA
<213> ORGANISM: Chikungunya virus

<400> SEQUENCE: 98
cctcgtctac cttccgtcag                                               20
```

```
<210> SEQ ID NO 99
<211> LENGTH: 23
<212> TYPE: DNA
<213> ORGANISM: Chikungunya virus

<400> SEQUENCE: 99
gcttgtaagt ccccgatctt tcc                                           23

<210> SEQ ID NO 100
<211> LENGTH: 20
<212> TYPE: DNA
<213> ORGANISM: Chikungunya virus

<400> SEQUENCE: 100
ggttaccgca taccctgtgg                                               20

<210> SEQ ID NO 101
<211> LENGTH: 25
<212> TYPE: DNA
<213> ORGANISM: Chikungunya virus

<400> SEQUENCE: 101
tctgcgtggt gggttaccgc atacc                                         25

<210> SEQ ID NO 102
<211> LENGTH: 22
<212> TYPE: DNA
<213> ORGANISM: Chikungunya virus

<400> SEQUENCE: 102
gatcacaaat ggtcgccggc ac                                            22

<210> SEQ ID NO 103
<211> LENGTH: 27
<212> TYPE: DNA
<213> ORGANISM: Chikungunya virus

<400> SEQUENCE: 103
ggatgccggt catttgatca caaatgg                                       27

<210> SEQ ID NO 104
<211> LENGTH: 21
<212> TYPE: DNA
<213> ORGANISM: Chikungunya virus

<400> SEQUENCE: 104
caacagcttc tgtgcatcct c                                             21

<210> SEQ ID NO 105
<211> LENGTH: 23
<212> TYPE: DNA
<213> ORGANISM: Chikungunya virus

<400> SEQUENCE: 105
ccaacagctt ctgtgcatcc tcc                                           23

<210> SEQ ID NO 106
<211> LENGTH: 24
<212> TYPE: DNA
<213> ORGANISM: Chikungunya virus

<400> SEQUENCE: 106
gctgagtcca aagtgggtaa ttcc                                          24
```

```
<210> SEQ ID NO 107
<211> LENGTH: 26
<212> TYPE: DNA
<213> ORGANISM: Chikungunya virus

<400> SEQUENCE: 107
gactgggtat caggcctctt gtagac                                        26

<210> SEQ ID NO 108
<211> LENGTH: 28
<212> TYPE: DNA
<213> ORGANISM: Chikungunya virus

<400> SEQUENCE: 108
gtgcgcattt tgccttcgta atgcaacg                                      28

<210> SEQ ID NO 109
<211> LENGTH: 18
<212> TYPE: DNA
<213> ORGANISM: Chikungunya virus

<400> SEQUENCE: 109
gtcacaggca gtgtacac                                                 18

<210> SEQ ID NO 110
<211> LENGTH: 27
<212> TYPE: DNA
<213> ORGANISM: Chikungunya virus

<400> SEQUENCE: 110
ggtagctgta gtgcgtacct atttagg                                       27

<210> SEQ ID NO 111
<211> LENGTH: 51
<212> TYPE: DNA
<213> ORGANISM: Artificial
<220> FEATURE:
<223> OTHER INFORMATION: T7 promoter-primer for amplifying CHIKV nucleic
      acids in System 1

<400> SEQUENCE: 111
aatttaatac gactcactat agggagacac ccactcttct tgatagtttg g            51

<210> SEQ ID NO 112
<211> LENGTH: 53
<212> TYPE: DNA
<213> ORGANISM: Artificial
<220> FEATURE:
<223> OTHER INFORMATION: T7 promoter-primer for amplifying CHIKV nucleic
      acids in System 2

<400> SEQUENCE: 112
aatttaatac gactcactat agggagacgt ttgtagataa ctgcggccaa tac          53

<210> SEQ ID NO 113
<211> LENGTH: 50
<212> TYPE: DNA
<213> ORGANISM: Artificial
<220> FEATURE:
<223> OTHER INFORMATION: T7 promoter-primer for amplifying CHIKV nucleic
      acids in System 3

<400> SEQUENCE: 113
aatttaatac gactcactat agggagagag tactgtactg ctccgtggtg              50
```

-continued

```
<210> SEQ ID NO 114
<211> LENGTH: 47
<212> TYPE: DNA
<213> ORGANISM: Artificial
<220> FEATURE:
<223> OTHER INFORMATION: T7 promoter-primer for amplifying CHIKV nucleic
      acids in System 3

<400> SEQUENCE: 114
aatttaatac gactcactat agggagacac ctgtagggat ggtgaac                47

<210> SEQ ID NO 115
<211> LENGTH: 50
<212> TYPE: DNA
<213> ORGANISM: Artificial
<220> FEATURE:
<223> OTHER INFORMATION: T7 promoter-primer for amplifying CHIKV nucleic
      acids in System 4

<400> SEQUENCE: 115
aatttaatac gactcactat agggagagag tcttatacgg tactcccacc             50

<210> SEQ ID NO 116
<211> LENGTH: 58
<212> TYPE: DNA
<213> ORGANISM: Artificial
<220> FEATURE:
<223> OTHER INFORMATION: T7 promoter-primer for amplifying CHIKV nucleic
      acids in System 5

<400> SEQUENCE: 116
aatttaatac gactcactat agggagagca gcatattagg ctaagcagga aagggacg    58

<210> SEQ ID NO 117
<211> LENGTH: 45
<212> TYPE: DNA
<213> ORGANISM: Artificial
<220> FEATURE:
<223> OTHER INFORMATION: T7 promoter-primer for amplifying CHIKV nucleic
      acids in System 6

<400> SEQUENCE: 117
aatttaatac gactcactat agggagagca tgattcggac ttctc                  45

<210> SEQ ID NO 118
<211> LENGTH: 47
<212> TYPE: DNA
<213> ORGANISM: Artificial
<220> FEATURE:
<223> OTHER INFORMATION: T7 promoter-primer for amplifying CHIKV nucleic
      acids in System 7

<400> SEQUENCE: 118
aatttaatac gactcactat agggagacct cgtctacctt ccgtcag                47

<210> SEQ ID NO 119
<211> LENGTH: 50
<212> TYPE: DNA
<213> ORGANISM: Artificial
<220> FEATURE:
<223> OTHER INFORMATION: T7 promoter-primer for amplifying CHIKV nucleic
      acids in System 8

<400> SEQUENCE: 119
aatttaatac gactcactat agggagagct tgtaagtccc cgatctttcc             50
```

<210> SEQ ID NO 120
<211> LENGTH: 47
<212> TYPE: DNA
<213> ORGANISM: Artificial
<220> FEATURE:
<223> OTHER INFORMATION: T7 promoter-primer for amplifying CHIKV nucleic
acids in System 9

<400> SEQUENCE: 120
aatttaatac gactcactat agggagaggt taccgcatac cctgtgg          47

<210> SEQ ID NO 121
<211> LENGTH: 52
<212> TYPE: DNA
<213> ORGANISM: Artificial
<220> FEATURE:
<223> OTHER INFORMATION: T7 promoter-primer for amplifying CHIKV nucleic acids in System 9

<400> SEQUENCE: 121
aatttaatac gactcactat agggagatct gcgtggtggg ttaccgcata cc 52

<210> SEQ ID NO 122
<211> LENGTH: 49
<212> TYPE: DNA
<213> ORGANISM: Artificial
<220> FEATURE:
<223> OTHER INFORMATION: T7 promoter-primer for amplifying CHIKV nucleic acids in System 10

<400> SEQUENCE: 122
aatttaatac gactcactat agggagagat cacaaatggt cgccggcac 49

<210> SEQ ID NO 123
<211> LENGTH: 54
<212> TYPE: DNA
<213> ORGANISM: Artificial
<220> FEATURE:
<223> OTHER INFORMATION: T7 promoter-primer for amplifying CHIKV nucleic acids in System 10

<400> SEQUENCE: 123
aatttaatac gactcactat agggagagga tgccggtcat ttgatcacaa atgg 54

<210> SEQ ID NO 124
<211> LENGTH: 48
<212> TYPE: DNA
<213> ORGANISM: Artificial
<220> FEATURE:
<223> OTHER INFORMATION: T7 promoter-primer for amplifying CHIKV nucleic acids in System 11

<400> SEQUENCE: 124
aatttaatac gactcactat agggagacaa cagcttctgt gcatcctc 48

<210> SEQ ID NO 125
<211> LENGTH: 50
<212> TYPE: DNA
<213> ORGANISM: Artificial
<220> FEATURE:
<223> OTHER INFORMATION: T7 promoter-primer for amplifying CHIKV nucleic acids in System 11

<400> SEQUENCE: 125
aatttaatac gactcactat agggagacca acagcttctg tgcatcctcc 50

<210> SEQ ID NO 126

```
<211> LENGTH: 51
<212> TYPE: DNA
<213> ORGANISM: Artificial
<220> FEATURE:
<223> OTHER INFORMATION: T7 promoter-primer for amplifying CHIKV nucleic
      acids in System 12

<400> SEQUENCE: 126
aatttaatac gactcactat agggagagct gagtccaaag tgggtaattc c          51

<210> SEQ ID NO 127
<211> LENGTH: 53
<212> TYPE: DNA
<213> ORGANISM: Artificial
<220> FEATURE:
<223> OTHER INFORMATION: T7 promoter-primer for amplifying CHIKV nucleic
      acids in System 13

<400> SEQUENCE: 127
aatttaatac gactcactat agggagagac tgggtatcag gcctcttgta gac        53

<210> SEQ ID NO 128
<211> LENGTH: 55
<212> TYPE: DNA
<213> ORGANISM: Artificial
<220> FEATURE:
<223> OTHER INFORMATION: T7 promoter-primer for amplifying CHIKV nucleic
      acids in System 14

<400> SEQUENCE: 128
aatttaatac gactcactat agggagagtg cgcattttgc cttcgtaatg caacg      55

<210> SEQ ID NO 129
<211> LENGTH: 45
<212> TYPE: DNA
<213> ORGANISM: Artificial
<220> FEATURE:
<223> OTHER INFORMATION: T7 promoter-primer for amplifying CHIKV nucleic
      acids in System 14

<400> SEQUENCE: 129
aatttaatac gactcactat agggagagtc acaggcagtg tacac                 45

<210> SEQ ID NO 130
<211> LENGTH: 54
<212> TYPE: DNA
<213> ORGANISM: Artificial
<220> FEATURE:
<223> OTHER INFORMATION: T7 promoter-primer for amplifying CHIKV nucleic
      acids in System 15

<400> SEQUENCE: 130
aatttaatac gactcactat agggagaggt agctgtagtg cgtacctatt tagg       54

<210> SEQ ID NO 131
<211> LENGTH: 20
<212> TYPE: DNA
<213> ORGANISM: Chikungunya virus

<400> SEQUENCE: 131
ctgtatcctg accacccaac                                             20

<210> SEQ ID NO 132
<211> LENGTH: 18
<212> TYPE: DNA
<213> ORGANISM: Chikungunya virus
```

```
<400> SEQUENCE: 132
gtgcctaaag caaggaac                                                    18

<210> SEQ ID NO 133
<211> LENGTH: 24
<212> TYPE: DNA
<213> ORGANISM: Chikungunya virus

<400> SEQUENCE: 133
ccaaactatc aagaagagtg ggtg                                             24

<210> SEQ ID NO 134
<211> LENGTH: 19
<212> TYPE: DNA
<213> ORGANISM: Chikungunya virus

<400> SEQUENCE: 134
cttgaatgcg cgcagatac                                                   19

<210> SEQ ID NO 135
<211> LENGTH: 24
<212> TYPE: DNA
<213> ORGANISM: Chikungunya virus

<400> SEQUENCE: 135
cacatgaagt ccgacgcttc gaag                                             24

<210> SEQ ID NO 136
<211> LENGTH: 21
<212> TYPE: DNA
<213> ORGANISM: Chikungunya virus

<400> SEQUENCE: 136
actgtgagcg cgtacgaaca c                                                21

<210> SEQ ID NO 137
<211> LENGTH: 24
<212> TYPE: DNA
<213> ORGANISM: Chikungunya virus

<400> SEQUENCE: 137
gtgcatgtgt gcacgacgca gatg                                             24

<210> SEQ ID NO 138
<211> LENGTH: 18
<212> TYPE: DNA
<213> ORGANISM: Chikungunya virus

<400> SEQUENCE: 138
cagctgtaag gtcttcac                                                    18

<210> SEQ ID NO 139
<211> LENGTH: 19
<212> TYPE: DNA
<213> ORGANISM: Chikungunya virus

<400> SEQUENCE: 139
gatgagcagg tactgaagg                                                   19

<210> SEQ ID NO 140
<211> LENGTH: 19
<212> TYPE: DNA
<213> ORGANISM: Chikungunya virus
```

```
<400> SEQUENCE: 140
gcatctgccg caggaaaag                                              19

<210> SEQ ID NO 141
<211> LENGTH: 18
<212> TYPE: DNA
<213> ORGANISM: Chikungunya virus

<400> SEQUENCE: 141
gcttcacatg ccgctgtg                                               18

<210> SEQ ID NO 142
<211> LENGTH: 23
<212> TYPE: DNA
<213> ORGANISM: Chikungunya virus

<400> SEQUENCE: 142
gtatgcggta acccaccacg cag                                         23

<210> SEQ ID NO 143
<211> LENGTH: 22
<212> TYPE: DNA
<213> ORGANISM: Chikungunya virus

<400> SEQUENCE: 143
gacacggttg acggcgaaag ag                                          22

<210> SEQ ID NO 144
<211> LENGTH: 18
<212> TYPE: DNA
<213> ORGANISM: Chikungunya virus

<400> SEQUENCE: 144
gtcattctcg gtgtgcac                                               18

<210> SEQ ID NO 145
<211> LENGTH: 20
<212> TYPE: DNA
<213> ORGANISM: Chikungunya virus

<400> SEQUENCE: 145
cagaatgtac tggcagcagc                                             20

<210> SEQ ID NO 146
<211> LENGTH: 23
<212> TYPE: DNA
<213> ORGANISM: Chikungunya virus

<400> SEQUENCE: 146
gtactggcag cagccacgaa aag                                         23

<210> SEQ ID NO 147
<211> LENGTH: 17
<212> TYPE: DNA
<213> ORGANISM: Chikungunya virus

<400> SEQUENCE: 147
acctgctgct gtctatg                                                17

<210> SEQ ID NO 148
<211> LENGTH: 19
<212> TYPE: DNA
```

<213> ORGANISM: Chikungunya virus

<400> SEQUENCE: 148
gtgcggcttc ttcaatatg                                              19

<210> SEQ ID NO 149
<211> LENGTH: 19
<212> TYPE: DNA
<213> ORGANISM: Chikungunya virus

<400> SEQUENCE: 149
catggccacc tttgcaagc                                              19

<210> SEQ ID NO 150
<211> LENGTH: 19
<212> TYPE: RNA
<213> ORGANISM: Chikungunya virus

<400> SEQUENCE: 150 ccguccuac cggaauaug                                               19

<210> SEQ ID NO 151
<211> LENGTH: 19
<212> TYPE: RNA
<213> ORGANISM: Chikungunya virus

<400> SEQUENCE: 151
cggaauaugg gagaagaac                                              19

<210> SEQ ID NO 152
<211> LENGTH: 22
<212> TYPE: RNA
<213> ORGANISM: Chikungunya virus

<400> SEQUENCE: 152
cgaggucacg uggggcaaca ac                                          22

<210> SEQ ID NO 153
<211> LENGTH: 24
<212> TYPE: RNA
<213> ORGANISM: Chikungunya virus

<400> SEQUENCE: 153
gagaaaccgg agggguacua caac                                        24

<210> SEQ ID NO 154
<211> LENGTH: 19
<212> TYPE: RNA
<213> ORGANISM: Chikungunya virus

<400> SEQUENCE: 154
guaacaguga ucccgaaca                                              19

<210> SEQ ID NO 155
<211> LENGTH: 17
<212> TYPE: DNA
<213> ORGANISM: Chikungunya virus

<400> SEQUENCE: 155
ctgacaccag gagctac                                                17

<210> SEQ ID NO 156
<211> LENGTH: 16

<212> TYPE: RNA
<213> ORGANISM: Chikungunya virus

<400> SEQUENCE: 156
cuacugcuuc ugcgac                                                        16

<210> SEQ ID NO 157
<211> LENGTH: 18
<212> TYPE: RNA
<213> ORGANISM: Chikungunya virus

<400> SEQUENCE: 157
ggauuauguu caacagac                                                      18

<210> SEQ ID NO 158
<211> LENGTH: 18
<212> TYPE: RNA
<213> ORGANISM: Chikungunya virus

<400> SEQUENCE: 158
ccuggacaga aacaucuc                                                      18

<210> SEQ ID NO 159
<211> LENGTH: 18
<212> TYPE: RNA
<213> ORGANISM: Chikungunya virus

<400> SEQUENCE: 159
gucguuaaga gaauaacg                                                      18

<210> SEQ ID NO 160
<211> LENGTH: 18
<212> TYPE: RNA
<213> ORGANISM: Chikungunya virus

<400> SEQUENCE: 160
gucauucucg gugugcac                                                      18

<210> SEQ ID NO 161
<211> LENGTH: 19
<212> TYPE: RNA
<213> ORGANISM: Chikungunya virus

<400> SEQUENCE: 161
ccauuuguga ucaaaugac                                                     19

<210> SEQ ID NO 162
<211> LENGTH: 19
<212> TYPE: RNA
<213> ORGANISM: Chikungunya virus

<400> SEQUENCE: 162
cugcaacguc acacagaug                                                     19

<210> SEQ ID NO 163
<211> LENGTH: 18
<212> TYPE: RNA
<213> ORGANISM: Chikungunya virus

<400> SEQUENCE: 163
gaagcagaaa acacacac                                                      18

<210> SEQ ID NO 164

```
<211> LENGTH: 20
<212> TYPE: RNA
<213> ORGANISM: Chikungunya virus

<400> SEQUENCE: 164
acaucugcac ccaaguguac                                                    20

<210> SEQ ID NO 165
<211> LENGTH: 20
<212> TYPE: RNA
<213> ORGANISM: Chikungunya virus

<400> SEQUENCE: 165
agaagcucag aggacccguc                                                    20

<210> SEQ ID NO 166
<211> LENGTH: 28
<212> TYPE: RNA
<213> ORGANISM: Chikungunya virus

<400> SEQUENCE: 166
cagacuugua cgcggaauuc ggcgcugg                                           28

<210> SEQ ID NO 167
<211> LENGTH: 51
<212> TYPE: RNA
<213> ORGANISM: Chikungunya virus
<220> FEATURE:
<221> NAME/KEY: misc_feature
<222> LOCATION: (46)..(46)
<223> OTHER INFORMATION: n is a, c, g, or u
<220> FEATURE:
<221> NAME/KEY: misc_feature
<222> LOCATION: (49)..(49)
<223> OTHER INFORMATION: n is a, c, g, or u

<400> SEQUENCE: 167
ggauacaacu gcaucuauga ucuucacuuc cauguucauc caagungcnc a                 51

<210> SEQ ID NO 168
<211> LENGTH: 48
<212> TYPE: RNA
<213> ORGANISM: Chikungunya virus

<400> SEQUENCE: 168
gcaaacgccu cgucuacgua caacacgucg acuggucugu ugcaucca                    48

<210> SEQ ID NO 169
<211> LENGTH: 46
<212> TYPE: RNA
<213> ORGANISM: Chikungunya virus
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: misc_feature
<222> LOCATION: (6)..(7)
<223> OTHER INFORMATION: n is a, c, g, or u
<220> FEATURE:
<221> NAME/KEY: misc_feature
<222> LOCATION: (10)..(10)
<223> OTHER INFORMATION: n is a, c, g, or u
<220> FEATURE:
<221> NAME/KEY: misc_feature
<222> LOCATION: (46)..(46)
<223> OTHER INFORMATION: n is a, c, g, or u

<400> SEQUENCE: 169
```
agunannuun uuuccuuggu aaaggacgcg gagcuuagcu gaugcn         46

<210> SEQ ID NO 170
<211> LENGTH: 19
<212> TYPE: DNA
<213> ORGANISM: Chikungunya virus

<400> SEQUENCE: 170
cttcaatatg atgcagatg                                       19

<210> SEQ ID NO 171
<211> LENGTH: 19
<212> TYPE: DNA
<213> ORGANISM: Chikungunya virus

<400> SEQUENCE: 171
gatgcagatg aaagtcaac                                       19

<210> SEQ ID NO 172
<211> LENGTH: 19
<212> TYPE: DNA
<213> ORGANISM: Chikungunya virus

<400> SEQUENCE: 172
cagtgcggct tcttcaata                                       19

<210> SEQ ID NO 173
<211> LENGTH: 19
<212> TYPE: DNA
<213> ORGANISM: Chikungunya virus

<400> SEQUENCE: 173
ggcttcttca atatgatgc                                       19

<210> SEQ ID NO 174
<211> LENGTH: 20
<212> TYPE: DNA
<213> ORGANISM: Chikungunya virus

<400> SEQUENCE: 174
acatctgcac ccaagtgtac                                      20

<210> SEQ ID NO 175
<211> LENGTH: 17
<212> TYPE: DNA
<213> ORGANISM: Chikungunya virus

<400> SEQUENCE: 175
tgcacccaag tgtacca                                         17

<210> SEQ ID NO 176
<211> LENGTH: 17
<212> TYPE: DNA
<213> ORGANISM: Chikungunya virus

<400> SEQUENCE: 176
aacatctgca cccaagt                                         17

<210> SEQ ID NO 177
<211> LENGTH: 29
<212> TYPE: DNA
<213> ORGANISM: Chikungunya virus

```
<400> SEQUENCE: 177
agtgcgcatt ttgccttcgt aatgcaacg                                29

<210> SEQ ID NO 178
<211> LENGTH: 18
<212> TYPE: DNA
<213> ORGANISM: Chikungunya virus

<400> SEQUENCE: 178
ccgcctggag atactttt                                            18

<210> SEQ ID NO 179
<211> LENGTH: 19
<212> TYPE: DNA
<213> ORGANISM: Chikungunya virus

<400> SEQUENCE: 179
accgcctgga gatactttt                                           19

<210> SEQ ID NO 180
<211> LENGTH: 21
<212> TYPE: DNA
<213> ORGANISM: Chikungunya virus

<400> SEQUENCE: 180
agaccgcctg gagatacttt t                                        21

<210> SEQ ID NO 181
<211> LENGTH: 23
<212> TYPE: DNA
<213> ORGANISM: Chikungunya virus

<400> SEQUENCE: 181
ggagaccgcc tggagatact ttt                                      23

<210> SEQ ID NO 182
<211> LENGTH: 45
<212> TYPE: DNA
<213> ORGANISM: Artificial
<220> FEATURE:
<223> OTHER INFORMATION: T7 promoter-primer for amplifying CHIKV nucleic
      acids in System 14

<400> SEQUENCE: 182
aatttaatac gactcactat agggagaccg cctggagata ctttt              45

<210> SEQ ID NO 183
<211> LENGTH: 17
<212> TYPE: RNA
<213> ORGANISM: Chikungunya virus

<400> SEQUENCE: 183
ccugugacyg ccauugu                                             17

<210> SEQ ID NO 184
<211> LENGTH: 17
<212> TYPE: RNA
<213> ORGANISM: Chikungunya virus

<400> SEQUENCE: 184
ccugugacug ccauugu                                             17

<210> SEQ ID NO 185
```

```
<211> LENGTH: 17
<212> TYPE: RNA
<213> ORGANISM: Chikungunya virus

<400> SEQUENCE: 185
ccugugaccg ccauugu                                                  17

<210> SEQ ID NO 186
<211> LENGTH: 87
<212> TYPE: DNA
<213> ORGANISM: Chikungunya virus
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t

<400> SEQUENCE: 186
acccgaagca gtgcggcttc ttcaatatga tgcagatgaa agtcaactan aatcanaaca   60
tctgcaccca agtgtaccac aaaagta                                       87

<210> SEQ ID NO 187
<211> LENGTH: 47
<212> TYPE: DNA
<213> ORGANISM: Chikungunya virus

<400> SEQUENCE: 187
acccgaagca gtgcggcttc ttcaatatga tgcagatgaa agtcaac                 47

<210> SEQ ID NO 188
<211> LENGTH: 28
<212> TYPE: RNA
<213> ORGANISM: Chikungunya virus

<400> SEQUENCE: 188
cagacuugua cgcggaauuc ggcgcugg                                      28

<210> SEQ ID NO 189
<211> LENGTH: 31
<212> TYPE: RNA
<213> ORGANISM: Chikungunya virus

<400> SEQUENCE: 189
gcaucuauga ucuucacuuc cauguucauc c                                  31

<210> SEQ ID NO 190
<211> LENGTH: 28
<212> TYPE: RNA
<213> ORGANISM: Chikungunya virus

<400> SEQUENCE: 190
cgucuacgua caacacgucg acuggucu                                      28

<210> SEQ ID NO 191
<211> LENGTH: 26
<212> TYPE: RNA
<213> ORGANISM: Chikungunya virus

<400> SEQUENCE: 191
uuuccuuggu aaaggacgcg gagcuu                                        26
```

US 10,344,341 B2

METHOD FOR DETECTING CHIKUNGUNYA VIRUS

CROSS-REFERENCE TO RELATED APPLICATIONS

This application is a continuation of 12/386,832, filed Apr. 21, 2009, now U.S. Pat. No. 9,273,365, which claims the benefit of U.S. Provisional Application No. 61/046,734, filed Apr. 21, 2008, each of which is hereby incorporated by reference in its entirety.

FIELD

The present invention relates to the field of biotechnology. More specifically, the invention relates to diagnostic assays for detecting the nucleic acids of Chikungunya virus.

BACKGROUND

First described during an outbreak in southern Tanzania in 1952, Chikungunya fever is a viral disease spread by mosquitos. Symptoms of the disease include fever and severe joint pain, often accompanied by muscle pain, headache, nausea, fatigue and rash. The name of the disease derives from a verb in the Kimakonde language, meaning "to become contorted"—a reference to the appearance of suffers afflicted with debilitating joint pain. In some instances, the joint pain may persist for several months, or even years. Treatment of the disease focuses on relieving symptoms, as there is no cure. (See WHO Fact sheet No. 327, March 2008).

The virus is transmitted from one human to another by the bites of infected female mosquitos. The most common vectors are *Aedes aegypti* and *Aedes albopictus*—two vectors which also transmit other mosquito-borne viruses, including dengue. The Asian tiger mosquito (*Aedes albopictus*) has also been shown to be an efficient vector for transmission of Chikungunya fever. This latter spec between people. Nonetheless, the insect-based mode of transmission is highly efficient, as evidenced by the infection of nearly 40% of the population of 785,000 individuals during a massive outbreak on La Reunion island in 2005 and 2006. (See WHO Fact sheet No. 327 (March 2008); *Science* 318:1860-61 (December 2007); and "Information on *Aedes albopictus*" CDC, Division of Vector-Borne Infectious Diseases).

Chikungunya virus is classified under the Genus Alphavirus, in the Family Togaviridae. Generally speaking, the alphaviruses are enveloped particles containing a genome that consists of a single-stranded, positive-sense RNA molecule of approximately 12 kb The 5'-end is capped with a 7-methylguanosine while the 3'-end is polyadenylated. Nonstructural proteins are translated directly from the 5' two-thirds of the genomic RNA. A subgenomic positive-strand RNA referred to as 26S RNA, identical to the 3' one third of the genomic RNA, is transcribed from the negative-stranded RNA intermediate. This latter RNA serves as the mRNA for the synthesis of viral structural proteins. (*J. Gen Virol* 83:3075-84 (2002)).

SUMMARY

One aspect of the invention relates to a method for determining whether a Chikungunya virus (CHIKV) nucleic acid sequence is present in a test sample that includes nucleic acids. First there is a step for contacting nucleic acids of the test sample with a set of amplification oligonucleotides. A first member of the oligonucleotide set is up to 100 bases in length and complementary to at least 15 contiguous bases contained within SEQ ID NO:14. A second member of the oligonucleotide set is up to 100 bases in length and complementary to at least 15 contiguous bases of an extension product of the first member of the oligonucleotide set when a polynucleotide consisting of SEQ ID NO:14 is the template in a template-dependent primer extension reaction. Next, there is a step for performing an in vitro nucleic acid amplification reaction using nucleic acids of the test sample as templates together with the set of amplification oligonucleotides. If the test sample included the CHIKV nucleic acid sequence, then there is produced an amplification product. Finally, the invented method includes a step for detecting any of the amplification product that may have been produced in the in vitro nucleic acid amplification reaction. If the amplification product is detected in an amount greater than a cutoff value, this indicates that the CHIKV nucleic acid sequence is present in the test sample. Alternatively, if the amplification product is detected in an amount less than the cutoff value, this indicates that the CHIKV nucleic acid sequence is absent from the test sample. In a preferred embodiment, the amplification product detected in the method is a single-stranded nucleic acid including 17 contiguous bases of one member of the set of amplification oligonucleotides, and further including the complement of 17 contiguous bases of the other member of the set of amplification oligonucleotides. In a different preferred embodiment, the first amplification oligonucleotide is up to 55 bases in length, and the second amplification oligonucleotide includes 19 contiguous bases of SEQ ID NO:68. In one highly preferred embodiment, the 3' terminal sequence of the first amplification oligonucleotide is SEQ ID NO:108. In another preferred embodiment, the second amplification oligonucleotide is selected from the group consisting of SEQ ID NO:148, SEQ ID NO:170, SEQ ID NO:172 and SEQ ID NO:173. In yet another preferred embodiment, the detecting step involves detecting the amplification product using a hybridization probe. In such a case, the hybridization probe can be any of SEQ ID NO:164, SEQ ID NO:184 and SEQ ID NO:185. In still yet another preferred embodiment, the detecting step involves detecting the amplification product using a hybridization probe, and the probability of detecting the amplification product in the amount greater than the cutoff value is at least 95% when the concentration of the CHIKV nucleic acid sequence in the test sample is in the range of from 26 copies/ml to about 3,400 copies/ml. In still yet another preferred embodiment, the detecting step involves detecting the amplification product using a hybridization probe, and the probability of detecting the amplification product in the amount greater than the cutoff value is at least 95% when the concentration of the CHIKV nucleic acid sequence in the test sample is in the range of from 26 copies/ml to about 200 copies/ml. In even still yet another preferred embodiment, the detecting step involves detecting the amplification product using a hybridization probe, and the probability of detecting the amplification product in the amount greater than the cutoff value is at least 95% only when the concentration of the CHIKV nucleic acid sequence in the test sample is between about 100 copies/ml and 3,400 copies/ml. In a general embodiment of the invented method, the 3' terminal base sequence of first amplification oligonucleotide is SEQ ID NO:108; the detecting step involves detecting the amplification product using a hybridization probe; and the probability of detecting the amplification product in the amount greater than the cutoff value is at least 95% when the concentration of the CHIKV nucleic acid sequence in the test sample is in the range of from 26 copies/ml to about 200 copies/ml. When this is the case, the first amplification primer may include a phage T7 promoter sequence located upstream of SEQ ID NO:108. In another preferred embodiment, the second amplification oligonucleotide includes either 19 contiguous bases of SEQ ID NO:68, or 17 contiguous bases of SEQ ID NO:84. In still another preferred embodiment, the second amplification oligonucleotide is any of SEQ ID NO:148, SEQ ID NO:174 and SEQ ID NO:176. In yet another preferred embodiment, the hybridization probe is SEQ ID NO:164. In still yet another embodiment, the hybridization probe is SEQ ID NO:183. In another general embodiment of the invented method, the first amplification oligonucleotide is up to 55 bases in length, and the second amplification oligonucleotide includes 17 contiguous bases of SEQ ID NO:84. When this is the case, the second amplification oligonucleotide may be any of SEQ ID NO:174, SEQ ID NO:175 and SEQ ID NO:176. In another general embodiment of the invented method, the second member of the set of amplification oligonucleotides includes 17-20 contiguous bases contained within the sequence of SEQ ID NO:186. More preferably, the second member of the set of amplification oligonucleotides is any of SEQ ID NO:148, SEQ ID NO:170, SEQ ID NO:171, SEQ ID NO:172, SEQ ID NO:173, SEQ ID NO:174, SEQ ID NO:175 and SEQ ID NO:176. In another general embodiment of the invented method, the first member of the set of amplification oligonucleotides hybridizes to a polynucleotide consisting of SEQ ID NO:14 under stringent conditions of 42° C. when the salt concentration is in the range of 0.6-0.9 M, and wherein the second member of the set of amplification oligonucleotides hybridizes to the extension product under the same stringent conditions. In another general embodiment of the invented method, the cutoff value is determined by a statistical analysis of results obtained for (i) a plurality of amplification reactions performed using known concentrations of the CHIKV nucleic acid sequence, and (ii) a plurality of negative control amplification reactions performed in the absence of the CHIKV nucleic acid sequence. In another general embodiment of the invented method, the cutoff value is determined by a statistical analysis using average hybridization signal readings of negative control reactions that do not include the CHIKV nucleic acid sequence plus three standard deviations of the negative control reactions that do not include the CHIKV nucleic acid sequence.

Another aspect of the invention relates to a kit (i.e., a packaged combination) for amplifying and detecting a Chikungunya virus (CHIKV) nucleic acid sequence. The kit includes a first primer up to 100 bases long and including a target-complementary 3' terminal sequence of 15-48 contiguous bases of SEQ ID NO:48. The target-complementary 3' terminal sequence of this first primer is fully contained within the sequence of SEQ ID NO:48. The first primer optionally may include a first primer 5' sequence (i.e., an upstream sequence) that is not complementary to CHIKV nucleic acids. The kit also includes a second primer up to 100 bases long and including a target-complementary 3' terminal sequence of 15-47 contiguous bases of SEQ ID NO:186. The target-complementary 3' terminal sequence of the second primer is fully contained within the sequence of SEQ ID NO:186. The second primer optionally may include a second primer 5' sequence (i.e., an upstream sequence) that is not complementary to CHIKV nucleic acids. Generally, the kit further includes a hybridization probe for detecting a nucleic acid amplification product synthesized using the primers. In a preferred embodiment, the target-complementary 3' terminal sequence of the second primer is either: (i) 15-47 bases in length and fully contained within the sequence of SEQ ID NO:187; (ii) 15-39 bases in length and fully contained within the sequence of SEQ ID NO:68; or (iii) 15-40 bases in length and fully contained within the sequence of SEQ ID NO:84. In another preferred embodiment, the hybridization probe is up to 40 bases in length and includes 15-40 contiguous bases of SEQ ID NO:84. In a different preferred embodiment, the target-complementary 3' terminal sequence of the first primer is SEQ ID NO:108. More preferably, the target-complementary 3' terminal sequence of the second primer can be fully contained within the sequence of SEQ ID NO:187. When this is the case, the hybridization probe can be up to 40 bases in length and include 15-40 contiguous bases of SEQ ID NO:84. Alternatively, the target-complementary 3' terminal sequence of the second primer can be fully contained within the sequence of SEQ ID NO:68. Under still a different alternative, the target-complementary 3' terminal sequence of the second primer can be any of SEQ ID NO:148, SEQ ID NO:170, SEQ ID NO:171, SEQ ID NO:172 and SEQ ID NO:173. More preferably, the hybridization probe consists of SEQ ID NO:164. In accordance with another generally preferred embodiment, when the target-complementary 3' terminal sequence of the first primer is SEQ ID NO:108, the first primer includes the optional first primer 5' sequence, which includes a phage T7 promoter sequence. In a different preferred embodiment, when the target-complementary 3' terminal sequence of the first primer is SEQ ID NO:108, the target-complementary 3' terminal sequence of the second primer is fully contained within the sequence of SEQ ID NO:84. More preferably, the target-complementary 3' terminal sequence of the second primer is any of SEQ ID NO:174, SEQ ID NO:175 and SEQ ID NO:176. Still more preferably, the hybridization probe is any of SEQ ID NO:184 and SEQ ID NO:185. In accordance with a general embodiment of the invented kit, the target-complementary 3' terminal sequence of the second primer is fully contained within SEQ ID NO:68. In accordance with another general embodiment of the invented kit, the target-complementary 3' terminal sequence of the second primer is fully contained within SEQ ID NO:84. In accordance with yet another general embodiment of the invented kit, there is further included a third primer up to 100 bases long and including a target-complementary 3' terminal sequence of 15-47 contiguous bases of SEQ ID NO:186. The target-complementary 3' terminal sequence of the third primer can be fully contained within the sequence of SEQ ID NO:186. As well, the third primer optionally may include a third primer 5' sequence that is not complementary to CHIKV nucleic acids. Significantly, the third primer is different from the second primer in the kit. More preferably, each of the second and third primers that are different from each other include target-complementary 3' terminal sequences of 15-47 contiguous bases of SEQ ID NO:187. When this is the case, the target-complementary 3' terminal sequence of the second primer can be SEQ ID NO:148. More preferably, the target-complementary 3' terminal sequence of the third primer is any of SEQ ID NO:170, SEQ ID NO:171, SEQ ID NO:172, SEQ ID NO:173. As an alternative to including second and third primers having a sequence of contiguous bases fount in SEQ ID NO:187, each of the second and third primers may include target-complementary 3' terminal sequences that are 15-40 contiguous bases of SEQ ID NO:84.

Another aspect of the invention relates to a kit (i.e., a packaged combination) for amplifying and detecting a Chikungunya virus (CHIKV) nucleic acid sequence. Generally, the kit includes a first primer up to 100 bases long and including a target-complementary 3' terminal sequence of 15-44 contiguous bases of SEQ ID NO:46. The target-complementary 3' terminal sequence of the first primer can be fully contained within the sequence of SEQ ID NO:46. The first primer optionally may include a first primer 5' sequence that is not complementary to CHIKV nucleic acids. The kit further includes a second primer up to 100 bases long and including a target-complementary 3' terminal sequence of 15-40 contiguous bases of SEQ ID NO:65. The target-complementary 3' terminal sequence of the second primer can be fully contained within the sequence of SEQ ID NO:65. The second primer optionally may include a second primer 5' sequence that is not complementary to CHIKV nucleic acids. The kit further includes a third primer up to 100 bases long and including a target-complementary 3' terminal sequence of 15-43 contiguous bases of SEQ ID NO:66. The target-complementary 3' terminal sequence of the third primer can be fully contained within the sequence of SEQ ID NO:66. The third primer optionally may include a third primer 5' sequence that is not complementary to CHIKV nucleic acids. Finally, the kit further includes a hybridization probe for detecting a nucleic acid amplification product synthesized using the primers. In a preferred embodiment, the target-complementary 3' terminal sequence of the first primer is SEQ ID NO:106. In another preferred embodiment, the target-complementary 3' terminal sequence of the second primer is SEQ ID NO:145. In yet another preferred embodiment, the target-complementary 3' terminal sequence of the third primer is SEQ ID NO:146. In still yet another preferred embodiment, the hybridization probe is up to 39 bases in length and includes 15-39 contiguous bases of SEQ ID NO:82. For example, the hybridization probe may include SEQ ID NO:162.

Another aspect of the invention relates to a method for determining whether a Chikungunya virus (CHIKV) nucleic acid sequence is present in a test sample that includes nucleic acids. According to the method, first there is a step for contacting nucleic acids of the test sample with a set of amplification oligonucleotides that includes three primers. There is a first primer up to 100 bases long and including a target-complementary 3' terminal sequence of 15-44 contiguous bases of SEQ ID NO:46. The target-complementary 3' terminal sequence of the first primer is fully contained within the sequence of SEQ ID NO:46. The first primer optionally includes a first primer 5' sequence that is not complementary to CHIKV nucleic acids. The oligonucleotide set further includes a second primer up to 100 bases long and including a target-complementary 3' terminal sequence of 15-40 contiguous bases of SEQ ID NO:65. The target-complementary 3' terminal sequence of the second primer is fully contained within the sequence of SEQ ID NO:65. The second primer optionally includes a second primer 5' sequence that is not complementary to CHIKV nucleic acids. Finally, there is a third primer up to 100 bases long and including a target-complementary 3' terminal sequence of 15-43 contiguous bases of SEQ ID NO:66. The target-complementary 3' terminal sequence of the third primer is fully contained within the sequence of SEQ ID NO:66. The third primer optionally includes a third primer 5' sequence that is not complementary to CHIKV nucleic acids. Next, there is a step for performing an in vitro nucleic acid amplification reaction using nucleic acids of the test sample as templates together with the set of amplification oligonucleotides. If the test sample included the CHIKV nucleic acid sequence, then there is produced an amplification product. Finally, the invented method includes a step for detecting with a hybridization probe any of the amplification product that may have been produced in the in vitro nucleic acid amplification reaction. If the amplification product is detected in an amount greater than a cutoff value, this indicates that the CHIKV nucleic acid sequence is present in the test sample. Alternatively, if the amplification product is detected in an amount less than the cutoff value, this indicates that the CHIKV nucleic acid sequence is absent from the test sample.

Another aspect of the invention relates to a kit (i.e., a packaged combination) for amplifying and detecting a Chikungunya virus (CHIKV) nucleic acid sequence. Generally, the kit includes a first primer up to 100 bases long and including a target-complementary 3' terminal sequence consisting of 15-47 contiguous bases of SEQ ID NO:50. The target-complementary 3' terminal sequence of the first primer can be fully contained within the sequence of SEQ ID NO:50. The first primer optionally includes a first primer 5' sequence that is not complementary to CHIKV nucleic acids. The kit further includes a second primer up to 100 bases long and including a target-complementary 3' terminal sequence of 15-39 contiguous bases of SEQ ID NO:69. The target-complementary 3' terminal sequence of the second primer is fully contained within the sequence of SEQ ID NO:69. The second primer optionally may include a second primer 5' sequence that is not complementary to CHIKV nucleic acids. Finally, the kit further includes a hybridization probe for detecting a nucleic acid amplification product synthesized using the primers. In a preferred embodiment, the target-complementary 3' terminal sequence of the of the first primer is SEQ ID NO:110. In another preferred embodiment, the target-complementary 3' terminal sequence of the second primer is SEQ ID NO:149. In still yet another preferred embodiment, the hybridization probe is up to 40 bases in length and includes 15-40 contiguous bases of SEQ ID NO:85. For example, the hybridization probe can include SEQ ID NO:165.

Another aspect of the invention relates to a method for determining whether a Chikungunya virus (CHIKV) nucleic acid sequence is present in a test sample that includes nucleic acids. According to the method, first there is a step for contacting nucleic acids of the test sample with a set of amplification oligonucleotides that includes two primers. There is a first primer up to 100 bases long and including a target-complementary 3' terminal sequence consisting of 15-47 contiguous bases of SEQ ID NO:50. The target-complementary 3' terminal sequence of the first primer can be fully contained within the sequence of SEQ ID NO:50. The first primer optionally may include a first primer 5' sequence that is not complementary to CHIKV nucleic acids. The oligonucleotide set further includes a second primer up to 100 bases long and including a target-complementary 3' terminal sequence consisting of 15-39 contiguous bases of SEQ ID NO:69. The target-complementary 3' terminal sequence of the second primer can be fully contained within the sequence of SEQ ID NO:69. The second primer optionally may include a second primer 5' sequence that is not complementary to CHIKV nucleic acids. Next, there is a step for performing an in vitro nucleic acid amplification reaction using nucleic acids of the test sample as templates together with the set of amplification oligonucleotides. If the test sample included the CHIKV nucleic acid sequence, then there is produced an amplification product. Finally, the invented method includes a step for detecting with a hybridization probe any of the amplification product that may have been produced in the in vitro nucleic acid amplification reaction. If the amplification product is detected in an amount greater than a cutoff value, this indicates that the CHIKV nucleic acid sequence is present in the test sample. Alternatively, if the amplification product is detected in an amount less than the cutoff value, this indicates that the CHIKV nucleic acid sequence is absent from the test sample.

Another aspect of the invention relates to a kit (i.e., a packaged combination) for amplifying and detecting a Chikungunya virus (CHIKV) nucleic acid sequence. Generally, the kit includes a first primer up to 100 bases long and including a target-complementary 3' terminal sequence consisting of 15-44 contiguous bases of SEQ ID NO:31. The target-complementary 3' terminal sequence of the first primer can be fully contained within the sequence of SEQ ID NO:31. The first primer optionally may include a first primer 5' sequence that is not complementary to CHIKV nucleic acids. The kit further includes a second primer up to 100 bases long and including a target-complementary 3' terminal sequence of 15-40 contiguous bases of SEQ ID NO:51. The target-complementary 3' terminal sequence of the second primer can be fully contained within the sequence of SEQ ID NO:51. The second primer optionally may include a second primer 5' sequence that is not complementary to CHIKV nucleic acids. The kit further includes a third primer up to 100 bases long and including a target-complementary 3' terminal sequence of 15-38 contiguous bases of SEQ ID NO:52. The target-complementary 3' terminal sequence of the third primer can be fully contained within the sequence of SEQ ID NO:52. The third primer optionally may include a third primer 5' sequence that is not complementary to CHIKV nucleic acids. Finally, the kit further includes a hybridization probe composition for detecting a nucleic acid amplification product synthesized using the primers. In a preferred embodiment, the target-complementary 3' terminal sequence of the first primer is SEQ ID NO:91. In another preferred embodiment, the target-complementary 3' terminal sequence of the second primer is SEQ ID NO:131. In yet another preferred embodiment, the target-complementary 3' terminal sequence of the third primer is SEQ ID NO:132. In still yet another preferred embodiment, the hybridization probe composition includes a first hybridization probe up to 39 bases in length and including 15-39 contiguous bases of SEQ ID NO:70, and a second hybridization probe up to 39 bases in length and including 15-39 contiguous bases of SEQ ID NO:71. For example, the first hybridization probe can include SEQ ID NO:150, and the second hybridization probe can include SEQ ID NO:151.

Another aspect of the invention relates to a method for determining whether a Chikungunya virus (CHIKV) nucleic acid sequence is present in a test sample that includes nucleic acids. According to the method, first there is a step for contacting nucleic acids of the test sample with a set of amplification oligonucleotides that includes three primers. There is a first primer up to 100 bases long and including a target-complementary 3' terminal sequence of 15-44 contiguous bases of SEQ ID NO:31. The target-complementary 3' terminal sequence of the first primer can be fully contained within the sequence of SEQ ID NO:31. The first primer optionally may include a first primer 5' sequence that is not complementary to CHIKV nucleic acids. The oligonucleotide set further includes a second primer up to 100 bases long and including a target-complementary 3' terminal sequence of 15-40 contiguous bases of SEQ ID NO:51. The target-complementary 3' terminal sequence of the second primer can be fully contained within the sequence of SEQ ID NO:51. The second primer optionally may include a second primer 5' sequence that is not complementary to CHIKV nucleic acids. Finally, there is a third primer up to 100 bases long and including a target-complementary 3' terminal sequence of 15-38 contiguous bases of SEQ ID NO:52. The target-complementary 3' terminal sequence of the third primer can be fully contained within the sequence of SEQ ID NO:52. The third primer optionally may include a third primer 5' sequence that is not complementary to CHIKV nucleic acids. Next, there is a step for performing an in vitro nucleic acid amplification reaction using nucleic acids of the test sample as templates together with the set of amplification oligonucleotides. If the test sample included the CHIKV nucleic acid sequence, then there is produced an amplification product. Finally, the invented method includes a step for detecting with a hybridization probe any of the amplification product that may have been produced in the in vitro nucleic acid amplification reaction. If the amplification product is detected in an amount greater than a cutoff value, this indicates that the CHIKV nucleic acid sequence is present in the test sample. Alternatively, if the amplification product is detected in an amount less than the cutoff value, this indicates that the CHIKV nucleic acid sequence is absent from the test sample.

Another aspect of the invention relates to a kit (i.e., a packaged combination) for amplifying and detecting a Chikungunya virus (CHIKV) nucleic acid sequence. Generally, the kit includes a first primer up to 100 bases long and including a target-complementary 3' terminal sequence of 15-46 contiguous bases of SEQ ID NO:32. The target-complementary 3' terminal sequence of the first primer can be fully contained within the sequence of SEQ ID NO:32. The first primer optionally may include a first primer 5' sequence that is not complementary to CHIKV nucleic acids. The kit further includes a second primer up to 100 bases long and including a target-complementary 3' terminal sequence of 15-44 contiguous bases of SEQ ID NO:53. The target-complementary 3' terminal sequence of the second primer can be fully contained within the sequence of SEQ ID NO:53. The second primer optionally may include a second primer 5' sequence that is not complementary to CHIKV nucleic acids. Finally, the kit further includes a hybridization probe for detecting a nucleic acid amplification product synthesized using the primers. In a preferred embodiment, the target-complementary 3' terminal sequence of the first primer is SEQ ID NO:92. In another preferred embodiment, the target-complementary 3' terminal sequence of the second primer is SEQ ID NO:133. In still yet another preferred embodiment, the hybridization probe is up to 42 bases in length and includes 15-42 contiguous bases of SEQ ID NO:72. For example, the hybridization probe can include SEQ ID NO:152.

Another aspect of the invention relates to a method for determining whether a Chikungunya virus (CHIKV) nucleic acid sequence is present in a test sample that includes nucleic acids. According to the method, first there is a step for contacting nucleic acids of the test sample with a set of amplification oligonucleotides that includes two primers. There is a first primer up to 100 bases long and including a target-complementary 3' terminal sequence of 15-46 contiguous bases of SEQ ID NO:32. The target-complementary 3' terminal sequence of the first primer can be fully contained within the sequence of SEQ ID NO:32. The first primer optionally may include a first primer 5' sequence that is not complementary to CHIKV nucleic acids. The oligonucleotide set further includes a second primer up to 100 bases long and including a target-complementary 3' terminal sequence of 15-44 contiguous bases of SEQ ID NO:53. The target-complementary 3' terminal sequence of the second primer can be fully contained within the sequence of SEQ ID NO:53. The second primer optionally may include a second primer 5' sequence that is not complementary to CHIKV nucleic acids. Next, there is a step for performing an in vitro nucleic acid amplification reaction using nucleic acids of the test sample as templates together with the set of amplification oligonucleotides. If the test sample included the CHIKV nucleic acid sequence, then there is produced an amplification product. Finally, the invented method includes a step for detecting with a hybridization probe any of the amplification product that may have been produced in the in vitro nucleic acid amplification reaction. If the amplification product is detected in an amount greater than a cutoff value, this indicates that the CHIKV nucleic acid sequence is present in the test sample. Alternatively, if the amplification product is detected in an amount less than the cutoff value, this indicates that the CHIKV nucleic acid sequence is absent from the test sample.

Another aspect of the invention relates to a kit (i.e., a packaged combination) for amplifying and detecting a Chikungunya virus (CHIKV) nucleic acid sequence. Generally, the kit includes a first primer up to 100 bases long and including a target-complementary 3' terminal sequence of 15-51 contiguous bases of SEQ ID NO:36. The target-complementary 3' terminal sequence of the first primer can be fully contained within the sequence of SEQ ID NO:36. The first primer optionally may include a first primer 5' sequence that is not complementary to CHIKV nucleic acids. The kit further includes a second primer up to 100 bases long and including a target-complementary 3' terminal sequence of 15-44 contiguous bases of SEQ ID NO:57. The target-complementary 3' terminal sequence of the second primer can be fully contained within the sequence of SEQ ID NO:57. The second primer optionally may include a second primer 5' sequence that is not complementary to CHIKV nucleic acids. The kit further includes a hybridization probe for detecting a nucleic acid amplification product synthesized using the primers. In a preferred embodiment, the target-complementary 3' terminal sequence of the first primer is SEQ ID NO:96. In another preferred embodiment, the target-complementary 3' terminal sequence of the second primer is SEQ ID NO:137. In still yet another preferred embodiment, the hybridization probe is up to 37 bases in length and includes 15-37 contiguous bases of SEQ ID NO:75. For example, the hybridization probe can include SEQ ID NO:155.

Another aspect of the invention relates to a method for determining whether a Chikungunya virus (CHIKV) nucleic acid sequence is present in a test sample that includes nucleic acids. According to the method, first there is a step for contacting nucleic acids of the test sample with a set of amplification oligonucleotides that includes two primers. There is a first primer up to 100 bases long and including a target-complementary 3' terminal sequence consisting of 15-51 contiguous bases of SEQ ID NO:36. The target-complementary 3' terminal sequence of the first primer can be fully contained within the sequence of SEQ ID NO:36. The first primer optionally may include a first primer 5' sequence that is not complementary to CHIKV nucleic acids. The kit further includes a second primer up to 100 bases long and including a target-complementary 3' terminal sequence of 15-44 contiguous bases of SEQ ID NO:57. The target-complementary 3' terminal sequence of the second primer can be fully contained within the sequence of SEQ ID NO:57. The second primer optionally may include a second primer 5' sequence that is not complementary to CHIKV nucleic acids. Next, there is a step for performing an in vitro nucleic acid amplification reaction using nucleic acids of the test sample as templates together with the set of amplification oligonucleotides. If the test sample included the CHIKV nucleic acid sequence, then there is produced an amplification product. Finally, the invented method includes a step for detecting with a hybridization probe any of the amplification product that may have been produced in the in vitro nucleic acid amplification reaction. If the amplification product is detected in an amount greater than a cutoff value, this indicates that the CHIKV nucleic acid sequence is present in the test sample. Alternatively, if the amplification product is detected in an amount less than the cutoff value, this indicates that the CHIKV nucleic acid sequence is absent from the test sample.

Another aspect of the invention relates to a kit (i.e., a packaged combination) for amplifying and detecting a Chikungunya virus (CHIKV) nucleic acid sequence. Generally, the kit includes a first primer up to 100 bases long and including a target-complementary 3' terminal sequence of 15-37 contiguous bases of SEQ ID NO:37. The target-complementary 3' terminal sequence of the first primer can be fully contained within the sequence of SEQ ID NO:37. The first primer optionally may include a first primer 5' sequence that is not complementary to CHIKV nucleic acids. The kit further includes a second primer up to 100 bases long and including a target-complementary 3' terminal sequence of 15-38 contiguous bases of SEQ ID NO:58. The target-complementary 3' terminal sequence of the second primer can be fully contained within the sequence of SEQ ID NO:58. The second primer optionally may include a second primer 5' sequence that is not complementary to CHIKV nucleic acids. The kit further includes a hybridization probe for detecting a nucleic acid amplification product synthesized using the primers. In a preferred embodiment, the target-complementary 3' terminal sequence of the first primer is SEQ ID NO:97. In another preferred embodiment, the target-complementary 3' terminal sequence of the second primer is SEQ ID NO:138. In still yet another preferred embodiment, the hybridization probe is up to 44 bases in length and includes 15-44 contiguous bases of SEQ ID NO:76. For example, the hybridization probe can include SEQ ID NO:156.

Another aspect of the invention relates to a method for determining whether a Chikungunya virus (CHIKV) nucleic acid sequence is present in a test sample that includes nucleic acids. According to the method, first there is a step for contacting nucleic acids of the test sample with a set of amplification oligonucleotides that includes two primers. There is a first primer up to 100 bases long and including a target-complementary 3' terminal sequence of 15-37 contiguous bases of SEQ ID NO:37. The target-complementary 3' terminal sequence of the first primer can be fully contained within the sequence of SEQ ID NO:37. The first primer optionally may include a first primer 5' sequence that is not complementary to CHIKV nucleic acids. The oligonucleotide set further includes a second primer up to 100 bases long and including a target-complementary 3' terminal sequence of 15-38 contiguous bases of SEQ ID NO:58. The target-complementary 3' terminal sequence of the second primer can be fully contained within the sequence of SEQ ID NO:58. The second primer optionally may include a second primer 5' sequence that is not complementary to CHIKV nucleic acids. Next, there is a step for performing an in vitro nucleic acid amplification reaction using nucleic acids of the test sample as templates together with the set of amplification oligonucleotides. If the test sample included the CHIKV nucleic acid sequence, then there is produced an amplification product. Finally, the invented method includes a step for detecting with a hybridization probe any of the amplification product that may have been produced in the in vitro nucleic acid amplification reaction. If the amplification product is detected in an amount greater than a cutoff value, this indicates that the CHIKV nucleic acid sequence is present in the test sample. Alternatively, if the amplification product is detected in an amount less than the cutoff value, this indicates that the CHIKV nucleic acid sequence is absent from the test sample.

Another aspect of the invention relates to a kit (i.e., a packaged combination) for amplifying and detecting a Chikungunya virus (CHIKV) nucleic acid sequence. Generally, the kit includes a first primer up to 100 bases long and including a target-complementary 3' terminal sequence of 15-43 contiguous bases of SEQ ID NO:33. The target-complementary 3' terminal sequence of the first primer can be fully contained within the sequence of SEQ ID NO:33. The first primer optionally may include a first primer 5' sequence that is not complementary to CHIKV nucleic acids. The kit further includes a second primer up to 100 bases long and including a target-complementary 3' terminal sequence of 15-40 contiguous bases of SEQ ID NO:34. The target-complementary 3' terminal sequence of the second primer can be fully contained within the sequence of SEQ ID NO:34. The second primer optionally may include a second primer 5' sequence that is not complementary to CHIKV nucleic acids. The kit further includes a third primer up to 100 bases long and including a target-complementary 3' terminal sequence of 15-39 contiguous bases of SEQ ID NO:54. The target-complementary 3' terminal sequence of the third primer can be fully contained within the sequence of SEQ ID NO:54. The third primer optionally may include a third primer 5' sequence that is not complementary to CHIKV nucleic acids. The kit further includes a fourth primer up to 100 bases long and including a target-complementary 3' terminal sequence consisting of 15-44 contiguous bases of SEQ ID NO:55. The target-complementary 3' terminal sequence of the fourth primer can be fully contained within the sequence of SEQ ID NO:55. The fourth primer optionally may include a fourth primer 5' sequence that is not complementary to CHIKV nucleic acids. The kit further includes a hybridization probe for detecting a nucleic acid amplification product synthesized using the primers. In a preferred embodiment, the target-complementary 3' terminal sequence of the first primer is SEQ ID NO:93. In another preferred embodiment, the target-complementary 3' terminal sequence of the second primer is SEQ ID NO:94. In another preferred embodiment, the target-complementary 3' terminal sequence of the third primer is SEQ ID NO:134. In another preferred embodiment, the target-complementary 3' terminal sequence of the fourth primer is SEQ ID NO:135. In still yet another preferred embodiment, the hybridization probe is up to 44 bases in length and includes 15-44 contiguous bases of SEQ ID NO:73. For example, the hybridization probe can include SEQ ID NO:153.

Another aspect of the invention relates to a method for determining whether a Chikungunya virus (CHIKV) nucleic acid sequence is present in a test sample that includes nucleic acids. According to the method, first there is a step for contacting nucleic acids of the test sample with a set of amplification oligonucleotides that includes four primers. There is a first primer up to 100 bases long and including a target-complementary 3' terminal sequence of 15-43 contiguous bases of SEQ ID NO:33. The target-complementary 3' terminal sequence of the first primer can be fully contained within the sequence of SEQ ID NO:33. The first primer optionally may include a first primer 5' sequence that is not complementary to CHIKV nucleic acids. The oligonucleotide set further includes a second primer up to 100 bases long and including a target-complementary 3' terminal sequence of 15-40 contiguous bases of SEQ ID NO:34. The target-complementary 3' terminal sequence of the second primer can be fully contained within the sequence of SEQ ID NO:34. The second primer optionally may include a second primer 5' sequence that is not complementary to CHIKV nucleic acids. The oligonucleotide set further includes a third primer up to 100 bases long and including a target-complementary 3' terminal sequence of 15-39 contiguous bases of SEQ ID NO:54. The target-complementary 3' terminal sequence of the third primer can be fully contained within the sequence of SEQ ID NO:54. The third primer optionally may include a third primer 5' sequence that is not complementary to CHIKV nucleic acids. The oligonucleotide set further includes a fourth primer up to 100 bases long and including a target-complementary 3' terminal sequence of 15-44 contiguous bases of SEQ ID NO:55. The target-complementary 3' terminal sequence of the fourth primer can be fully contained within the sequence of SEQ ID NO:55. The fourth primer optionally may include a fourth primer 5' sequence that is not complementary to CHIKV nucleic acids. Next, there is a step for performing an in vitro nucleic acid amplification reaction using nucleic acids of the test sample as templates together with the set of amplification oligonucleotides. If the test sample included the CHIKV nucleic acid sequence, then there is produced an amplification product. Finally, the invented method includes a step for detecting with a hybridization probe any of the amplification product that may have been produced in the in vitro nucleic acid amplification reaction. If the amplification product is detected in an amount greater than a cutoff value, this indicates that the CHIKV nucleic acid sequence is present in the test sample. Alternatively, if the amplification product is detected in an amount less than the cutoff value, this indicates that the CHIKV nucleic acid sequence is absent from the test sample.

Another aspect of the invention relates to a kit (i.e., a packaged combination) for amplifying and detecting a Chikungunya virus (CHIKV) nucleic acid sequence. Generally, the kit includes a first primer up to 100 bases long and including a target-complementary 3' terminal sequence consisting of 15-40 contiguous bases of SEQ ID NO:40. The target-complementary 3' terminal sequence of the first primer can be fully contained within the sequence of SEQ ID NO:40. The first primer optionally may include a first primer 5' sequence that is not complementary to CHIKV nucleic acids. The kit further includes a second primer up to 100 bases long and including a target-complementary 3' terminal sequence of 15-45 contiguous bases of SEQ ID NO:41. The target-complementary 3' terminal sequence of the second primer can be fully contained within the sequence of SEQ ID NO:41. The second primer optionally may include a second primer 5' sequence that is not complementary to CHIKV nucleic acids. The kit further includes a third primer up to 100 bases long and including a target-complementary 3' terminal sequence of 15-38 contiguous bases of SEQ ID NO:61. The target-complementary 3' terminal sequence of the third primer can be fully contained within the sequence of SEQ ID NO:61. The third primer optionally may include a third primer 5' sequence that is not complementary to CHIKV nucleic acids. The kit further includes a hybridization probe for detecting a nucleic acid amplification product synthesized using the primers. In a preferred embodiment, the target-complementary 3' terminal sequence of the first primer is SEQ ID NO:100. In another preferred embodiment, the target-complementary 3' terminal sequence of the second primer is SEQ ID NO:101. In another preferred embodiment, the target-complementary 3' terminal sequence of the third primer is SEQ ID NO:141. In still yet another preferred embodiment, the hybridization probe is up to 38 bases in length and includes 15-38 contiguous bases of SEQ ID NO:79. For example, the hybridization probe can include SEQ ID NO:159.

Another aspect of the invention relates to a method for determining whether a Chikungunya virus (CHIKV) nucleic acid sequence is present in a test sample that includes nucleic acids. According to the method, first there is a step for contacting nucleic acids of the test sample with a set of amplification oligonucleotides that includes three primers. There is a first primer up to 100 bases long and including a target-complementary 3' terminal sequence of 15-40 contiguous bases of SEQ ID NO:40. The target-complementary 3' terminal sequence of the first primer can be fully contained within the sequence of SEQ ID NO:40. The first primer optionally may include a first primer 5' sequence that is not complementary to CHIKV nucleic acids. The oligonucleotide set further includes a second primer up to 100 bases long and including a target-complementary 3' terminal sequence of 15-45 contiguous bases of SEQ ID NO:41. The target-complementary 3' terminal sequence of the second primer can be fully contained within the sequence of SEQ ID NO:41. The second primer optionally may include a second primer 5' sequence that is not complementary to CHIKV nucleic acids. The oligonucleotide set further includes a third primer up to 100 bases long and including a target-complementary 3' terminal sequence of 15-38 contiguous bases of SEQ ID NO:61. The target-complementary 3' terminal sequence of the third primer can be fully contained within the sequence of SEQ ID NO:61. The third primer optionally may include a third primer 5' sequence that is not complementary to CHIKV nucleic acids. Next, there is a step for performing an in vitro nucleic acid amplification reaction using nucleic acids of the test sample as templates together with the set of amplification oligonucleotides. If the test sample included the CHIKV nucleic acid sequence, then there is produced an amplification product. Finally, the invented method includes a step for detecting with a hybridization probe any of the amplification product that may have been produced in the in vitro nucleic acid amplification reaction. If the amplification product is detected in an amount greater than a cutoff value, this indicates that the CHIKV nucleic acid sequence is present in the test sample. Alternatively, if the amplification product is detected in an amount less than the cutoff value, this indicates that the CHIKV nucleic acid sequence is absent from the test sample.

Another aspect of the invention relates to a kit (i.e., a packaged combination) for amplifying and detecting a Chikungunya virus (CHIKV) nucleic acid sequence. Generally, the kit includes a first primer up to 100 bases long and including a target-complementary 3' terminal sequence of 15-42 contiguous bases of SEQ ID NO:42. The target-complementary 3' terminal sequence of the first primer can be fully contained within the sequence of SEQ ID NO:42. The first primer optionally may include a first primer 5' sequence that is not complementary to CHIKV nucleic acids. The kit further includes a second primer up to 100 bases long and including a target-complementary 3' terminal sequence of 15-47 contiguous bases of SEQ ID NO:43. The target-complementary 3' terminal sequence of the second primer can be fully contained within the sequence of SEQ ID NO:43. The second primer may include a second primer 5' sequence that is not complementary to CHIKV nucleic acids. The kit further includes a third primer up to 100 bases long and including a target-complementary 3' terminal sequence of 15-43 contiguous bases of SEQ ID NO:62. The target-complementary 3' terminal sequence of the third primer can be fully contained within the sequence of SEQ ID NO:62. The third primer optionally may include a third primer 5' sequence that is not complementary to CHIKV nucleic acids. The kit further includes a hybridization probe for detecting a nucleic acid amplification product synthesized using said primers. In a preferred embodiment, the target-complementary 3' terminal sequence of the first primer is SEQ ID NO:102. In another preferred embodiment, the target-complementary 3' terminal sequence of the second primer is SEQ ID NO:103. In another preferred embodiment, the target-complementary 3' terminal sequence of the third primer is SEQ ID NO:142. In still yet another preferred embodiment, the hybridization probe is up to 38 bases in length and includes 15-38 contiguous bases of SEQ ID NO:80. For example, the hybridization probe can include SEQ ID NO:160.

Another aspect of the invention relates to a method for determining whether a Chikungunya virus (CHIKV) nucleic acid sequence is present in a test sample that includes nucleic acids. According to the method, first there is a step for contacting nucleic acids of the test sample with a set of amplification oligonucleotides that includes three primers. There is a first primer up to 100 bases long and including a target-complementary 3' terminal sequence of 15-42 contiguous bases of SEQ ID NO:42. The target-complementary 3' terminal sequence of the first primer can be fully contained within the sequence of SEQ ID NO:42. The first primer optionally may include a first primer 5' sequence that is not complementary to CHIKV nucleic acids. The oligonucleotide set further includes a second primer up to 100 bases long and including a target-complementary 3' terminal sequence of 15-47 contiguous bases of SEQ ID NO:43. The target-complementary 3' terminal sequence of the second primer can be fully contained within the sequence of SEQ ID NO:43. The second primer optionally may include a second primer 5' sequence that is not complementary to CHIKV nucleic acids. The oligonucleotide set further includes a third primer up to 100 bases long and including a target-complementary 3' terminal sequence of 15-43 contiguous bases of SEQ ID NO:62. The target-complementary 3' terminal sequence of the third primer can be fully contained within the sequence of SEQ ID NO:62. The third primer optionally may include a third primer 5' sequence that is not complementary to CHIKV nucleic acids. Next, there is a step for performing an in vitro nucleic acid amplification reaction using nucleic acids of the test sample as templates together with the set of amplification oligonucleotides. If the test sample included the CHIKV nucleic acid sequence, then there is produced an amplification product. Finally, the invented method includes a step for detecting with a hybridization probe any of the amplification product that may have been produced in the in vitro nucleic acid amplification reaction. If the amplification product is detected in an amount greater than a cutoff value, this indicates that the CHIKV nucleic acid sequence is present in the test sample. Alternatively, if the amplification product is detected in an amount less than the cutoff value, this indicates that the CHIKV nucleic acid sequence is absent from the test sample.

Another aspect of the invention relates to a kit (i.e., a packaged combination) for amplifying and detecting a Chikungunya virus (CHIKV) nucleic acid sequence. Generally, the kit includes a first primer up to 100 bases long and including a target-complementary 3' terminal sequence of 15-46 contiguous bases of SEQ ID NO:47. The target-complementary 3' terminal sequence of the first primer can be fully contained within the sequence of SEQ ID NO:47. The first primer optionally may include a first primer 5' sequence that is not complementary to CHIKV nucleic acids. The kit further includes a second primer up to 100 bases long and including a target-complementary 3' terminal sequence consisting of 15-37 contiguous bases of SEQ ID NO:67. The target-complementary 3' terminal sequence of the second primer can be fully contained within the sequence of SEQ ID NO:67. The second primer optionally may include a second primer 5' sequence that is not complementary to CHIKV nucleic acids. The kit further includes a hybridization probe for detecting a nucleic acid amplification product synthesized using said primers. In a preferred embodiment, the target-complementary 3' terminal sequence of the first primer is SEQ ID NO:107. In another preferred embodiment, the target-complementary 3' terminal sequence of the second primer is SEQ ID NO:147. In still yet another preferred embodiment, the hybridization probe is up to 38 bases in length and includes 15-38 contiguous bases of SEQ ID NO:83. For example, the hybridization probe can include SEQ ID NO:163.

Another aspect of the invention relates to a method for determining whether a Chikungunya virus (CHIKV) nucleic acid sequence is present in a test sample that includes nucleic acids. According to the method, first there is a step for contacting nucleic acids of the test sample with a set of amplification oligonucleotides that includes two primers. There is a first primer up to 100 bases long and including a target-complementary 3' terminal sequence of 15-46 contiguous bases of SEQ ID NO:47. The target-complementary 3' terminal sequence of the first primer can be fully contained within the sequence of SEQ ID NO:47. The first primer optionally may include a first primer 5' sequence that is not complementary to CHIKV nucleic acids. The oligonucleotide set further includes a second primer up to 100 bases long and including a target-complementary 3' terminal sequence of 15-37 contiguous bases of SEQ ID NO:67. The target-complementary 3' terminal sequence of the second primer can be fully contained within the sequence of SEQ ID NO:67. The second primer optionally may include a second primer 5' sequence that is not complementary to CHIKV nucleic acids. Next, there is a step for performing an in vitro nucleic acid amplification reaction using nucleic acids of the test sample as templates together with the set of amplification oligonucleotides. If the test sample included the CHIKV nucleic acid sequence, then there is produced an amplification product. Finally, the invented method includes a step for detecting with a hybridization probe any of the amplification product that may have been produced in the in vitro nucleic acid amplification reaction. If the amplification product is detected in an amount greater than a cutoff value, this indicates that the CHIKV nucleic acid sequence is present in the test sample. Alternatively, if the amplification product is detected in an amount less than the cutoff value, this indicates that the CHIKV nucleic acid sequence is absent from the test sample.

Another aspect of the invention relates to a kit (i.e., a packaged combination) for amplifying and detecting a Chikungunya virus (CHIKV) nucleic acid sequence. Generally, the kit includes a first primer up to 100 bases long and including a target-complementary 3' terminal sequence of 15-40 contiguous bases of SEQ ID NO:38. The target-complementary 3' terminal sequence of the first primer can be fully contained within the sequence of SEQ ID NO:38. The first primer optionally may include a first primer 5' sequence that is not complementary to CHIKV nucleic acids. The kit further includes a second primer up to 100 bases long and including a target-complementary 3' terminal sequence of 15-39 contiguous bases of SEQ ID NO:59. The target-complementary 3' terminal sequence of the second primer can be fully contained within the sequence of SEQ ID NO:59. The second primer optionally may include a second primer 5' sequence that is not complementary to CHIKV nucleic acids. The kit further includes a hybridization probe for detecting a nucleic acid amplification product synthesized using said primers. In a preferred embodiment, the target-complementary 3' terminal sequence of the first primer is SEQ ID NO:98. In another preferred embodiment, the target-complementary 3' terminal sequence of the second primer is SEQ ID NO:139. In still yet another preferred embodiment, the hybridization probe is up to 38 bases in length and includes 15-38 contiguous bases of SEQ ID NO:77. For example, the hybridization probe may include SEQ ID NO:157.

Another aspect of the invention relates to a method for determining whether a Chikungunya virus (CHIKV) nucleic acid sequence is present in a test sample that includes nucleic acids. According to the method, first there is a step for contacting nucleic acids of the test sample with a set of amplification oligonucleotides that includes two primers. There is a first primer up to 100 bases long and including a target-complementary 3' terminal sequence of 15-40 contiguous bases of SEQ ID NO:38. The target-complementary 3' terminal sequence of the first primer can be fully contained within the sequence of SEQ ID NO:38. The first primer optionally may include a first primer 5' sequence that is not complementary to CHIKV nucleic acids. The oligonucleotide set further includes a second primer up to 100 bases long and including a target-complementary 3' terminal sequence of 15-39 contiguous bases of SEQ ID NO:59. The target-complementary 3' terminal sequence of the second primer can be fully contained within the sequence of SEQ ID NO:59. The second primer optionally may include a second primer 5' sequence that is not complementary to CHIKV nucleic acids. Next, there is a step for performing an in vitro nucleic acid amplification reaction using nucleic acids of the test sample as templates together with the set of amplification oligonucleotides. If the test sample included the CHIKV nucleic acid sequence, then there is produced an amplification product. Finally, the invented method includes a step for detecting with a hybridization probe any of the amplification product that may have been produced in the in vitro nucleic acid amplification reaction. If the amplification product is detected in an amount greater than a cutoff value, this indicates that the CHIKV nucleic acid sequence is present in the test sample. Alternatively, if the amplification product is detected in an amount less than the cutoff value, this indicates that the CHIKV nucleic acid sequence is absent from the test sample.

Another aspect of the invention relates to a kit (i.e., a packaged combination) for amplifying and detecting a Chikungunya virus (CHIKV) nucleic acid sequence. Generally, the kit includes a first primer up to 100 bases long and including a target-complementary 3' terminal sequence consisting of 15-43 contiguous bases of SEQ ID NO:35. The target-complementary 3' terminal sequence of the first primer can be fully contained within the sequence of SEQ ID NO:35. The first primer optionally may include a first primer 5' sequence that is not complementary to CHIKV nucleic acids. The kit further includes a second primer up to 100 bases long and including a target-complementary 3' terminal sequence of 15-41 contiguous bases of SEQ ID NO:56. The target-complementary 3' terminal sequence of the second primer can be fully contained within the sequence of SEQ ID NO:56. The second primer optionally may include a second primer 5' sequence that is not complementary to CHIKV nucleic acids. The kit further includes a hybridization probe for detecting a nucleic acid amplification product synthesized using said primers. In a preferred embodiment, the target-complementary 3' terminal sequence of the first primer is SEQ ID NO:95. In another preferred embodiment, the target-complementary 3' terminal sequence of the second primer is SEQ ID NO:136. In still yet another preferred embodiment, the hybridization probe is up to 40 bases in length and comprises 15-40 contiguous bases of SEQ ID NO:74. For example, the hybridization probe may include SEQ ID NO:154.

Another aspect of the invention relates to a method for determining whether a Chikungunya virus (CHIKV) nucleic acid sequence is present in a test sample that includes nucleic acids. According to the method, first there is a step for contacting nucleic acids of the test sample with a set of amplification oligonucleotides that includes two primers. There is a first primer up to 100 bases long and including a target-complementary 3' terminal sequence of 15-43 contiguous bases of SEQ ID NO:35. The target-complementary 3' terminal sequence of the first primer can be fully contained within the sequence of SEQ ID NO:35. The first primer optionally may include a first primer 5' sequence that is not complementary to CHIKV nucleic acids. The oligonucleotide set further includes a second primer up to 100 bases long and including a target-complementary 3' terminal sequence of 15-41 contiguous bases of SEQ ID NO:56. The target-complementary 3' terminal sequence of the second primer can be fully contained within the sequence of SEQ ID NO:56. The second primer optionally may include a second primer 5' sequence that is not complementary to CHIKV nucleic acids. Next, there is a step for performing an in vitro nucleic acid amplification reaction using nucleic acids of the test sample as templates together with the set of amplification oligonucleotides. If the test sample included the CHIKV nucleic acid sequence, then there is produced an amplification product. Finally, the invented method includes a step for detecting with a hybridization probe any of the amplification product that may have been produced in the in vitro nucleic acid amplification reaction. If the amplification product is detected in an amount greater than a cutoff value, this indicates that the CHIKV nucleic acid sequence is present in the test sample. Alternatively, if the amplification product is detected in an amount less than the cutoff value, this indicates that the CHIKV nucleic acid sequence is absent from the test sample.

Definitions

The following terms have the following meanings for the purpose of this disclosure, unless expressly stated to the contrary herein.

As used herein, a "biological sample" is any tissue or polynucleotide-containing material obtained from a human, animal or environmental sample. Biological samples in accordance with the invention include peripheral blood, plasma, serum or other body fluid, bone marrow or other organ, biopsy tissues or other materials of biological origin. A biological sample may be treated to disrupt tissue or cell structure, thereby releasing intracellular components into a solution which may contain enzymes, buffers, salts, detergents and the like.

As used herein, "polynucleotide" means either RNA or DNA, along with any synthetic nucleotide analogs or other molecules that may be present in the sequence and that do not prevent hybridization of the polynucleotide with a second molecule having a complementary sequence.

As used herein, a "detectable label" is a chemical species that can be detected or can lead to a detectable response. Detectable labels in accordance with the invention can be linked to polynucleotide probes either directly or indirectly, and include radioisotopes, enzymes, haptens, chromophores such as dyes or particles that impart a detectable color (e.g., latex beads or metal particles), luminescent compounds (e.g., bioluminescent, phosphorescent or chemiluminescent moieties) and fluorescent compounds.

A "homogeneous detectable label" refers to a label that can be detected in a homogeneous fashion by determining whether the label is on a probe hybridized to a target sequence. That is, homogeneous detectable labels can be detected without physically removing hybridized from unhybridized forms of the label or labeled probe. Homogeneous detectable labels are preferred when using labeled probes for detecting CHIKV nucleic acids. Examples of homogeneous labels have been described in detail by Arnold et al., U.S. Pat. No. 5,283,174; Woodhead et al., U.S. Pat. No. 5,656,207; and Nelson et al., U.S. Pat. No. 5,658,737. Preferred labels for use in homogenous assays include chemiluminescent compounds (e.g., see Woodhead et al., U.S. Pat. No. 5,656,207; Nelson et al., U.S. Pat. No. 5,658,737; and Arnold, Jr., et al., U.S. Pat. No. 5,639,604). Preferred chemiluminescent labels are acridinium ester ("AE") compounds, such as standard AE or derivatives thereof (e.g., naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE).

A "homogeneous assay" refers to a detection procedure that does not require physical separation of hybridized probe from non-hybridized probe prior to determining the extent of specific probe hybridization. Exemplary homogeneous assays, such as those described herein, can employ molecular beacons or other self-reporting probes which emit fluorescent signals when hybridized to an appropriate target, chemiluminescent acridinium ester labels which can be selectively destroyed by chemical means unless present in a hybrid duplex, and other homogeneously detectable labels that will be familiar to those having an ordinary level of skill in the art.

As used herein, "amplification" refers to an in vitro procedure for obtaining multiple copies of a target nucleic acid sequence, its complement or fragments thereof. A single round of reverse transcription, or reverse transcription followed by second-strand cDNA synthesis and cloning is not considered in vitro amplification. Conventionally, amplification is intended to embrace production of at least 4 synthetic copies of a starting template strand. Preferably, synthetic copies serve as templates for subsequent rounds of sequence-specific polynucleotide synthesis.

By "target nucleic acid" or "target" is meant a nucleic acid containing a target nucleic acid sequence. In general, a target nucleic acid sequence that is to be amplified will be positioned between two oppositely disposed primers, and will include the portion of the target nucleic acid that is fully complementary to each of the primers.

By "target nucleic acid sequence" or "target sequence" or "target region" is meant a specific deoxyribonucleotide or ribonucleotide sequence comprising all or part of the nucleotide sequence of a single-stranded nucleic acid molecule, and the deoxyribonucleotide or ribonucleotide sequence complementary thereto.

By "transcription associated amplification" is meant any type of nucleic acid amplification that uses an RNA polymerase to produce multiple RNA transcripts from a nucleic acid template. One example of a transcription associated amplification method, called "Transcription Mediated Amplification" (TMA), generally employs an RNA polymerase, a DNA polymerase, deoxyribonucleoside triphosphates, ribonucleoside triphosphates, and a promoter-template complementary oligonucleotide, and optionally may include one or more analogous oligonucleotides. Variations of TMA are well known in the art as disclosed in detail in Burg et al., U.S. Pat. No. 5,437,990; Kacian et al., U.S. Pat. Nos. 5,399,491 and 5,554,516; Kacian et al., PCT No. WO 93/22461; Gingeras et al., PCT No. WO 88/01302; Gingeras et al., PCT No. WO 88/10315; Malek et al., U.S. Pat. No. 5,130,238; Urdea et al., U.S. Pat. Nos. 4,868,105 and 5,124,246; McDonough et al., PCT No. WO 94/03472; and Ryder et al., PCT No. WO 95/03430. The methods of Kacian et al. are preferred for conducting nucleic acid amplification procedures of the type disclosed herein.

As used herein, an "oligonucleotide" or "oligomer" is a polymeric chain of at least two, generally between about five and about 100, chemical subunits, each subunit comprising a nucleotide base moiety, a sugar moiety, and a linking moiety that joins the subunits in a linear spacial configuration. Common nucleotide base moieties are guanine (G), adenine (A), cytosine (C), thymine (T) and uracil (U), although other rare or modified nucleotide bases able to hydrogen bond are well known to those skilled in the art. Oligonucleotides may optionally include analogs of any of the sugar moieties, the base moieties, and the backbone constituents. Preferred oligonucleotides of the present invention fall in a size range of about 10 to about 100 residues. Oligonucleotides may be purified from naturally occurring sources, but preferably are synthesized using any of a variety of well known enzymatic or chemical methods.

As used herein, a "probe" is an oligonucleotide that hybridizes specifically to a target sequence in a nucleic acid, preferably in an amplified nucleic acid, under conditions that promote hybridization, to form a detectable hybrid. A probe optionally may contain a detectable moiety which either may be attached to the end(s) of the probe or may be internal. The nucleotides of the probe which combine with the target polynucleotide need not be strictly contiguous, as may be the case with a detectable moiety internal to the sequence of the probe. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). The "target" of a probe generally refers to a sequence contained within an amplified nucleic acid sequence which hybridizes specifically to at least a portion of a probe oligonucleotide using standard hydrogen bonding (i.e., base pairing). A probe may comprise target-specific sequences and optionally other sequences that are non-complementary to the target sequence that is to be detected. These non-complementary sequences may comprise a promoter sequence, a restriction endonuclease recognition site, or sequences that contribute to three-dimensional conformation of the probe (e.g., as described in Lizardi et al., U.S. Pat. Nos. 5,118,801 and 5,312,728). Sequences that are "sufficiently complementary" allow stable hybridization of a probe oligonucleotide to a target sequence that is not completely complementary to the probe's target-specific sequence.

As used herein, an "amplification oligonucleotide" is an oligonucleotide that hybridizes to a target nucleic acid, or its complement, and participates in a nucleic acid amplification reaction. Examples of amplification oligonucleotides include amplification primers, or more simply "primers." Primers are optionally modified oligonucleotides which are capable of hybridizing to a template nucleic acid and which have a 3' end that can be extended by a DNA polymerase activity. A primer will have a downstream CHIKV-complementary sequence, and optionally an upstream sequence that is not complementary to CHIKV nucleic acids. The optional upstream sequence may, for example, serve as an RNA polymerase promoter or contain restriction endonuclease cleavage sites. Generally speaking, amplification oligomers (e.g., primers) will have at least 12 contiguous bases complementary to a target nucleic acid sequence, or more preferably at least 15 contiguous bases complementary to the target nucleic acid sequence that is to be amplified or detected. As well, certain highly preferred amplification oligomers are capable of hybridizing a target nucleic acid sequence under the example stringent hybridization conditions set forth herein.

By "substantially homologous," "substantially corresponding" or "substantially corresponds" is meant that the subject oligonucleotide has a base sequence containing an at least 10 contiguous base region that is at least 70% homologous, preferably at least 80% homologous, more preferably at least 90% homologous, and most preferably 100% homologous to an at least 10 contiguous base region present in a reference base sequence (excluding RNA and DNA equivalents). Those skilled in the art will readily appreciate modifications that could be made to the hybridization assay conditions at various percentages of homology to permit hybridization of the oligonucleotide to the target sequence while preventing unacceptable levels of non-specific hybridization. The degree of similarity is determined by comparing the order of nucleobases making up the two sequences and does not take into consideration other structural differences which may exist between the two sequences, provided the structural differences do not prevent hydrogen bonding with complementary bases. The degree of homology between two sequences can also be expressed in terms of the number of base mismatches present in each set of at least 10 contiguous bases being compared, which may range from 0-2 base differences.

By "substantially complementary" is meant that the subject oligonucleotide has a base sequence containing an at least 10 contiguous base region that is at least 70% complementary, preferably at least 80% complementary, more preferably at least 90% complementary, and most preferably 100% complementary to an at least 10 contiguous base region present in a target nucleic acid sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization.) The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 10 contiguous bases being compared, which may range from 0-2 base mismatches.

By "sufficiently complementary" is meant a contiguous nucleic acid base sequence that is capable of hybridizing to another base sequence by hydrogen bonding between a series of complementary bases. Complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence under appropriate hybridization conditions. Contiguous bases are preferably at least about 80%, more preferably at least about 90%, and most preferably about 100% complementary to a sequence to which an oligonucleotide is intended to specifically hybridize. Appropriate hybridization conditions are well known to those skilled in the art, can be predicted readily based on base sequence composition, or can be determined empirically by using routine testing (e.g., See Sambrook et al., *Molecular Cloning, A Laboratory Manual*, $2^{nd}$ ed. (Cold Spring Harbor Laboratory Press, Cold Spring Harbor, N.Y., 1989) at §§ 1.90-1.91, 7.37-7.57, 9.47-9.51 and 11.47-11.57 particularly at §§ 9.50-9.51, 11.12-11.13, 11.45-11.47 and 11.55-11.57).

By "capture oligonucleotide" is meant at least one nucleic acid oligonucleotide that provides means for specifically joining a target sequence and an immobilized oligonucleotide due to base pair hybridization. A capture oligonucleotide preferably includes two binding regions: a target sequence-binding region and an immobilized probe-binding region, usually contiguous on the same oligonucleotide, although the capture oligonucleotide may include a target sequence-binding region and an immobilized probe-binding region which are present on two different oligonucleotides joined together by one or more linkers. For example, an immobilized probe-binding region may be present on a first oligonucleotide, the target sequence-binding region may be present on a second oligonucleotide, and the two different oligonucleotides are joined by hydrogen bonding with a linker that is a third oligonucleotide containing sequences that hybridize specifically to the sequences of the first and second oligonucleotides.

By "immobilized probe" or "immobilized nucleic acid" is meant a nucleic acid that joins, directly or indirectly, a capture oligonucleotide to an immobilized support. An immobilized probe is an oligonucleotide joined to a solid support that facilitates separation of bound target sequence from unbound material in a sample.

By "separating" or "purifying" is meant that one or more components of the biological sample are removed from one or more other components of the sample. Sample components include nucleic acids in a generally aqueous solution phase which may also include materials such as proteins, carbohydrates, lipids and labeled probes. Preferably, the separating or purifying step removes at least about 70%, more preferably at least about 90% and, even more preferably, at least about 95% of the other components present in the sample.

By "RNA and DNA equivalents" or "RNA and DNA equivalent bases" is meant molecules, such as RNA and DNA, having the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence.

By "consisting essentially of" is meant that additional component(s), composition(s) or method step(s) that do not materially change the basic and novel characteristics of the present invention may be included in the compositions or kits or methods of the present invention. Such characteristics include the ability to selectively detect CHIKV nucleic acids in biological samples such as whole blood or plasma. Any component(s), composition(s), or method step(s) that have a material effect on the basic and novel characteristics of the present invention would fall outside of this term.

BRIEF DESCRIPTION OF THE DRAWINGS

FIG. 1 is a schematic diagram illustrating the various polynucleotides that can be used for detecting a target region within the Chikungunya virus nucleic acid (represented by a thick horizontal line). Positions of the following nucleic acids are shown relative to the target region: "Capture Oligonucleotide" refers to the nucleic acid used to hybridize to and capture the target nucleic acid prior to amplification, where "T" refers to a tail sequence used to hybridize an immobilized oligonucleotide having a complementary sequence (not shown); "Non-T7 Primer" and "T7 Promoter-Primer" represent two amplification primers used for conducting TMA, where "P" indicates the promoter sequence of the T7 promoter-primer; and "Probe" refers to the probe used for detecting amplified nucleic acid.

DETAILED DESCRIPTION

Disclosed herein are compositions, methods and kits for selectively detecting the nucleic acids of Chikungunya virus (CHIKV), in biological samples such as viral lysates, blood, serum, plasma or other body fluid or tissue. The probes, primers and methods of the invention can be used either for environmental testing or in diagnostic applications, or for screening donated blood and blood products or other tissues that may contain infectious particles. Yet another application includes screening of environmental samples, such as mosquito pools, for the presence of the virus.

Introduction and Overview

The present invention includes compositions (nucleic acid capture oligonucleotides, amplification oligonucleotides and probes), methods and kits that are particularly useful for detecting CHIKV nucleic acids in a biological sample. To design oligonucleotide sequences appropriate for such uses, known CHIKV nucleic acid sequences were first compared to identify candidate regions of the viral genome that could serve as reagents in a diagnostic assay. As a result of these comparisons, different regions of the CHIKV genome were selected as targets for detection using the capture oligonucleotides, primers and probes shown schematically in FIG. 1. Portions of sequences containing relatively few variants between the compared sequences were chosen as starting points for designing synthetic oligonucleotides suitable for use in capture, amplification and detection of amplified sequences.

Based on these analyses, the capture oligonucleotide, amplification primer and probe sequences presented below were designed. Those having an ordinary level of skill in the art will appreciate that any primer sequences specific for CHIKV or other target, with or without a T7 promoter sequence, may be used as primers in the various primer-based in vitro amplification methods described below. It is also contemplated that oligonucleotides having the sequences disclosed herein could serve alternative functions in assays for detecting CHIKV nucleic acids. For example, the capture oligonucleotides disclosed herein could serve as hybridization probes, the hybridization probes disclosed herein could be used as amplification primers, and the amplification primers disclosed herein could be used as hybridization probes in alternative detection assays.

Moreover, while particularly disclosed probe sequences may be used as primers, and while particularly disclosed primers may be used as probes, the same is true for disclosed probe domains and primer domains. The probe domains disclosed herein are also intended for use as primer domains (e.g., at lease 15 contiguous bases, or more preferably 17 contiguous bases of an identified probe domain can function as a primer). Likewise, primer domains disclosed herein are also intended for use as probe domains (e.g., at least 15 contiguous bases, or more preferably 17 contiguous bases of an identified primer domain can function as a probe). Example 2 herein presents evidence for this functional interchangeability.

Also contemplated as falling within the scope of the invention is the combined use of oligonucleotides from two different disclosed systems. For example, the probe sequence from one system can be employed as a primer which can be used in combination with an opposite strand oligonucleotide from a different system in an in vitro amplification procedure.

The amplification primers disclosed herein are further contemplated as components of multiplex amplification reactions wherein several amplicon species can be produced from an assortment of target-specific primers. For example, it is contemplated that certain preferred CHIKV-specific primers disclosed herein can be used in multiplex amplification reactions that are capable of amplifying polynucleotides of unrelated viruses without substantially compromising the sensitivities of those assays. Particular examples of these unrelated viruses include West Nile virus and Dengue virus. As well, more than one of the amplification systems disclosed herein can be combined to result in a multiplex assay that is both robust and broad in its capacity for target detection.

Useful Amplification Methods

Amplification methods useful in connection with the present invention include: Transcription Mediated Amplification (TMA), Nucleic Acid Sequence-Based Amplification (NASBA), the Polymerase Chain Reaction (PCR), Strand Displacement Amplification (SDA), and amplification methods using self-replicating polynucleotide molecules and replication enzymes such as MDV-1 RNA and Q-beta enzyme. Methods for carrying out these various amplification techniques respectively can be found in U.S. Pat. No. 5,399,491, published European patent application EP 0 525 882, U.S. Pat. No. 4,965,188, U.S. Pat. No. 5,455,166, U.S. Pat. No. 5,472,840 and Lizardi et al., *BioTechnology* 6:1197 (1988). The disclosures of these documents which describe how to perform nucleic acid amplification reactions are hereby incorporated by reference.

In a highly preferred embodiment of the invention, CHIKV nucleic acid sequences are amplified using a TMA protocol. According to this protocol, the reverse transcriptase which provides the DNA polymerase activity also possesses an endogenous RNase H activity. One of the primers used in this procedure contains a promoter sequence positioned upstream of a sequence that is complementary to one strand of a target nucleic acid that is to be amplified. In the first step of the amplification, a promoter-primer hybridizes to the CHIKV target RNA at a defined site. Reverse transcriptase creates a complementary DNA copy of the target RNA by extension from the 3' end of the promoter-primer. Following interaction of an opposite strand primer with the newly synthesized DNA strand, a second strand of DNA is synthesized from the end of the primer by reverse transcriptase, thereby creating a double-stranded DNA molecule. RNA polymerase recognizes the promoter sequence in this double-stranded DNA template and initiates transcription. Each of the newly synthesized RNA amplicons re-enters the TMA process and serves as a template for a new round of replication, thereby leading to an exponential expansion of the RNA amplicon. Since each of the DNA templates can make 100-1000 copies of RNA amplicon, this expansion can result in the production of 10 billion amplicons in less than one hour. The entire process is autocatalytic and is performed at a constant temperature.

Structural Features of Primers

As indicated above, a "primer" refers to an optionally modified oligonucleotide which is capable of participating in a nucleic acid amplification reaction. Preferred primers are capable of hybridizing to a template nucleic acid and which has a 3' end that can be extended by a DNA polymerase activity. The 5' region of the primer may be non-complementary to the target nucleic acid. If the 5' non-complementary region includes a promoter sequence, it is referred to as a "promoter-primer." Those skilled in the art will appreciate that any oligonucleotide that can function as a primer (i.e., an oligonucleotide that hybridizes specifically to a target sequence and has a 3' end capable of extension by a DNA polymerase activity) can be modified to include a 5' promoter sequence, and thus could function as a promoter-primer. Similarly, any promoter-primer can be modified by removal of, or synthesis without, a promoter sequence and still function as a primer.

Nucleotide base moieties of primers may be modified (e.g., by the addition of propyne groups), as long as the modified base moiety retains the ability to form a non-covalent association with G, A, C, T or U, and as long as an oligonucleotide comprising at least one modified nucleotide base moiety or analog is not sterically prevented from hybridizing with a single-stranded nucleic acid. As indicated below in connection with the chemical composition of useful probes, the nitrogenous bases of primers in accordance with the invention may be conventional bases (A, G, C, T, U), known analogs thereof (e.g., inosine or "I" having hypoxanthine as its base moiety; see *The Biochemistry of the Nucleic Acids* 5-36, Adams et al., ed., $11^{th}$ ed., 1992), known derivatives of purine or pyrimidine bases (e.g., $N^4$-methyl deoxygaunosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines (see, Cook, PCT Int'l Pub.

No. WO 93/13121) and "abasic" residues where the backbone includes no nitrogenous base for one or more residues of the polymer (see Arnold et al., U.S. Pat. No. 5,585,481). Common sugar moieties that comprise the primer backbone include ribose and deoxyribose, although 2'-O-methyl ribose (OMe), halogenated sugars, and other modified sugar moieties may also be used. Usually, the linking group of the primer backbone is a phosphorus-containing moiety, most commonly a phosphodiester linkage, although other linkages, such as, for example, phosphorothioates, methylphosphonates, and non-phosphorus-containing linkages such as peptide-like linkages found in "peptide nucleic acids" (PNA) also are intended for use in the assay disclosed herein.

Useful Probe Labeling Systems and Detectable Moieties

Essentially any labeling and detection system that can be used for monitoring specific nucleic acid hybridization can be used in conjunction with the present invention. Included among the collection of useful labels are radiolabels, enzymes, haptens, linked oligonucleotides, chemiluminescent molecules, fluorescent moieties (either alone or in combination with "quencher" moieties), and redox-active moieties that are amenable to electronic detection methods. Preferred chemiluminescent molecules include acridinium esters of the type disclosed by Arnold et al., in U.S. Pat. No. 5,283,174 for use in connection with homogenous protection assays, and of the type disclosed by Woodhead et al., in U.S. Pat. No. 5,656,207 for use in connection with assays that quantify multiple targets in a single reaction. The disclosures contained in these patent documents are hereby incorporated by reference. Preferred electronic labeling and detection approaches are disclosed in U.S. Pat. Nos. 5,591,578 and 5,770,369, and the published international patent application WO 98/57158, the disclosures of which are hereby incorporated by reference. Redox active moieties useful as labels in the present invention include transition metals such as Cd, Mg, Cu, Co, Pd, Zn, Fe and Ru.

Particularly preferred detectable labels for probes in accordance with the present invention are detectable in homogeneous assay systems (i.e., where, in a mixture, bound labeled probe exhibits a detectable change, such as stability or differential degradation, compared to unbound labeled probe). While other homogeneously detectable labels, such as fluorescent labels and electronically detectable labels, are intended for use in the practice of the present invention, a preferred label for use in homogenous assays is a chemiluminescent compound (e.g., as described by Woodhead et al., in U.S. Pat. No. 5,656,207; by Nelson et al., in U.S. Pat. No. 5,658,737; or by Arnold et al., in U.S. Pat. No. 5,639,604). Particularly preferred chemiluminescent labels include acridinium ester ("AE") compounds, such as standard AE or derivatives thereof, such as naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE.

In some applications, probes exhibiting at least some degree of self-complementarity are desirable to facilitate detection of probe:target duplexes in a test sample without first requiring the removal of unhybridized probe prior to detection. By way of example, structures referred to as "Molecular Torches" are designed to include distinct regions of self-complementarity (coined "the target binding domain" and "the target closing domain") which are connected by a joining region and which hybridize to one another under predetermined hybridization assay conditions. When exposed to denaturing conditions, the two complementary regions (which may be fully or partially complementary) of the Molecular Torch melt, leaving the target binding domain available for hybridization to a target sequence when the predetermined hybridization assay conditions are restored. Molecular Torches are designed so that the target binding domain favors hybridization to the target sequence over the target closing domain. The target binding domain and the target closing domain of a Molecular Torch include interacting labels (e.g., fluorescent/quencher) positioned so that a different signal is produced when the Molecular Torch is self-hybridized as opposed to when the Molecular Torch is hybridized to a target nucleic acid, thereby permitting detection of probe:target duplexes in a test sample in the presence of unhybridized probe having a viable label associated therewith. Molecular Torches are fully described in U.S. Pat. No. 6,361,945, the disclosure of which is hereby incorporated by reference.

Another example of a self-complementary hybridization assay probe that may be used in conjunction with the invention is a structure commonly referred to as a "Molecular Beacon." Molecular Beacons comprise nucleic acid molecules having a target complementary sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular Beacons are fully described in U.S. Pat. No. 5,925,517, the disclosure of which is hereby incorporated by reference. Molecular beacons useful for detecting CHIKV-specific nucleic acid sequences may be created by appending to either end of one of the probe sequences disclosed herein, a first nucleic acid arm comprising a fluorophore and a second nucleic acid arm comprising a quencher moiety. In this configuration, the CHIKV-specific probe sequence disclosed herein serves as the target-complementary "loop" portion of the resulting molecular beacon.

Molecular beacons preferably are labeled with an interactive pair of detectable labels. Examples of detectable labels that are preferred as members of an interactive pair of labels interact with each other by FRET or non-FRET energy transfer mechanisms. Fluorescence resonance energy transfer (FRET) involves the radiationless transmission of energy quanta from the site of absorption to the site of its utilization in the molecule, or system of molecules, by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred. In addition to FRET, there are at least three other "non-FRET" energy transfer processes by which excitation energy can be transferred from a donor to an acceptor molecule.

When two labels are held sufficiently close that energy emitted by one label can be received or absorbed by the second label, whether by a FRET or non-FRET mechanism, the two labels are said to be in "energy transfer relationship" with each other. This is the case, for example, when a molecular beacon is maintained in the closed state by formation of a stem duplex, and fluorescent emission from a fluorophore attached to one arm of the probe is quenched by a quencher moiety on the opposite arm.

Highly preferred label moieties for the invented molecular beacons include a fluorophore and a second moiety having fluorescence quenching properties (i.e., a "quencher"). In this embodiment, the characteristic signal is likely fluorescence of a particular wavelength, but alternatively could be a visible light signal. When fluorescence is involved, changes in emission are preferably due to FRET, or to radiative energy transfer or non-FRET modes. When a molecular beacon having a pair of interactive labels in the closed state is stimulated by an appropriate frequency of light, a fluorescent signal is generated at a first level, which may be very low. When this same probe is in the open state and is stimulated by an appropriate frequency of light, the fluorophore and the quencher moieties are sufficiently separated from each other that energy transfer between them is substantially precluded. Under that condition, the quencher moiety is unable to quench the fluorescence from the fluorophore moiety. If the fluorophore is stimulated by light energy of an appropriate wavelength, a fluorescent signal of a second level, higher than the first level, will be generated. The difference between the two levels of fluorescence is detectable and measurable. Using fluorophore and quencher moieties in this manner, the molecular beacon is only "on" in the "open" conformation and indicates that the probe is bound to the target by emanating an easily detectable signal. The conformational state of the probe alters the signal generated from the probe by regulating the interaction between the label moieties.

Examples of donor/acceptor label pairs that may be used in connection with the invention, making no attempt to distinguish FRET from non-FRET pairs, include fluorescein/tetramethylrhodamine, IAEDANS/fluororescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2 and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY 7 dyes advantageously eliminate the potential problem of background fluorescence resulting from direct (i.e., non-sensitized) acceptor excitation. Preferred fluorophore moieties that can be used as one member of a donor-acceptor pair include fluorescein, ROX, and the CY dyes (such as CY5). Highly preferred quencher moieties that can be used as another member of a donor-acceptor pair include DABCYL and the BLACK HOLE QUENCHER moieties which are available from Biosearch Technologies, Inc., (Novato, Calif.).

Synthetic techniques and methods of bonding labels to nucleic acids and detecting labels are well known in the art (e.g., see Sambrook et al., *Molecular Cloning, A Laboratory Manual*, 2nd ed. (Cold Spring Harbor Laboratory Press, Cold Spring Harbor, N. Y., 1989), Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. No. 5,283,174; Kourilsky et al., U.S. Pat. No. 4,581,333), and Becker et al., European Patent App. No. 0 747 706.

Chemical Composition of Probes

Probes in accordance with the invention comprise polynucleotides or polynucleotide analogs and optionally may carry a detectable label covalently bonded thereto. Nucleosides or nucleoside analogs of the probe comprise nitrogenous heterocyclic bases, or base analogs, where the nucleosides are linked together, for example by phospohdiester bonds to form a polynucleotide. Accordingly, a probe may comprise conventional ribonucleic acid (RNA) and/or deoxyribonucleic acid (DNA), but also may comprise chemical analogs of these molecules. The "backbone" of a probe may be made up of a variety of linkages known in the art, including one or more sugar-phosphodiester linkages, peptide-nucleic acid bonds (sometimes referred to as "peptide nucleic acids" as described by Hyldig-Nielsen et al., PCT Int'l Pub. No. WO 95/32305), phosphorothioate linkages, methylphosphonate linkages or combinations thereof. Sugar moieties of the probe may be either ribose or deoxyribose, or similar compounds having known substitutions, such as, for example, 2'-O-methyl ribose and 2' halide substitutions (e.g., 2'-F). The nitrogenous bases may be conventional bases (A, G, C, T, U), known analogs thereof (e.g., inosine or "I"; see *The Biochemistry of the Nucleic Acids* 5-36, Adams et al., ed., 11$^{th}$ ed., 1992), known derivatives of purine or pyrimidine bases (e.g., N$^4$-methyl deoxygaunosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines (see, Cook, PCT Int'l Pub. No. WO 93/13121) and "abasic" residues where the backbone includes no nitrogenous base for one or more residues of the polymer (see Arnold et al., U.S. Pat. No. 5,585,481). A probe may comprise only conventional sugars, bases and linkages found in RNA and DNA, or may include both conventional components and substitutions (e.g., conventional bases linked via a methoxy backbone, or a nucleic acid including conventional bases and one or more base analogs).

While oligonucleotide probes of different lengths and base composition may be used for detecting CHIKV nucleic acids, preferred probes in this invention have lengths of up to 100 nucleotides, and more preferably have lengths of up to 60 nucleotides. Preferred length ranges for the invented oligonucleotides are from 10 to 100 bases in length, or more preferably between 15 and 50 bases in length, or still more preferably between 15 and 30 bases in length. However, the specific probe sequences described below also may be provided in a nucleic acid cloning vector or transcript or other longer nucleic acid and still can be used for detecting CHIKV nucleic acids.

Selection of Amplification Primers and Detection Probes Specific for CHIKV

Useful guidelines for designing amplification primers and probes with desired characteristics are described herein. The optimal sites for amplifying and probing CHIKV nucleic acids contain two, and preferably three, conserved regions each greater than about 15 bases in length, preferably within about 200 bases of contiguous sequence. The degree of amplification observed with a set of primers or promoter-primers depends on several factors, including the ability of the oligonucleotides to hybridize to their complementary sequences and their ability to be extended enzymatically. Because the extent and specificity of hybridization reactions are affected by a number of factors, manipulation of those factors will determine the exact sensitivity and specificity of a particular oligonucleotide, whether perfectly complementary to its target or not. The effects of varying assay conditions are known to those skilled in the art, and are described by Hogan et al., in U.S. Pat. No. 5,840,488, the disclosure of which is hereby incorporated by reference.

The length of the target nucleic acid sequence and, accordingly, the length of the primer sequence or probe sequence can be important. In some cases, there may be several sequences from a particular target region, varying in location and length, which will yield primers or probes having the desired hybridization characteristics. While it is possible for nucleic acids that are not perfectly complementary to hybridize, the longest stretch of perfectly homologous base sequence will normally primarily determine hybrid stability.

Amplification primers and probes should be positioned to minimize the stability of the oligonucleotide:nontarget (i.e., nucleic acid with similar sequence to target nucleic acid) nucleic acid hybrid. It is preferred that the amplification primers and detection probes are able to distinguish between target and non-target sequences. In designing primers and probes, the differences in these Tm values should be as large as possible (e.g., at least 2° C. and preferably 5° C.).

The degree of non-specific extension (primer-dimer or non-target copying) can also affect amplification efficiency. For this reason, primers are selected to have low self- or cross-complementarity, particularly at the 3' ends of the sequence. Long homopolymer tracts and high GC content are avoided to reduce spurious primer extension. Commercially available computer software can aid in this aspect of the design. Available computer programs include MacDNA-SIS™ 2.0 (Hitachi Software Engineering American Ltd.) and OLIGO ver. 6.6 (Molecular Biology Insights; Cascade, Colo.).

Those having an ordinary level of skill in the art will appreciate that hybridization involves the association of two single strands of complementary nucleic acid to form a hydrogen bonded double strand. It is implicit that if one of the two strands is wholly or partially involved in a hybrid, then that strand will be less able to participate in formation of a new hybrid. By designing primers and probes so that substantial portions of the sequences of interest are single stranded, the rate and extent of hybridization may be greatly increased. If the target is an integrated genomic sequence, then it will naturally occur in a double stranded form (as is the case with the product of the polymerase chain reaction). These double-stranded targets are naturally inhibitory to hybridization with a probe and require denaturation prior to the hybridization step.

The rate at which a polynucleotide hybridizes to its target is a measure of the thermal stability of the target secondary structure in the target binding region. The standard measurement of hybridization rate is the $C_0 t_{1/2}$ which is measured as moles of nucleotide per liter multiplied by seconds. Thus, it is the concentration of probe multiplied by the time at which 50% of maximal hybridization occurs at that concentration. This value is determined by hybridizing various amounts of polynucleotide to a constant amount of target for a fixed time. The $C_0 t_{1/2}$ is found graphically by standard procedures familiar to those having an ordinary level of skill in the art.

Preferred Domains for Amplification Oligonucleotides and Hybridization Probes

The genomic sequences presented in Table 1 represent target domains of various amplification and detection systems disclosed herein for amplifying and detecting CHIKV nucleic acid. More specifically, the entries in Table 1 represent sequences within which the CHIKV nucleic acid can be amplified and detected. This may be accomplished, for example, using an opposed set of two primers, where the target-complementary 3' terminal sequence (i.e., the substrate for extension by a DNA polymerase) of the first primer consists of a sequence complementary to at least 15 contiguous bases of a sequence appearing in the table. Of course, the ordinary skilled artisan will appreciate that variable length ranges are also workable. For example preferred length ranges include 15-48 contiguous bases, more preferably 15-40 contiguous bases, more preferably 17-40 contiguous bases, more preferably 28-40 contiguous bases, or 18-31 bases of a sequence appearing in the table. The extension product of the first primer, using as a template one of the sequences in the table, defines the target for the second primer. Thus, the target-complementary sequence of a second primer may consist of a sequence complementary to an extension product of the first primer when using a sequence in the table as a template. Preferred length ranges for the second primer are generally similar to those used for the first primer. Again, the second primer generally will have at least 15 contiguous bases of complementarity with its target strand. Second primers in the range of 27-34 contiguous bases, and 17-24 contiguous bases of complementarity have been used with good results, and so also are preferred. Again, it is generally preferred for the target-complementary 3' terminal sequences (i.e., the substrate for extension by a DNA polymerase) of all primers to have at least 15 contiguous bases of sequence match to their target sequences. The target sequences may be defined by the sequences disclosed herein, or by their complements (as indicated). Of course, either primer may include at its 5'-end additional bases (e.g., a phage promoter sequence) that are not complementary to the CHIKV target sequence. In certain applications, the sequences appearing in the table correspond to the sequences of amplicons synthesized by the methods described below. In preferred embodiments, primer binding sites for the two opposed primers do not share in common any position along the CHIKV target nucleic acid or its complement. Stated differently, in embodiments wherein amplification is effected by extension of a primer (i.e., as distinguished from a ligase-mediated reaction) no base position (or the complement thereof) along the sequence of the CHIKV target nucleic acid is common to both of the opposed primers.

Although the entries in the Table 1 are presented as DNA sequences, it is to be understood that the CHIKV genomic sequence to be amplified is an RNA sequence. The compositions and methods described herein are intended to embrace RNA and DNA equivalents (i.e., polynucleotides having U and T bases substituted for one another).

TABLE 1

Preferred Domains for Amplifying and Detecting CHIKV Nucleic Acids

| System | Sequence | Identifier |
|---|---|---|
| 1 | NACATGCAGGGTGCCTAAAGCAAGGAACCCCACCGTGACGTACG GGAAAAACCAAGTCATCATGCTNCTGTATCCTGACCACCCAACAC TCCTGTCCTACCGGAATATGGGAGAAGAACCAAACTATCAAGAA GAGTGGGTGANGCATAAGA | SEQ ID NO: 1 |
| 2 | TGGGAGAAGAACCAAACTATCAAGAAGAGTGGGTGANGCATAAG AAGGAAGTCNNGNTAACCGTGCCGACTGAAGGGCTCGAGGTCAC GTGGGGCAACAACGAGCCGTANAAGTATTGGCCGCAGTTATCTA CAAACGGTACAGCCCA | SEQ ID NO: 2 |
| 3 | TAAGTANGACCTTGAATGCGCGCAGATACCCGTGCACATGAAGTC CGACGCTTCGAAGTTCACCCATGAGAAACCGGAGGGGTACTACA ACTGGCACCACGGAGCAGTACAGTACTCAGGAGGCCGGTTCACC ATCCCTACAGGTGCNGGCAAACC | SEQ ID NO: 3 |
| 4 | CGGTGCCCACACTGTGAGCGCGTACGAACACGTAACAGTGATCCC GAACACGGTGGGAGTACCGTATAAGACTCTAGTCAANAG | SEQ ID NO: 4 |
| 5 | CAGNGGGGATGTGCATGTGTGCACGACGCAGATGCATNACACCG TANGAACTGACACCAGGAGCTACCGTCCCTTTCCTGCTTAGCCTA ATATGCTGCATNAGAACAG | SEQ ID NO: 5 |
| 6 | TACCTGACTACAGCTGTAAGGTCTTCACCGGCGTCTACCCATTNA TGTGGGCGGCGCCTACTGCTTCTGCGACNCTGAAAANACGCANT TGAGCGAAGCACATGTGGAGAAGTCCGAATCATGCAAAACAGAA | SEQ ID NO: 6 |
| 7 | AAANTGGGCNGATGAGCAGGTACTGAAGGCTAAGAACATAGGAT TATGTTCAACAGACCTGACGGAAGGTAGACGAGGCAANTTGTCT | SEQ ID NO: 7 |
| 8 | GAGAAAGCTNGCATCTGCCGCAGGAAAAGTCCTGGACAGAAACA TCTCTGGAAAGATCGGGGACTTACAAGCNGTNATGGC | SEQ ID NO: 8 |
| 9 | GGCAANCTNAGCTTCACATGCCGCTGTGANACAGTGGTTTCGTGT GAGGGCTACGTCGTTAAGAGAATAACGATGAGCCCAGGCCTTTAT GGAAAAACCACAGGGTATGCGGTAACCCACCACGCAGACGGATT CNTG | SEQ ID NO: 9 |
| 10 | AAACCACAGGGTATGCGGTAACCCACCACGCAGACGGATTCNTG ATGTGCAAGACTACCGACACGGTTGACGGCGAAAGAGTGTCATTC TCGGTGTGCACNTACGTGCCGGCGACCATTTGTGATCAAATGACC GGCATCCTTGCTACAGA | SEQ ID NO: 10 |
| 11 | GCAAGACTACCGACACGGTTGACGGCGAAAGAGTGTCATTCTCG GTGTGCACNTACGTGCCGGCGACCATTTGTGATCAAATGACCGGC ATCCTTGCTACAGAAGTCACGCCGGAGGATGCACAGAAGCTGTTG GTGGGGCTGAAC | SEQ ID NO: 11 |
| 12 | GAACACACTACAGAATGTACTGGCAGCAGCCACGAAAAGNAACT GCAACGTCACACAGATGAGGGAATTACCCACTTTGGACTCAGCAG TATTCAAC | SEQ ID NO: 12 |
| 13 | AAGAACACTNACCTGCTGCTGTCTATGGGCATTNAAGAAGCAGA AAACACACACGGTCTACAAGAGGCCTGATACCCAGTCAATNCAG AAG | SEQ ID NO: 13 |
| 14 | ACCCGAAGCAGTGCGGCTTCTTCAATATGATGCAGATGAAAGTCA ACTANAATCANAACATCTGCACCCAAGTGTACCACAAAAGTATCT CCAGGCGGTGTACACTGCCTGTGACNGCCATTGTGTCATCGTTGC ATTACGAAGGCAAAATGCGCACTACGAATGAG | SEQ ID NO: 14 |
| 15 | NGGTAATGTCCATGGCCACCTTTGCAAGCTCCAGATCCAACTTCG AGAAGCTCAGAGGACCCGTCATAACTTTGTACGGCGGTCCTAAAT AGGTACGCACTACAGCTACCTATTTTGNCA | SEQ ID NO: 15 |

Table 2 presents highly preferred target domains of various amplification and detection systems disclosed herein for amplifying and detecting CHIKV nucleic acid. The sequences appearing in Table 2 are fully contained within the target domains that appear in Table 1. The entries in Table 2 represent sequences within which the CHIKV nucleic acid can be amplified and detected. Again, this may be accomplished, for example, using an opposed set of two primers. Length ranges are given herein, but embrace situations wherein the target-complementary sequence of the first primer consists of a sequence complementary to about 15-40, more preferably 15-30, more preferably 17-30, or 18-31 contiguous bases of a sequence appearing in the table. In a highly preferred embodiment, the target-complementary sequence of the first primer consists of 18-31 bases fully complementary to the 3' terminus of a sequence appearing in the table. The target-complementary sequence of a second primer may consist of a sequence fully complementary to about 18-31 bases of an extension product of the first primer when using a sequence in the table as a template. By this description is meant that the 5'-end of the target-complementary sequence of the first primer can correspond to (i.e., is complementary to) the 3' terminal base of the sequence in the table. Further, the 5'-end of the target-complementary sequence of the second primer can correspond to (i.e., is homologous to) the 5' terminal base of a sequence presented in the table. Of course, either primer may include at its 5'-end additional bases (e.g., a phage promoter sequence) that are not complementary to the CHIKV target sequence.

In certain applications, the sequences appearing in the table correspond to the sequences of amplicons synthesized by the methods described below.

Although the entries in the Table 2 are presented as DNA sequences, it is to be understood that the CHIKV genomic sequence to be amplified, and amplification products synthesized therefrom can be RNA sequences. The compositions and methods described herein are intended to embrace RNA and DNA equivalents (i.e., polynucleotides having U and T bases substituted for one another).

TABLE 2

Highly Preferred Domains for Amplifying and Detecting CHIKV Nucleic Acids

| System | Sequence | Identifier |
|---|---|---|
| 1 | GTGCCTAAAGCAAGGAACCCCACCGTGACGTACGGGAAAA ACCAAGTCATCATGCTNCTGTATCCTGACCACCCAACACTC CTGTCCTACCGGAATATGGGAGAAGAACCAAACTATCAAG AAGAGTGGGTG | SEQ ID NO: 16 |
| 2 | CCAAACTATCAAGAAGAGTGGGTGANGCATAAGAAGGAAG TCNNGNTAACCGTGCCGACTGAAGGGCTCGAGGTCACGTG GGGCAACAACGAGCCGTANAAGTATTGGCCGCAGTTATCT ACAAACG | SEQ ID NO: 17 |
| 3 | CTTGAATGCGCGCAGATACCCGTGCACATGAAGTCCGACG CTTCGAAGTTCACCCATGAGAAACCGGAGGGGTACTACAA CTGGCACCACGGAGCAGTACAGTACTCAGGAGGCCGGTTC ACCATCCCTACAGGTG | SEQ ID NO: 18 |
| 4 | ACTGTGAGCGCGTACGAACACGTAACAGTGATCCCGAACA CGGTGGGAGTACCGTATAAGACTC | SEQ ID NO: 19 |
| 5 | GTGCATGTGTGCACGACGCAGATGCATNACACCGTANGAA CTGACACCAGGAGCTACCGTCCCTTTCCTGCTTAGCCTAAT ATGCTGC | SEQ ID NO: 20 |
| 6 | CAGCTGTAAGGTCTTCACCGGCGTCTACCCATTNATGTGGG GCGGCGCCTACTGCTTCTGCGACNCTGAAAANACGCANTT GAGCGAAGCACATGTGGAGAAGTCCGAATCATGC | SEQ ID NO: 21 |
| 7 | GATGAGCAGGTACTGAAGGCTAAGAACATAGGATTATGTT CAACAGACCTGACGGAAGGTAGACGAGG | SEQ ID NO: 22 |
| 8 | GCATCTGCCGCAGGAAAAGTCCTGGACAGAAACATCTCTG GAAAGATCGGGGACTTACAAGC | SEQ ID NO: 23 |
| 9 | GCTTCACATGCCGCTGTGANACAGTGGTTTCGTGTGAGGGC TACGTCGTTAAGAGAATAACGATGAGCCCAGGCCTTTATG GAAAAACCACAGGGTATGCGGTAACCCACCACGCAGA | SEQ ID NO: 24 |
| 10 | GTATGCGGTAACCCACCACGCAGACGGATTCNTGATGTGC AAGACTACCGACACGGTTGACGGCGAAAGAGTGTCATTCT CGGTGTGCACNTACGTGCCGGCGACCATTTGTGATCAAATG ACCGGCATCC | SEQ ID NO: 25 |
| 11 | GACACGGTTGACGGCGAAAGAGTGTCATTCTCGGTGTGCA CNTACGTGCCGGCGACCATTTGTGATCAAATGACCGGCATC CTTGCTACAGAAGTCACGCCGGAGGATGCACAGAAGCTGT TGG | SEQ ID NO: 26 |
| 12 | CAGAATGTACTGGCAGCAGCCACGAAAAGNAACTGCAACG TCACACAGATGAGGGAATTACCCACTTTGGACTCAGC | SEQ ID NO: 27 |
| 13 | ACCTGCTGCTGTCTATGGGCATTNAAGAAGCAGAAAACAC ACACGGTCTACAAGAGGCCTGATACCCAGTC | SEQ ID NO: 28 |
| 14 | GTGCGGCTTCTTCAATATGATGCAGATGAAAGTCAACTANA ATCANAACATCTGCACCCAAGTGTACCACAAAAGTATCTCC AGGCGGTGTACACTGCCTGTGACNGCCATTGTGTCATCGTT GCATTACGAAGGCAAAATGCGCAC | SEQ ID NO: 29 |
| 15 | CATGGCCACCTTTGCAAGCTCCAGATCCAACTTCGAGAAGC TCAGAGGACCCGTCATAACTTTGTACGGCGGTCCTAAATAG GTACGCACTACAGCTACC | SEQ ID NO: 30 |

Table 3 presents the sequences of preferred domains for target-complementary sequences of first strand amplification oligonucleotides (e.g., primers). Indeed, first strand amplification oligonucleotides used for amplifying CHIKV nucleic acids preferably have target-complementary sequences fully contained within a sequence appearing in Table 3. Of course, the first strand primer may include at its 5'-end additional bases (e.g., a phage promoter sequence) that are not complementary to the CHIKV target sequence. Preferred first strand amplification oligonucleotides or primers have target complementary sequences that consist of 18-31 contiguous bases contained within the sequences presented in Table 3.

fication oligonucleotides used for amplifying CHIKV nucleic acids preferably have target-complementary sequences fully contained within a sequence appearing in Table 4. Of course, the second strand primer may include at its 5'-end additional bases (e.g., a phage promoter sequence) that are not complementary to the CHIKV target sequence. Additionally, when used for practicing certain amplification procedures based on the use of a single extendable primer, the amplification oligonucleotide can also have disposed at its 3'-end a chemical moiety that prevents extension by a DNA polymerizing enzyme. Preferred second strand amplification oligonucleotides or primers have target complemen-

TABLE 3

Preferred First Strand Amplification Oligonucleotide Domains

| System | Sequence | Identifier |
|---|---|---|
| 1 | TCTTATGCNTCACCCACTCTTCTTGATAGTTTGGTTCTTCTCCC | SEQ ID NO: 31 |
| 2 | TGGGCTGTACCGTTTGTAGATAACTGCGGCCAATACTTNTACGGCT | SEQ ID NO: 32 |
| 3 | CCGGCCTCCTGAGTACTGTACTGCTCCGTGGTGCCAGTTGTAG | SEQ ID NO: 33 |
| 3 | GGTTTGCCNGCACCTGTAGGGATGGTGAACCGGCCTCCTG | SEQ ID NO: 34 |
| 4 | CTNTTGACTAGAGTCTTATACGGTACTCCCACCGTGTTCGGGA | SEQ ID NO: 35 |
| 5 | CTGTTCTNATGCAGCATATTAGGCTAAGCAGGAAAGGGACGGTAGCTCCTG | SEQ ID NO: 36 |
| 6 | TTCTGTTTTGCATGATTCGGACTTCTCCACATGTGCT | SEQ ID NO: 37 |
| 7 | AGACAANTTGCCTCGTCTACCTTCCGTCAGGTCTGTTGAA | SEQ ID NO: 38 |
| 8 | GCCATNACNGCTTGTAAGTCCCCGATCTTTCCAGAGATGTTT | SEQ ID NO: 39 |
| 9 | CTGCGTGGTGGGTTACCGCATACCCTGTGGTTTTTCCATA | SEQ ID NO: 40 |
| 9 | CANGAATCCGTCTGCGTGGTGGGTTACCGCATACCCTGTGGTTTT | SEQ ID NO: 41 |
| 10 | CCGGTCATTTGATCACAAATGGTCGCCGGCACGTANGTGCAC | SEQ ID NO: 42 |
| 10 | TCTGTAGCAAGGATGCCGGTCATTTGATCACAAATGGTCGCCGGCAC | SEQ ID NO: 43 |
| 11 | TCAGCCCCACCAACAGCTTCTGTGCATCCTCCGGCGTGACT | SEQ ID NO: 44 |
| 11 | TTCAGCCCCACCAACAGCTTCTGTGCATCCTCCGGCGTGACTT | SEQ ID NO: 45 |
| 12 | GTTGAATACTGCTGAGTCCAAAGTGGGTAATTCCCTCATCTGTG | SEQ ID NO: 46 |
| 13 | CTTCTGNATTGACTGGGTATCAGGCCTCTTGTAGACCGTGTGTGTT | SEQ ID NO: 47 |
| 14 | CTCATTCGTAGTGCGCATTTTGCCTTCGTAATGCAACGATGACACAAT | SEQ ID NO: 48 |
| 14 | CACAATGGCNGTCACAGGCAGTGTACACCGCCTGGAGA | SEQ ID NO: 49 |
| 15 | TGNCAAAATAGGTAGCTGTAGTGCGTACCTATTTAGGACCGCCGTAC | SEQ ID NO: 50 |

Table 4 presents the sequences of preferred domains for target-complementary sequences of second strand amplification oligonucleotides (e.g., primers). Second strand amplitary sequences that consist of 15-34, or more preferably 17-34 contiguous bases contained within the sequences presented in Table 4.

TABLE 4

Preferred Second Strand Amplification Oligonucleotide Domains

| System | Sequence | Identifier |
|---|---|---|
| 1 | CATCATGCTNCTGTATCCTGACCACCCAACACTCCTGTCC | SEQ ID NO: 51 |
| 1 | NACATGCAGGGTGCCTAAAGCAAGGAACCCCACCGTGA | SEQ ID NO: 52 |
| 2 | GGGAGAAGAACCAAACTATCAAGAAGAGTGGGTGANGCATAAGA | SEQ ID NO: 53 |
| 3 | TAAGTANGACCTTGAATGCGCGCAGATACCCGTGCACAT | SEQ ID NO: 54 |
| 3 | GATACCCGTGCACATGAAGTCCGACGCTTCGAAGTTCACCCATG | SEQ ID NO: 55 |
| 4 | CGGTGCCCACACTGTGAGCGCGTACGAACACGTAACAGTGA | SEQ ID NO: 56 |
| 5 | CAGNGGGGATGTGCATGTGTGCACGACGCAGATGCATNACACCG | SEQ ID NO: 57 |
| 6 | TACCTGACTACAGCTGTAAGGTCTTCACCGGCGTCTAC | SEQ ID NO: 58 |
| 7 | AAANTGGGCNGATGAGCAGGTACTGAAGGCTAAGAACAT | SEQ ID NO: 59 |
| 8 | GAGAAAGCTNGCATCTGCCGCAGGAAAAGTCCTGGACAG | SEQ ID NO: 60 |
| 9 | GGCAANCTNAGCTTCACATGCCGCTGTGANACAGTGGT | SEQ ID NO: 61 |
| 10 | AAACCACAGGGTATGCGGTAACCCACCACGCAGACGGATTCNT | SEQ ID NO: 62 |
| 11 | CAAGACTACCGACACGGTTGACGGCGAAAGAGTGTCATTCTC | SEQ ID NO: 63 |
| 11 | GCGAAAGAGTGTCATTCTCGGTGTGCACNTACGTGCCG | SEQ ID NO: 64 |
| 12 | GAACACACTACAGAATGTACTGGCAGCAGCCACGAAAAGN | SEQ ID NO: 65 |
| 12 | ACTACAGAATGTACTGGCAGCAGCCACGAAAAGNAACTGCAAC | SEQ ID NO: 66 |
| 13 | AAGAACACTNACCTGCTGCTGTCTATGGGCATTNAAG | SEQ ID NO: 67 |
| 14 | ACCCGAAGCAGTGCGGCTTCTTCAATATGATGCAGATGA | SEQ ID NO: 68 |
| 15 | NGGTAATGTCCATGGCCACCTTTGCAAGCTCCAGATCCA | SEQ ID NO: 69 |

Table 5 presents the sequences of preferred domains for hybridization detection probes. Because it is possible to detect CHIKV nucleic acid amplification products using either of two complementary strands, the complements of the sequences appearing in the table also are preferred domains for hybridization detection probes. Highly preferred probes have target-complementary sequences of 11-24 contiguous bases, more preferably 15-24 contiguous bases, or still more preferably 16-24 contiguous bases fully contained within a sequence, or the complement thereof, appearing in Table 5. A lower length of 15 contiguous bases is generally preferred.

Although the entries in the Table 5 are presented as DNA sequences, it is to be understood that the CHIKV genomic sequence to be amplified is an RNA sequence, and that probes can include RNA and DNA equivalents (i.e., polynucleotides having U and T bases substituted for one another).

TABLE 5

Preferred Hybridization Probe Domains

| System | Sequence | Identifier |
|---|---|---|
| 1 | ACCCAACACTCCTGTCCTACCGGAATATGGGAGAAGAAC | SEQ ID NO: 70 |
| 1 | CCTGTCCTACCGGAATATGGGAGAAGAACCAAACTATCA | SEQ ID NO: 71 |
| 2 | CTGAAGGGCTCGAGGTCACGTGGGGCAACAACGAGCCGTANA | SEQ ID NO: 72 |
| 3 | GTTCACCCATGAGAAACCGGAGGGGTACTACAACTGGCACCACG | SEQ ID NO: 73 |

TABLE 5-continued

Preferred Hybridization Probe Domains

| System | Sequence | Identifier |
|---|---|---|
| 4 | GTACGAACACGTAACAGTGATCCCGAACACGGTGGGAGTA | SEQ ID NO: 74 |
| 5 | ACCGTANGAACTGACACCAGGAGCTACCGTCCCTTTC | SEQ ID NO: 75 |
| 6 | GGGGCGGCGCCTACTGCTTCTGCGACNCTGAAAA | SEQ ID NO: 76 |
| 7 | TAAGAACATAGGATTATGTTCAACAGACCTGACGGAAG | SEQ ID NO: 77 |
| 8 | CAGGAAAAGTCCTGGACAGAAACATCTCTGGAAAGATC | SEQ ID NO: 78 |
| 9 | TGAGGGCTACGTCGTTAAGAGAATAACGATGAGCCCAG | SEQ ID NO: 79 |
| 10 | GCGAAAGAGTGTCATTCTCGGTGTGCACNTACGTGCCG | SEQ ID NO: 80 |
| 11 | GTGCCGGCGACCATTTGTGATCAAATGACCGGCATCCTT | SEQ ID NO: 81 |
| 12 | CGAAAAGNAACTGCAACGTCACACAGATGAGGGAATTAC | SEQ ID NO: 82 |
| 13 | GGGCATTNAAGAAGCAGAAAACACACACGGTCTACAAG | SEQ ID NO: 83 |
| 14 | TANAATCANAACATCTGCACCCAAGTGTACCACAAAAGTA | SEQ ID NO: 84 |
| 15 | TCCAACTTCGAGAAGCTCAGAGGACCCGTCATAACTTTGT | SEQ ID NO: 85 |

Table 6 presents the sequences of preferred domains for target-complementary sequences of capture oligonucleotides. Preferred target capture oligonucleotides have target-complementary sequences consisting of 28-51 contiguous bases fully contained within a sequence appearing in Table 6. Highly preferred target capture oligonucleotides have the sequences of SID ID NO:188-191, or the complements thereof. These sequences are also preferred for use as hybridization probes, as well as for use as primers. RNA and DNA equivalent versions of these polynucleotide sequences, as well as analogs incorporating 2'-Ome and PNA (protein nucleic acid), are embraced by the invention.

TABLE 6

Preferred Capture Oligonucleotide Domains

| Sequence | Identifier |
|---|---|
| UUGUGUAGAACAGACUUGUACGCGGAAUUCGGCGCUGGC UANGGCCGU | SEQ ID NO: 86 |
| GGAUACAACUGCAUCUAUGAUCUUCACUUCCAUGUUCAU CCAAGUNGCNCA | SEQ ID NO: 87 |
| GCAAACGCCUCGUCUACGUACAACACGUCGACUGGUCUG UUGCAUCCA | SEQ ID NO: 88 |
| AGUNANNUUNUUUCCUUGGUAAAGGACGCGGAGCUUAGC UGAUGCN | SEQ ID NO: 89 |

Preferred Amplification Primers

Primers useful for conducting amplification reactions can have different lengths to accommodate the presence of extraneous sequences that do not participate in target binding, and that may not substantially affect amplification or detection procedures. For example, promoter-primers useful for performing amplification reactions in accordance with the invention have at least a minimal sequence that hybridizes to the CHIKV target nucleic acid, and a promoter sequence positioned upstream of that minimal sequence. However, insertion of sequences between the target binding sequence and the promoter sequence could change the length of the primer without compromising its utility in the amplification reaction. Additionally, the lengths of the amplification primers and detection probes are matters of choice as long as the sequences of these oligonucleotides conform to the minimal essential requirements for hybridizing the desired complementary sequence.

Tables 7, 8 and 9 present specific examples of preferred primer sequences for amplifying CHIKV nucleic acids. Tables 7 and 8 present primer sequences complementary to CHIKV sequences on one strand of nucleic acid. Table 7 presents preferred CHIKV target-complementary primer sequences, while Table 8 presents the full sequences for promoter-primers that were used during development of the invention. Notably, amplification oligonucleotides in Tables 7 and 8, and the amplification oligonucleotides in Table 9 are complementary to opposite strands of the CHIKV nucleic acid. As indicated above, all promoter-primers included sequences complementary to a CHIKV target sequence at their 3' ends, and a T7 promoter sequence at their 5' ends. Thus, the oligonucleotides in Table 8 correspond to the oligonucleotides in Table 7 further including an upstream promoter sequence which is not present in the CHIKV target nucleic acid. All promoter-primers included a T7 promoter sequence AATTTAATACGACTCACTATAG GGAGA (SEQ ID NO:90) upstream of the target-complementary sequence.

As discussed herein, amplification oligonucleotides useful for amplifying CHIKV nucleic acids also can include nucleotide analogs. For example, the amplification oligonucleotides may include substitution of a hypoxanthine base analog for an adenine base.

TABLE 7

Target-Binding Sequences of Amplification Primers

| System | Sequence | Identifier |
|---|---|---|
| 1 | CACCCACTCTTCTTGATAGTTTGG | SEQ ID NO: 91 |
| 2 | CGTTTGTAGATAACTGCGGCCAATAC | SEQ ID NO: 92 |
| 3 | GAGTACTGTACTGCTCCGTGGTG | SEQ ID NO: 93 |

TABLE 7-continued

| Target-Binding Sequences of Amplification Primers | | |
|---|---|---|
| System | Sequence | Identifier |
| 3 | CACCTGTAGGGATGGTGAAC | SEQ ID NO: 94 |
| 4 | GAGTCTTATACGGTACTCCCACC | SEQ ID NO: 95 |
| 5 | GCAGCATATTAGGCTAAGCAGGAAAGGG ACG | SEQ ID NO: 96 |
| 6 | GCATGATTCGGACTTCTC | SEQ ID NO: 97 |
| 7 | CCTCGTCTACCTTCCGTCAG | SEQ ID NO: 98 |
| 8 | GCTTGTAAGTCCCCGATCTTTCC | SEQ ID NO: 99 |
| 9 | GGTTACCGCATACCCTGTGG | SEQ ID NO: 100 |
| 9 | TCTGCGTGGTGGGTTACCGCATACC | SEQ ID NO: 101 |
| 10 | GATCACAAATGGTCGCCGGCAC | SEQ ID NO: 102 |
| 10 | GGATGCCGGTCATTTGATCACAAATGG | SEQ ID NO: 103 |

TABLE 7-continued

| Target-Binding Sequences of Amplification Primers | | |
|---|---|---|
| System | Sequence | Identifier |
| 11 | CAACAGCTTCTGTGCATCCTC | SEQ ID NO: 104 |
| 11 | CCAACAGCTTCTGTGCATCCTCC | SEQ ID NO: 105 |
| 12 | GCTGAGTCCAAAGTGGGTAATTCC | SEQ ID NO: 106 |
| 13 | GACTGGGTATCAGGCCTCTTGTAGAC | SEQ ID NO: 107 |
| 14 | GTGCGCATTTTGCCTTCGTAATGCAACG | SEQ ID NO: 108 |
| 14 | GTCACAGGCAGTGTACAC | SEQ ID NO: 109 |
| 15 | GGTAGCTGTAGTGCGTACCTATTTAGG | SEQ ID NO: 110 |

The sequence of the T7 promoter sequence in Table 8 is indicated by lowercase lettering. The target-complementary portions of the primers in Table 8 are indicated by uppercase lettering. Preferred primers include a CHIKV target-complementary sequence shown in the table.

TABLE 8

| T7 Promoter-Primer Sequences | | |
|---|---|---|
| System | Sequence | Identifier |
| 1 | aatttaatacgactcactatagggagaCACCCACTCTTCTTGATAGTTTGG | SEQ ID NO: 111 |
| 2 | aatttaatacgactcactatagggagaCGTTTGTAGATAACTGCGGCCAATAC | SEQ ID NO: 112 |
| 3 | aatttaatacgactcactatagggagaGAGTACTGTACTGCTCCGTGGTG | SEQ ID NO: 113 |
| 3 | aatttaatacgactcactatagggagaCACCTGTAGGGATGGTGAAC | SEQ ID NO: 114 |
| 4 | aatttaatacgactcactatagggagaGAGTCTTATACGGTACTCCCACC | SEQ ID NO: 115 |
| 5 | aatttaatacgactcactatagggagaGCAGCATATTAGGCTAAGCAGGAAAGGGA CG | SEQ ID NO: 116 |
| 6 | aatttaatacgactcactatagggagaGCATGATTCGGACTTCTC | SEQ ID NO: 117 |
| 7 | aatttaatacgactcactatagggagaCCTCGTCTACCTTCCGTCAG | SEQ ID NO: 118 |
| 8 | aatttaatacgactcactatagggagaGCTTGTAAGTCCCCGATCTTTCC | SEQ ID NO: 119 |
| 9 | aatttaatacgactcactatagggagaGGTTACCGCATACCCTGTGG | SEQ ID NO: 120 |
| 9 | aatttaatacgactcactatagggagaTCTGCGTGGTGGGTTACCGCATACC | SEQ ID NO: 121 |
| 10 | aatttaatacgactcactatagggagaGATCACAAATGGTCGCCGGCAC | SEQ ID NO: 122 |
| 10 | aatttaatacgactcactatagggagaGGATGCCGGTCATTTGATCACAAATGG | SEQ ID NO: 123 |
| 11 | aatttaatacgactcactatagggagaCAACAGCTTCTGTGCATCCTC | SEQ ID NO: 124 |
| 11 | aatttaatacgactcactatagggagaCCAACAGCTTCTGTGCATCCTCC | SEQ ID NO: 125 |
| 12 | aatttaatacgactcactatagggagaGCTGAGTCCAAAGTGGGTAATTCC | SEQ ID NO: 126 |
| 13 | aatttaatacgactcactatagggagaGACTGGGTATCAGGCCTCTTGTAGAC | SEQ ID NO: 127 |
| 14 | aatttaatacgactcactatagggagaGTGCGCATTTTGCCTTCGTAATGCAACG | SEQ ID NO: 128 |
| 14 | aatttaatacgactcactatagggagaGTCACAGGCAGTGTACAC | SEQ ID NO: 129 |
| 15 | aatttaatacgactcactatagggagaGGTAGCTGTAGTGCGTACCTATTTAGG | SEQ ID NO: 130 |

Table 9 presents CHIKV target-complementary oligonucleotide sequences that were used for amplifying CHIKV nucleic acid sequences. The amplification oligonucleotides presented in Table 9 include target-complementary sequences that can hybridize to extension products of the amplification oligonucleotides listed in Tables 7 and 8.

TABLE 9

Sequences of Amplification Primers

| System | Sequence | Identifier |
|---|---|---|
| 1 | CTGTATCCTGACCACCCAAC | SEQ ID NO: 131 |
| 1 | GTGCCTAAAGCAAGGAAC | SEQ ID NO: 132 |
| 2 | CCAAACTATCAAGAAGAGTGGGTG | SEQ ID NO: 133 |
| 3 | CTTGAATGCGCGCAGATAC | SEQ ID NO: 134 |
| 3 | CACATGAAGTCCGACGCTTCGAAG | SEQ ID NO: 135 |
| 4 | ACTGTGAGCGCGTACGAACAC | SEQ ID NO: 136 |
| 5 | GTGCATGTGTGCACGACGCAGATG | SEQ ID NO: 137 |
| 6 | CAGCTGTAAGGTCTTCAC | SEQ ID NO: 138 |
| 7 | GATGAGCAGGTACTGAAGG | SEQ ID NO: 139 |
| 8 | GCATCTGCCGCAGGAAAAG | SEQ ID NO: 140 |
| 9 | GCTTCACATGCCGCTGTG | SEQ ID NO: 141 |
| 10 | GTATGCGGTAACCCACCACGCAG | SEQ ID NO: 142 |
| 11 | GACACGGTTGACGGCGAAAGAG | SEQ ID NO: 143 |
| 11 | GTCATTCTCGGTGTGCAC | SEQ ID NO: 144 |
| 12 | CAGAATGTACTGGCAGCAGC | SEQ ID NO: 145 |
| 12 | GTACTGGCAGCAGCCACGAAAAG | SEQ ID NO: 146 |
| 13 | ACCTGCTGCTGTCTATG | SEQ ID NO: 147 |
| 14 | GTGCGGCTTCTTCAATATG | SEQ ID NO: 148 |
| 15 | CATGGCCACCTTTGCAAGC | SEQ ID NO: 149 |

Preferred sets of primers for amplifying CHIKV sequences include a first primer that hybridizes a CHIKV target sequence (such as one of the primers listed in Table 8) and a second primer that is complementary to the sequence of an extension product of the first primer (such as one of the primer sequences listed in Table 9). In a highly preferred embodiment, the first primer is a promoter-primer that includes a T7 promoter sequence at its 5' end.

Preferred Detection Probes

Another aspect of the invention relates to oligonucleotides that can be used as hybridization probes for detecting CHIKV nucleic acids. Methods for amplifying a target nucleic acid sequence present in the nucleic acid of CHIKV can include an optional further step for detecting amplicons. This procedure preferably involves a step for contacting a test sample with a hybridization assay probe that preferentially hybridizes to the target nucleic acid sequence, or the complement thereof, under stringent hybridization conditions, thereby forming a probe:target duplex that is stable for detection. Next there is a step for determining whether the hybrid is present in the test sample as an indication of the presence or absence of CHIKV nucleic acids in the test sample. This may involve detecting the probe:target duplex, and preferably involve homogeneous assay systems.

Hybridization assay probes useful for detecting CHIKV nucleic acid sequences include a sequence of bases substantially complementary to a CHIKV target nucleic acid sequence. Thus, probes of the invention hybridize one strand of a CHIKV target nucleic acid sequence, or the complement thereof. These probes may optionally have additional bases outside of the targeted nucleic acid region which may or may not be complementary to CHIKV nucleic acid.

Preferred probes are sufficiently homologous to the target nucleic acid to hybridize under stringent hybridization conditions corresponding to about 42° C., or more preferably about 60° C. when the salt concentration is in the range of 0.6-0.9 M. Preferred salts include lithium chloride, but other salts such as sodium chloride and sodium citrate also can be used in the hybridization solution. Example high stringency hybridization conditions are alternatively provided by about 42° C., or more preferably about 60° C., and 0.48 M sodium phosphate buffer, 0.1% sodium dodecyl sulfate, and 1 mM each of EDTA and EGTA, or by 0.6 M LiCl, 1% lithium lauryl sulfate, 60 mM lithium succinate and 10 mM each of EDTA and EGTA.

Probes in accordance with the invention have sequences complementary to, or corresponding to different domains of the CHIKV genome. Certain probes that are preferred for detecting CHIKV nucleic acid sequences have a probe sequence, which includes the target-complementary sequence of bases together with any base sequences that are not complementary to the nucleic acid that is to be detected, in the length range of from 10-100 nucleotides. Certain specific probes that are preferred for detecting CHIKV nucleic acid sequences have target-complementary sequences in the length range of from 15-30, from 16-24, from 18-22 or from 18-20 nucleotides. Of course, these target-complementary sequences may be linear sequences, or may be contained in the structure of a molecular beacon or other construct having one or more optional nucleic acid sequences that are non-complementary to the CHIKV target sequence that is to be detected. As indicated above, probes may be made of DNA, RNA, a combination DNA and RNA, a nucleic acid analog, or contain one or more modified nucleosides (e.g., a ribonucleoside having a 2'-O-methyl substitution to the ribofuranosyl moiety).

Simply stated, preferred probes for detecting target nucleic acids of interest in connection with the present invention include sequences that are contained within one or more of several defined probe domains or the complements thereof, allowing for the presence of RNA and DNA equivalents, nucleotide analogs, up to 10% mismatched bases, and even up to 20% mismatched bases.

Certain preferred probes in accordance with the present invention include a detectable label. In one embodiment this label is an acridinium ester joined to the probe by means of a non-nucleotide linker. For example, detection probes can be labeled with chemiluminescent acridinium ester compounds that are attached via a linker substantially as described in U.S. Pat. No. 5,585,481; and in U.S. Pat. No. 5,639,604, particularly as described at column 10, line 6 to column 11, line 3, and in Example 8. The disclosures contained in these patent documents are hereby incorporated by reference.

Table 10 presents the base sequences of some of the hybridization probes that were used for detecting CHIKV amplicons. Since alternative probes for detecting CHIKV nucleic acid sequences can hybridize to the opposite-sense strand of CHIKV, the present invention also includes oligonucleotides that are complementary to the sequences presented in the table. Additionally, it is to be understood that the invention can be practiced using oligonucleotide hybridization probes containing RNA and DNA equivalent bases (i.e., U and T bases being substituted for one another).

TABLE 10

Target-Complementary Sequences of CHIKV Detection Probes

| System | Sequence | Identifier |
|---|---|---|
| 1 | CCUGUCCUACCGGAAUAUG | SEQ ID NO: 150 |
| 1 | CGGAAUAUGGGAGAAGAAC | SEQ ID NO: 151 |
| 2 | CGAGGUCACGUGGGGCAACAAC | SEQ ID NO: 152 |
| 3 | GAGAAACCGGAGGGGUACUACAAC | SEQ ID NO: 153 |
| 4 | GUAACAGUGAUCCCGAACA | SEQ ID NO: 154 |
| 5 | CTGACACCAGGAGCTAC | SEQ ID NO: 155 |
| 6 | CUACUGCUUCUGCGAC | SEQ ID NO: 156 |
| 7 | GGAUUAUGUUCAACAGAC | SEQ ID NO: 157 |
| 8 | CCUGGACAGAAACAUCUC | SEQ ID NO: 158 |
| 9 | GUCGUUAAGAGAAUAACG | SEQ ID NO: 159 |
| 10 | GUCAUUCUCGGUGUGCAC | SEQ ID NO: 160 |
| 11 | CCAUUUGUGAUCAAAUGAC | SEQ ID NO: 161 |
| 12 | CUGCAACGUCACACAGAUG | SEQ ID NO: 162 |
| 13 | GAAGCAGAAAACACACAC | SEQ ID NO: 163 |
| 14 | ACAUCUGCACCCAAGUGUAC | SEQ ID NO: 164 |
| 15 | AGAAGCUCAGAGGACCCGUC | SEQ ID NO: 165 |

As indicated above, any number of different backbone structures can be used as a scaffold for the nucleobase sequences of the invented hybridization probes. In certain highly preferred embodiments, the probe sequence used for detecting CHIKV amplicons includes a methoxy backbone, or at least one methoxy linkage in the nucleic acid backbone.

Selection and Use of Capture Oligonucleotides

Preferred capture oligonucleotides include a first sequence that is complementary to a CHIKV sequence (i.e., a "CHIKV target sequence") covalently attached to a second sequence (i.e., a "tail" sequence) that serves as a target for immobilization on a solid support. Any backbone to link the base sequence of a capture oligonucleotide may be used. In certain preferred embodiments the capture oligonucleotide includes at least one methoxy linkage in the backbone. The tail sequence, which is preferably at the 3' end of a capture oligonucleotide, is used to hybridize to a complementary base sequence to provide a means for capturing the hybridized target CHIKV nucleic acid in preference to other components in the biological sample.

Although any base sequence that hybridizes to a complementary base sequence may be used in the tail sequence, it is preferred that the hybridizing sequence span a length of about 5-50 nucleotide residues. Particularly preferred tail sequences are substantially homopolymeric, containing about 10 to about 40 nucleotide residues, or more preferably about 14 to about 30 residues. A capture oligonucleotide according to the present invention may include a first sequence that specifically binds a CHIKV target polynucleotide, and a second sequence that specifically binds an oligo(dT) stretch immobilized to a solid support.

Using the components illustrated in FIG. 1, one assay for detecting CHIKV sequences in a biological sample includes the steps of capturing the target nucleic acid using the capture oligonucleotide, amplifying the captured target region using at least two primers, and detecting the amplified nucleic acid by first hybridizing the labeled probe to a sequence contained in the amplified nucleic acid and then detecting a signal resulting from the bound labeled probe.

The capturing step preferably uses a capture oligonucleotide where, under hybridizing conditions, one portion of the capture oligonucleotide specifically hybridizes to a sequence in the target nucleic acid and a tail portion serves as one component of a binding pair, such as a ligand (e.g., a biotin-avidin binding pair) that allows the target region to be separated from other components of the sample. Preferably, the tail portion of the capture oligonucleotide is a sequence that hybridizes to a complementary sequence immobilized to a solid support particle. Preferably, first, the capture oligonucleotide and the target nucleic acid are in solution to take advantage of solution phase hybridization kinetics. Hybridization produces a capture oligonucleotide:target nucleic acid complex which can bind an immobilized probe through hybridization of the tail portion of the capture oligonucleotide with a complementary immobilized sequence. Thus, a complex comprising a target nucleic acid, capture oligonucleotide and immobilized probe is formed under hybridization conditions. Preferably, the immobilized probe is a repetitious sequence, and more preferably a homopolymeric sequence (e.g., poly-A, poly-T, poly-C or poly-G), which is complementary to the tail sequence and attached to a solid support. For example, if the tail portion of the capture oligonucleotide contains a poly-A sequence, then the immobilized probe would contain a poly-T sequence, although any combination of complementary sequences may be used. The capture oligonucleotide may also contain "spacer" residues, which are one or more bases located between the base sequence that hybridizes to the target and the base sequence of the tail that hybridizes to the immobilized probe. Any solid support may be used for binding the target nucleic acid:capture oligonucleotide complex. Useful supports may be either matrices or particles free in solution (e.g., nitrocellulose, nylon, glass, polyacrylate, mixed polymers, polystyrene, silane polypropylene and, preferably, magnetically attractable particles). Methods of attaching an immobilized probe to the solid support are well known. The support is preferably a particle which can be retrieved from solution using standard methods (e.g., centrifugation, magnetic attraction of magnetic particles, and the like). Preferred supports are paramagnetic monodisperse particles (i.e., uniform in size ±about 5%).

Retrieving the target nucleic acid:capture oligonucleotide: immobilized probe complex effectively concentrates the target nucleic acid (relative to its concentration in the biological sample) and purifies the target nucleic acid from amplification inhibitors which may be present in the biological sample. The captured target nucleic acid may be washed one or more times, further purifying the target, for example, by resuspending the particles with the attached target nucleic acid:capture oligonucleotide:immobilized probe complex in a washing solution and then retrieving the particles with the attached complex from the washing solution as described above. In a preferred embodiment, the capturing step takes place by sequentially hybridizing the capture oligonucleotide with the target nucleic acid and then adjusting the hybridization conditions to allow hybridization of the tail portion of the capture oligonucleotide with an immobilized complementary sequence (e.g., as described in PCT No. WO 98/50583). After the capturing step and any optional washing steps have been completed, the target nucleic acid can then be amplified. To limit the number of handling steps, the target nucleic acid optionally can be amplified without releasing it from the capture oligonucleotide.

Useful capture oligonucleotides may contain mismatches to the above-indicated sequences, as long as the mismatched sequences hybridize to the CHIKV nucleic acid containing the sequence that is to be amplified. Each capture oligonucleotide described herein included one of the CHIKV-complementary sequences presented in Table 11 linked to a poly-(dA) tail at its 3' end. All of the capture oligonucleotides also included three optional thymidine nucleotides interposed between the CHIKV-complementary sequence and the poly-(dA) tail. Both the poly-(dA) tail and three thymidine nucleotides are shown in lowercase lettering, with the CHIKV-complementary sequence being shown in uppercase lettering. The presence of these thymidine nucleotides is not believed to be essential for success of the capture procedure. The three thymidine nucleotides and the poly-(dA) tail were synthesized using DNA precursors, while the CHIKV-complementary portions of the oligonucleotides were synthesized using 2'-OMe nucleotide analogs.

TABLE 11

| CHIKV-Complementary Portions of Capture Oligonucleotides | |
|---|---|
| Sequence | Identifier |
| CAGACUUGUACGCGGAAUUCGGCGCUGG | SEQ ID NO: 166 |
| GGAUACAACUGCAUCUAUGAUCUUCACUUCCAUGUUCAU CCAAGUNGCNCA | SEQ ID NO: 167 |
| GCAAACGCCUCGUCUACGUACAACACGUCGACUGGUCUG UUGCAUCCA | SEQ ID NO: 168 |
| AGUNANNUUNUUCCUUGGUAAAGGACGCGGAGCUUAGC UGAUGCN | SEQ ID NO: 169 |

Preferred Methods for Amplifying and Detecting CHIKV Polynucleotide Sequences

Preferred methods of the present invention are described and illustrated by the Examples presented below. FIG. 1 schematically illustrates one system that may be used for detecting a target region of the CHIKV genome (shown by a thick solid horizontal line). This system includes four oligonucleotides (shown by the shorter solid lines): one capture oligonucleotide that includes a sequence that hybridizes specifically to a CHIKV sequence in the target region and a tail ("T") that hybridizes to a complementary sequence immobilized on a solid support to capture the target region present in a biological sample; one T7 promoter-primer which includes a sequence that hybridizes specifically to a CHIKV sequence in the target region and a T7 promoter sequence ("P") which, when double-stranded, serves as a functional promoter for T7 RNA polymerase; one non-T7 primer which includes a sequence that hybridizes specifically to a first strand cDNA made from the target region sequence using the T7 promoter-primer; and one labeled probe which includes a sequence that hybridizes specifically to a portion of the target region that is amplified using the two primers.

As indicated above, amplifying the captured target region using the two primers can be accomplished by any of a variety of known nucleic acid amplification reactions that will be familiar to those having an ordinary level of skill in the art. In a preferred embodiment, a transcription-associated amplification reaction, such as TMA, is employed. In such an embodiment, many strands of nucleic acid are produced from a single copy of target nucleic acid, thus permitting detection of the target by detecting probes that are bound to the amplified sequences. Preferably, transcription-associated amplification uses two types of primers (one being referred to as a promoter-primer because it contains a promoter sequence, labeled "P" in FIG. 1, for an RNA polymerase) two enzymes (a reverse transcriptase and an RNA polymerase), and substrates (deoxyribonucleoside triphosphates, ribonucleoside triphosphates) with appropriate salts and buffers in solution to produce multiple RNA transcripts from a nucleic acid template.

Referring to FIG. 1, during transcription-mediated amplification, the captured target nucleic acid is hybridized to a first primer shown as a T7 promoter-primer. Using reverse transcriptase, a complementary DNA strand is synthesized from the T7 promoter-primer using the target DNA as a template. A second primer, shown as a non-T7 primer, hybridizes to the newly synthesized DNA strand and is extended by the action of a reverse transcriptase to form a DNA duplex, thereby forming a double-stranded T7 promoter region. T7 RNA polymerase then generates multiple RNA transcripts by using this functional T7 promoter. The autocatalytic mechanism of TMA employs repetitive hybridization and polymerization steps following a cDNA synthesis step using the RNA transcripts as templates to produce additional transcripts, thereby amplifying target region-specific nucleic acid sequences.

The detecting step uses at least one detection probe that binds specifically to the amplified RNA transcripts or amplicons described above. Preferably, the detection probe is labeled with a label that can be detected using a homogeneous detection system. For example, the labeled probe can be labeled with an acridinium ester compound from which a chemiluminescent signal may be produced and detected, as described above. Alternatively, the labeled probe may comprise a fluorophore or fluorophore and quencher moieties. A molecular beacon is one embodiment of such a labeled probe that may be used in a homogeneous detection system.

Kits for Detecting CHIKV Nucleic Acids

The present invention also embraces kits for performing polynucleotide amplification reactions using viral nucleic acid templates. Certain preferred kits will contain a hybridization assay probe that includes a target-complementary sequence of bases, and optionally including primers or other ancillary oligonucleotides for amplifying the target that is to be detected. Other preferred kits will contain a pair of oligonucleotide primers that may be used for amplifying target nucleic acids in an in vitro amplification reaction. Exemplary kits include first and second amplification oligonucleotides that are complementary to opposite strands of a CHIKV nucleic acid sequence that is to be amplified. The kits may further contain one or more oligonucleotide detection probes. Still other kits in accordance with the invention may additionally include capture oligonucleotides for purifying CHIKV template nucleic acids away from other species prior to amplification.

The general principles of the present invention may be more fully appreciated by reference to the following non-limiting Examples.

Preferred primer and probe combinations for amplifying and detecting CHIKV nucleic acids were identified in a series of procedures that employed a viral lysate as the source of nucleic acid templates. The lysate was obtained from the Centers for Disease Control, National Center for Infectious Disease, Division of Vector-Borne Infectious Disease, and represented a strain isolated from a traveler returning to the U.S. from a trip to India in 2006. The titer of the virus stock from which the lysate had been prepared was estimated to be $10^6$ plaque forming units (PFU)/ml. A dilution series ranging from 0-10 PFU/ml was prepared and used in the procedure. The number of copies of the viral RNA was originally estimated to be about 200 copies/PFU. Promoter-primers and opposite strand primers were screened in combination using the method described below. Although these procedures were particularly carried out using a Transcription Mediated Amplification (TMA) protocol, the primers disclosed herein may be used to produce amplicons by alternative in vitro nucleic acid amplification methods that will be familiar to those having an ordinary level of skill in the art.

Example 1 describes methods that identified primers and probes useful for amplifying and detecting the CHIKV nucleic acid.

EXAMPLE 1

Amplification of CHIKV Nucleic Acids

A high-titer viral lysate served as the source of CHIKV template sequences in amplification reactions that employed opposed sets of primers. Virus-negative buffer was used to prepare a dilution series corresponding to nucleic acid equivalent to 0-10 PFU/ml. Nucleic acids underwent specimen processing and target capture prior to amplification essentially according to the procedures disclosed in published International Patent Application No. PCT/US2000/18685, except that templates were captured using a CHIKV target capture oligonucleotide having the sequence given hereinabove. Notably, capture oligonucleotides do not participate in the amplification or detection steps of the assay. Virus-containing samples having volumes of 0.5 ml were combined with a target-capture reagent to facilitate nucleic acid release and hybridization to capture oligonucleotides disposed on magnetic beads. TMA reactions were carried out essentially as described by Kacian et al., in U.S. Pat. No. 5,399,491, the disclosure of this U.S. patent having been incorporated by reference hereinabove. Amplification reactions were conducted for various primer combinations using about 10 pmoles of each primer in 100 µl of reaction buffer. Isolated target nucleic acids were combined with primers in a standard nucleic acid amplification buffer, heated to 60° C. for 10 minutes and then cooled to 42° C. to facilitate primer annealing. Moloney Murine Leukemia Virus (MMLV) reverse transcriptase (5,600 units/reaction) and T7 RNA polymerase (3,500 units/reaction) were then added to the mixtures. Amplification reactions were carried out in a Tris-buffered solution (pH 8.2 to 8.5) containing KCl, deoxyribonucleoside 5'-triphosphates, ribonucleoside 5'-triphosphates, N-Acetyl-L-Cysteine, and 5% (w/v) glycerol, as will be familiar to those having an ordinary level of skill in the art.

After a one hour incubation at 42° C., the entire 100 µl amplification reaction was subjected to a hybridization assay employing probes prepared using 2'-Ome nucleotide analogs. All probes were labeled with acridinium ester to specific activities of roughly $2 \times 10^8$ RLU/pmol and then used in amounts equivalent to about $5 \times 10^6$ RLU for each probe in the hybridization reaction. Probes were each labeled with an AE moiety joined to the oligonucleotide structure by an internally disposed non-nucleotide linker according to procedures described in U.S. Pat. Nos. 5,585,481 and 5,639,604, the disclosures of these patents are incorporated by reference. Hybridization reactions were followed by addition of an aliquot of 0.15 M sodium tetraborate (pH 8.5), and 1% TRITON X-100 (Union Carbide Corporation; Danbury, Conn.). These mixtures were first incubated at 60° C. for 10 minutes to inactivate the chemiluminescent label linked to unhybridized probe, and cooled briefly to 4° C. prior to reading the hybridization signal. Chemiluminescence due to hybridized probe in each sample was assayed using a LUMISTAR GALAXY luminescence microplate reader (BMG Labtechnologies Inc.; Durham, N.C.) configured for automatic injection of 1 mM nitric acid and 0.1% (v/v) hydrogen peroxide, followed by injection of a solution containing 1 N sodium hydroxide. Results for the chemiluminescent reactions were measured in relative light units (RLU). In this procedure, the signal/noise value corresponded to the chemiluminescent signal (measured in RLU) generated by label associated with specifically hybridized probe divided by a background signal measured in the absence of a target nucleic acid. Trials were conducted in triplicate. To be judged as a positive result, either the chemiluminescent signal indicating probe hybridization must have exceeded 50,000 RLU in an assay, or the signal-to-noise ratio (where background noise was measured in a negative amplification control reaction) must have been at least 10. Tables 12-26 present the average signal-to-noise values calculated using positive results only.

Representative results from these procedures are summarized in Tables 12-26.

TABLE 12

Amplification and Detection System 1

| T7 Primer(s) | non-T7 Primer(s) | Probe(s) | Viral Dilution | Hybridization Signal (Avg. RLU) | Signal/ Noise (Avg.) |
|---|---|---|---|---|---|
| SEQ ID NO: 111 | SEQ ID NO: 131 | SEQ ID NO: 150 | 0 | 20,362 | 1.0 |
| | | | 0.01 | 3,915,625 | 192.3 |
| | SEQ ID NO: 132 | SEQ ID NO: 151 | 0.1 | 4,023,451 | 197.6 |
| | | | 1.0 | 4,038,800 | 198.4 |
| | | | 10 | 3,976,538 | 195.3 |

TABLE 13

Amplification and Detection System 2

| T7 Primer(s) | non-T7 Primer(s) | Probe(s) | Viral Dilution | Hybridization Signal (Avg. RLU) | Signal/ Noise (Avg.) |
|---|---|---|---|---|---|
| SEQ ID NO: 112 | SEQ ID NO: 133 | SEQ ID NO: 152 | 0 | 44,517 | 1.0 |
| | | | 0.01 | 180,781 | 4.1 |
| | | | 0.1 | 423,102 | 9.5 |
| | | | 1.0 | 1,750,995 | 39.3 |
| | | | 10 | 2,265,910 | 50.9 |

TABLE 14

Amplification and Detection System 3

| T7 Primer(s) | non-T7 Primer(s) | Probe(s) | Viral Dilution | Hybridization Signal (Avg. RLU) | Signal/ Noise (Avg.) |
|---|---|---|---|---|---|
| SEQ ID NO: 113 SEQ ID NO: 114 | SEQ ID NO: 134 SEQ ID NO: 135 316974 8078(+)non-T7CHIKV | SEQ ID NO: 153 316975 8111(+)Probe RXLCHIKV (16/17) | 0 | 11,646 | 1.0 |
| | | | 0.01 | 21,244 | 1.8 |
| | | | 0.1 | 71,227 | 6.1 |
| | | | 1.0 | 550,728 | 47.3 |
| | | | 10 | 1,463,678 | 125.7 |

TABLE 15

Amplification and Detection System 4

| T7 Primer(s) | non-T7 Primer(s) | Probe(s) | Viral Dilution | Hybridization Signal (Avg. RLU) | Signal/Noise (Avg.) |
|---|---|---|---|---|---|
| SEQ ID NO: 115 T7-316980 10027(−) T7CHIKV | SEQ ID NO: 136 316979 9986 (+) non-T7 CHIKV | SEQ ID NO: 154 316978 10007(+)Probe RXLCHIKV (8/9) | 0 0.01 0.1 1.0 10 | 2,521 5,115 23,191 282,525 1,600,934 | 1.0 2.0 9.2 112.1 635.0 |

Notably, the hybridization probe used in system 4 included the target-complementary sequence presented in Table 5, and a 3' terminal G residue that was not complementary to the target sequence being detected. The presence of the extraneous base was believed to have no substantial impact on the detection of CHIKV nucleic acids.

TABLE 16

Amplification and Detection System 5

| T7 Primer(s) | non-T7 Primer(s) | Probe(s) | Viral Dilution | Hybridization Signal (Avg. RLU) | Signal/Noise (Avg.) |
|---|---|---|---|---|---|
| SEQ ID NO: 116 T7-317013 9766(−) T7CHIKV | SEQ ID NO: 137 317011 9709 (+) non-T7 | SEQ ID NO: 155 317012 9749(+)Probe RXLCHIKV (11/12) | 0 0.01 0.1 1.0 10 | 2,601 9,513 58,315 484,637 2,193,496 | 1.0 3.7 22.4 186.4 843.4 |

TABLE 17

Amplification and Detection System 6

| T7 Primer(s) | non-T7 Primer(s) | Probe(s) | Viral Dilution | Hybridization Signal (Avg. RLU) | Signal/Noise (Avg.) |
|---|---|---|---|---|---|
| SEQ ID NO: 117 T7-317017 10323(−)T7 CHIKV | SEQ ID NO: 138 317014 10226(+)non-T7 CHIKV | SEQ ID NO: 156 317015 10274(+)CHIKVRXL (8/9) 317016 10274(+)CHIKVRXL (11/12) | 0 0.01 0.1 1.0 10 | 32,799 298,299 6,678,179 13,122,220 14,843,588 | 1.0 9.1 203.6 400.1 452.6 |

TABLE 18

Amplification and Detection System 7

| T7 Primer(s) | non-T7 Primer(s) | Probe(s) | Viral Dilution | Hybridization Signal (Avg. RLU) | Signal/Noise (Avg.) |
|---|---|---|---|---|---|
| SEQ ID NO: 118 T7-317086 (−)728-747T7 CHIKV | SEQ ID NO: 139 317087 (+) 680-689non-T7 CHIKV | SEQ ID NO: 157 317088 (+)710-727Probe CHIKV(9/10) 317089 (+)710-727Probe CHIKV(8/9) 317090 (+)710-727Probe CHIKV(11/12) | 0 0.01 0.1 1.0 10 | 10,209 18,237 11,483 23,355 127,130 | 1.0 1.8 1.1 2.3 12.5 |

TABLE 19

Amplification and Detection System 8

| T7 Primer(s) | non-T7 Primer(s) | Probe(s) | Viral Dilution | Hybridization Signal (Avg. RLU) | Signal/ Noise (Avg.) |
|---|---|---|---|---|---|
| SEQ ID NO: 119 T7-317091 (−)419-441T7 CHIKV | SEQ ID NO: 140 317092 (+)380-398non-T7 CHIKV | SEQ ID NO: 158 317093 (+)400-417 Probe(7/8) CHIKV | 0 0.01 0.1 1.0 10 | 3,321 3,346 5,217 8,931 91,915 | 1.0 1.0 1.6 2.7 27.7 |
| CHIKV | | 317094 (+)400-417 Probe(8/9) CHIKV | | | |

TABLE 20

Amplification and Detection System 9

| T7 Primer(s) | non-T7 Primer(s) | Probe(s) | Viral Dilution | Hybridization Signal (Avg. RLU) | Signal/Noise (Avg.) |
|---|---|---|---|---|---|
| SEQ ID NO: 120 T7-317095 (−)978-997T7 CHIKV SEQ ID NO: 121 T7-317096 (−)984-1008T7 CHIKV | SEQ ID NO: 141 317097 (+)891-908non-T7 CHIKV | SEQ ID NO: 159 317098 (+)935-952Probe CHIKV(9/10) 317099 (+)935-952Probe CHIKV(6/7) | 0 0.01 0.1 1.0 10 | 15,256 15,912 81,154 401,012 3,322,419 | 1.0 1.0 5.3 26.3 217.8 |

TABLE 21

Amplification and Detection System 10

| T7 Primer(s) | non-T7 Primer(s) | Probe(s) | Viral Dilution | Hybridization Signal (Avg. RLU) | Signal/Noise (Avg.) |
|---|---|---|---|---|---|
| SEQ ID NO: 122 T7-317108 (−)1079-1100T7 CHIKV SEQ ID NO: 123 T7-317109 (−)1089-1115T7 CHIKV | SEQ ID NO: 142 317105 (+)985-1007non-T7 CHIKV | SEQ ID NO: 160 317106 (+)1034-1055Probe CHIKV(12/13) 317107 (+)1034-1055Probe CHIKV(10/11) | 0 0.01 0.1 1.0 10 | 14,846 12,066 80,489 602,205 2,623,790 | 1.0 0.8 5.4 40.6 176.7 |

TABLE 22

Amplification and Detection System 11

| T7 Primer(s) | non-T7 Primer(s) | Probe(s) | Viral Dilution | Hybridization Signal (Avg. RLU) | Signal/Noise (Avg.) |
|---|---|---|---|---|---|
| SEQ ID NO: 124 T7-317113 (−)1136-1156T7 CHIKV SEQ ID NO: 125 T7-317114 (−)1135- | SEQ ID NO: 143 317110 (+)1034-1055non-T7 CHIKV SEQ ID NO: 144 317111 (+)1057- | SEQ ID NO: 161 317112 (+)1089-1107 ProbeCHIKV (8/9) | 0 0.01 0.1 1.0 10 | 68,068 74,078 81,004 65,064 60,146 | 1.0 1.1 1.2 1.0 0.9 |

TABLE 22-continued

Amplification and Detection System 11

| T7 Primer(s) | non-T7 Primer(s) | Probe(s) | Viral Dilution | Hybridization Signal (Avg. RLU) | Signal/Noise (Avg.) |
|---|---|---|---|---|---|
| 1157T7 CHIKV | 1074non-T7 CHIKV | | | | |

TABLE 23

Amplification and Detection System 12

| T7 Primer(s) | non-T7 Primer(s) | Probe(s) | Viral Dilution | Hybridization Signal (Avg. RLU) | Signal/Noise (Avg.) |
|---|---|---|---|---|---|
| SEQ ID NO: 126 T7-317115 (−)6307-6330T7 CHIKV | SEQ ID NO: 145 317116 (+)6254-6273non-T7 CHIKV SEQ ID NO: 146 317117 (+)6260-6282non-T7 CHIKV | SEQ ID NO: 162 317118 (+)6286-6304 ProbeCHIKV (9/10) | 0 0.01 0.1 1.0 10 | 3,234 6,988,910 7,268,005 7,043,396 6,951,975 | 1.0 2161.1 2247.4 2177.9 2149.7 |

TABLE 24

Amplification and Detection System 13

| T7 Primer(s) | non-T7 Primer(s) | Probe(s) | Viral Dilution | Hybridization Signal (Avg. RLU) | Signal/Noise (Avg.) |
|---|---|---|---|---|---|
| SEQ ID NO: 127 T7-317177 | SEQ ID NO: 147 317178 (+)1325- | SEQ ID NO: 163 317179 (+)1351- | 0 0.01 0.1 1.0 | 4,225 4,712 5,525 29,940 | 1.0 1.1 1.3 7.1 |
| (−)1370-1395T7 CHIKV | 1341non-T7CHIKV | 1368Probe (7/8)CHIKV | 10 | 78,911 | 18.7 |

TABLE 25

Amplification and Detection System 14

| T7 Primer(s) | non-T7 Primer(s) | Probe(s) | Viral Dilution | Hybridization Signal (Avg. RLU) | Signal/Noise (Avg.) |
|---|---|---|---|---|---|
| SEQ ID NO: 128 T7-317155 (−)2652-2679T7 CHIV SEQ ID NO: 129 T7-317156 (−)2620-2638T7 CHIKV | SEQ ID NO: 148 317157 (+)2533-2551non-T7 CHIKV | SEQ ID NO: 164 317158 (+)2580-2599Probe CHIKV(7/8) | 0 0.01 0.1 1.0 10 | 5,272 439,688 2,601,933 3,170,773 3,250,318 | 1.0 83.4 493.5 601.4 616.5 |

TABLE 26

Amplification and Detection System 15

| T7 Primer(s) | non-T7 Primer(s) | Probe(s) | Viral Dilution | Hybridization Signal (Avg. RLU) | Signal/Noise (Avg.) |
|---|---|---|---|---|---|
| SEQ ID NO: 130 T7-317160 (−)7496-7522T7 CHIKV | SEQ ID NO: 149 317162 (+)7423-7441non-T7 CHIKV | SEQ ID NO: 165 317163 (+)7457-7476Probe CHIKV(10/11) | 0 0.01 0.1 1.0 10 | 880 5,758 34,335 469,454 1,646,480 | 1.0 6.5 39.0 533.5 1871.0 |

Based on the results appearing in the foregoing tables, certain of the amplification and detection systems (i.e., including opposed primers and probe(s)) yielded better results than others. Particularly preferred amplification and detection systems included: System 1, System 2, System 4, System 5, System 6, System 12, System 14 and System 15. Alternative Assay Designs within Preferred Domains for Amplifying and Detecting CHIKV Nucleic Acids The preceding Example demonstrated numerous different systems that could be used for amplifying and detecting CHIKV nucleic acids with different levels of sensitivity. The following Example illustrates flexibility in the design of individual assays using the target region amplified by System 14 for demonstration purposes.

Generally speaking, certain preferred amplification assays employ paired sets of amplification oligonucleotides arranged such that the extension product of one of the oligonucleotides, using as a template an in vitro synthesized transcript having one of the CHIKV sequences presented in either Table 1 or Table 2, was capable of hybridizing to the other primer. Thus, the two amplification oligonucleotides were complementary to opposite strands of the CHIKV target nucleic acid to be amplified. Products of the amplification reaction include nucleic acid strands up to the lengths of the sequences presented in either Table 1 or Table 2, and having sequences able to hybridize to nucleic acid target sequences consisting of or contained within one of the sequences, or complements thereof, presented in Table 2. Preferred hybridization conditions include those described herein. Whether or not a particular amplicon is capable of this hybridization can easily be established by one of ordinary skill in the art.

As indicated above, the different oligonucleotide sequences presented herein can serve multiple purposes. For example, the probe sequences presented in Table 10 (allowing for RNA and DNA equivalent bases) can serve as primers, and can, for example, be used in combination with the primers presented in Table 8, or primers having the target-complementary sequences contained in these sequences (e.g., the sequences presented in Table 7). To illustrate, the sequence of SEQ ID NO:164 System 14 probe (allowing for substitution or RNA and DNA equivalent bases) can be used as an amplification oligonucleotide (i.e., SEQ ID NO:174) in combination with a second oligonucleotide having the target-complementary sequence contained in SEQ ID NO:128 (e.g., SEQ ID NO:108) for amplifying a CHIKV nucleic acid sequence contained within the template sequence of the preferred System 14 domain presented in Table 1. Likewise, complements of the probe sequences presented in Table 10 (allowing for RNA and DNA equivalent bases) can serve as primers, and can, for example, be used in combination with the primers of the corresponding amplification system presented in Table 9. As well, the target-complementary sequences disclosed herein for use as primers can serve as hybridization probes. It is particularly contemplated that, when used as hybridization probes, the oligonucleotide sequence may be shorter than the sequence disclosed herein as an amplification oligonucleotide or primer. For example the CHIKV target-complementary sequence contained in the System 14 amplification oligonucleotide of SEQ ID NO:128, but having a length of at least 17 bases, could serve as a hybridization probe for detecting CHIKV nucleic acids.

Additional oligonucleotides used for amplifying and/or detecting CHIKV nucleic acid sequences are set forth in Tables 27-29.

TABLE 27

Target-Binding Sequence of System 14 Alternative Non-T7 Primers

| Sequence | Identifier |
|---|---|
| GTGCGGCTTCTTCAATATG | SEQ ID NO: 148 317157 (+) 2533-2551 non-T7 CHIKV |
| CTTCAATATGATGCAGATG | SEQ ID NO: 170 319214 (+) 2542-2560 non-T7 CHIKV |
| GATGCAGATGAAAGTCAAC | SEQ ID NO: 171 319217 (+) 2551-2569 non-T7 CHIKV |
| CAGTGCGGCTTCTTCAATA | SEQ ID NO: 172 319216 (+) 2531-2549 non-T7 CHIKV |
| GGCTTCTTCAATATGATGC | SEQ ID NO: 173 319215 (+) 2537-2555 non-T7 CHIKV |
| ACATCTGCACCCAAGTGTAC | SEQ ID NO: 174 319675 (+) 2580-2599 non-T7 CHIKV |
| TGCACCCAAGTGTACCA | SEQ ID NO: 175 319676 (+) 2585-2601 non-T7 CHIKV |
| AACATCTGCACCCAAGT | SEQ ID NO: 176 319677 (+) 2579-2595 non-T7 CHIKV |

TABLE 28

Target-Binding Sequences and Complete T7 Promoter-Primer Sequences for System 14 Alternative T7 Promoter-Primers

| Sequence | | Identifier |
|---|---|---|
| Target-Binding Sequence | GTCACAGGCAGTGTACAC | SEQ ID NO: 109<br>317156<br>(-) 2620-2638 T7 CHIKV |
| | GTGCGCATTTTGCCTTCGTAATGCAACG | SEQ ID NO: 108<br>317155<br>(-) 2652-2679 T7 CHIKV |
| | AGTGCGCATTTTGCCTTCGTAATGCAACG | SEQ ID NO: 177<br>target-comp contained in<br>T7 pp SID: 108 |
| | CCGCCTGGAGATACTTTT | SEQ ID NO: 178<br>318982<br>(-) 2603-2620 T7 CHIKV |
| | ACCGCCTGGAGATACTTTT | SEQ ID NO: 179<br>target-comp contained in<br>T7 pp 318982 |
| | AGACCGCCTGGAGATACTTTT | SEQ ID NO: 180<br>target-comp contained in<br>T7 pp 318982 |
| | GGAGACCGCCTGGAGATACTTTT | SEQ ID NO: 181<br>target-comp contained in<br>T7 pp 318982 |
| Complete T7 Promoter-Primer | aatttaatacgactcactatagggagaGTCACAGGCAGTGTACAC | SEQ ID NO: 129<br>T7-317156 |
| | aatttaatacgactcactatagggagaGTGCGCATTTTGCCTTCGTAATGCAACG | SEQ ID NO: 128<br>T7-317155 |
| | aatttaatacgactcactatagggagaCCGCCTGGAGATACTTTT | SEQ ID NO: 182<br>T7-318982 |

In every case, a primer from Table 28, when contacted with a CHIKV template sequence consisting of SEQ ID NO:14, can be extended by a template-dependent DNA polymerase to create an extension product. That extension product contains a sequence complementary to the primer sequences listed in Table 27, as well as to the probe sequences, which can function as primers, listed in Table 29 (allowing for substitution of RNA and DNA equivalent bases). Referring to the sequence in the preceding table, the target-binding sequence of SEQ ID NO:109 was positioned downstream of the T7 promoter sequence of SEQ ID NO:90 to result in the T7 promoter-primer sequence of SEQ ID NO:129. The target-binding sequence of SEQ ID NO:108 was positioned downstream of the T7 promoter sequence of SEQ ID NO:90 to result in the T7 promoter-primer sequence of SEQ ID NO:128. A fortuitous base in the promoter sequence meant that the promoter-primer included the target-complementary sequence of SEQ ID NO:177. The target-binding sequence of SEQ ID NO:178 was positioned downstream of the T7 promoter sequence of SEQ ID NO:90 to result in the T7 promoter-primer sequence of SEQ ID NO:182. A fortuitous base in the promoter sequence meant that the promoter-primer included the target-complementary sequence of SEQ ID NO:179. Allowing for a single base mismatch, the sequence of SEQ ID NO:182 included the target-complementary sequence of SEQ ID NO:180 (i.e., position 2 of SEQ ID NO:180 is not complementary to the corresponding position in the target sequence of SEQ ID NO:14). Allowing for two base mismatches, the sequence of SEQ ID NO:182 included the target-complementary sequence of SEQ ID NO:181 (i.e., positions 2 and 4 of SEQ ID NO:181 are not complementary to the corresponding positions in the target sequence of SEQ ID NO:14). The invention embraces the use of any of the target-binding sequences, the complete T7 promoter-primer sequences, or CHIKV-complementary sequences contained in the T7 promoter-primers for amplifying and/or detecting CHIKV nucleic acids in a test sample.

TABLE 29

Target-Binding Sequence of System 14 Alternative Probes

| Sequence | Identifier |
|---|---|
| ACAUCUGCACCCAAGUGUAC | SEQ ID NO: 164<br>317158<br>(+) 2580-2599 Probe CHIKV |
| CCUGUGACYGCCAUUGU | SEQ ID NO: 183<br>Consensus for 184/185 |
| CCUGUGACUGCCAUUGU | SEQ ID NO: 184<br>319857<br>(+) 2630-2646 Probe CHIKV_9u (5/6) |
| CCUGUGACCGCCAUUGU | SEQ ID NO: 185<br>319858<br>(+) 2630-2646 Probe CHIKV (5/6) |

Example 2 describes numerous combinations of oligonucleotides that were used for amplifying and then detecting the CHIKV nucleic acid target region of System 14 (i.e., see Table 1). Procedures carried out using either viral lysate or in vitro transcripts synthesized from a linearized plasmid vector that contained the DNA sequence given by SEQ ID NO:14 (with positions 50, 56 and 116 being occupied by T, C and C, respectively) downstream of a phage promoter. The in vitro transcripts were purified and quantified prior to use in amplification reactions. Use of the in vitro transcript in this Example advantageously provided a method for accurately quantifying assay sensitivity by measuring percent reactivity.

EXAMPLE 2

Flexibility in Assay Design

The following procedures demonstrated alternative strategies for amplifying and detecting CHIKV nucleic acid sequences contained in the target region exemplified by SEQ ID NO:14, as indicated above. In all instances, percent reactivity was determined by using the average RLU reading plus three standard deviations of negative control reactions to establish a cutoff. Readings below a value of 2 were scored as negative. Data presented in the tables is based on this cutoff. Signal values in the tables indicate chemiluminescent signal readings.

Table 30 presents results obtained in a procedure conducted essentially as described for System 14 under Example 1, except that the T7 promoter-primers were used separately, rather than in combination. As well, the highest input level of viral lysate tested in the procedure (i.e., 0.01 PFU/ml) corresponded to the lowest input level for the procedure presented in Table 25. These results provided insight into assay sensitivity with respect to the individual T7 promoter-primers. More specifically, the results indicated that the primer identified as SEQ ID NO:128 (i.e., including the CHIKV target-binding sequence of SEQ ID NO:108) was predominantly responsible for efficient amplification at the very low levels of input template tested in this procedure.

TABLE 30

Alternative Amplification and Detection Assays

| T7 Primer(s) | non-T7 Primer(s) | Probe(s) | Viral Dilution (PFU/ml) | Signal (Avg. RLU) | Signal/ Cutoff (Avg.) | % Reactive n = 10 |
|---|---|---|---|---|---|---|
| SEQ ID NO: 128 T7-317155 | SEQ ID NO: 148 | SEQ ID NO: 164 | 0 | 2047 | 1.0 | 0 |
| | | | 0.001 | 50411 | 24.6 | 70 |
| | | | 0.003 | 126121 | 61.6 | 90 |
| | | | 0.01 | 259358 | 126.7 | 50 |
| SEQ ID NO: 129 T7-317156 | SEQ ID NO: 148 | SEQ ID NO: 164 | 0 | 2023 | 1.0 | 0 |
| | | | 0.001 | 2190 | 1.1 | 0 |
| | | | 0.003 | 2197 | 1.1 | 0 |
| | | | 0.01 | 2053 | 1.0 | 0 |

The following procedures were carried out essentially as described under Example 1, except that known amounts of an in vitro synthesized transcript were substituted in place of the viral lysate. The RNA template included the sequence corresponding to the DNA sequence given by SEQ ID NO:14 (as indicated above), and the amplification products were capable of hybridizing to a nucleic acid strand consisting of this sequence under conditions used for carrying out the amplification reactions, or other hybridization conditions disclosed herein. All procedures were carried out using 0.5 ml sample volumes containing the CHIKV template nucleic acid at the indicated concentration. Thus, for example, a reaction carried out using 0.5 ml of a sample made 50 copies/ml of in vitro transcript would have contained 25 copies of the template nucleic acid.

Table 31 presents results obtained using the amplification and detection oligonucleotides of System 14, as presented in Table 25, but substituting the in vitro synthesized CHIKV transcript in place of the viral lysate as the source of amplifiable template. These results established a baseline for comparing sensitivity parameters of alternative amplification and detection formats. Based on statistical analysis of the results, this assay was characterized by a 95% probability of detection at 111 copies/ml, and by a 50% probability of detection at 9 copies/ml of the CHIKV nucleic acid target.

TABLE 31

Alternative Amplification and Detection Assays

| T7 Primer(s) | non-T7 Primer(s) | Probe(s) | Transcript (c/ml) | Signal (Avg. RLU) | Signal/ Cutoff (Avg.) | % Reactive n = 10 |
|---|---|---|---|---|---|---|
| SEQ ID NO: 128 T7-317155 SEQ ID NO: 129 T7-317156 | SEQ ID NO: 148 | SEQ ID NO: 164 | 0 | 3327 | 1.0 | 0 |
| | | | 1 | 15755 | 4.7 | 10 |
| | | | 3 | 87464 | 26.3 | 20 |
| | | | 11 | 72313 | 21.7 | 50 |
| | | | 33 | 383852 | 115.4 | 70 |
| | | | 100 | 699056 | 210.1 | 100 |
| | | | 300 | 1443921 | 434.0 | 100 |

Table 32 presents results from amplification and detection reactions carried out using only one of the two promoter-primers described in the preceding table. As indicated, these results showed that the primer identified by SEQ ID NO:128 was highly active in amplification assays carried out using the CHIKV template nucleic acid at 300 copies/ml, or lower. Based on statistical analysis of the results, this assay was characterized by a 95% probability of detection at 74 copies/ml, and by a 50% probability of detection at 8 copies/ml of the CHIKV nucleic acid target.

TABLE 32

Alternative Amplification and Detection Assays

| T7 Primer(s) | non-T7 Primer(s) | Probe(s) | Transcript (c/ml) | Signal (Avg. RLU) | Signal/ Cutoff (Avg.) | % Reactive n = 10 |
|---|---|---|---|---|---|---|
| SEQ ID NO: 128 T7-317155 | SEQ ID NO: 148 | SEQ ID NO: 164 | 0 | 2274 | 1.0 | 0 |
| | | | 1 | 13146 | 5.8 | 10 |
| | | | 3 | 186620 | 82.1 | 20 |
| | | | 11 | 123135 | 54.1 | 60 |
| | | | 33 | 152563 | 67.1 | 80 |
| | | | 100 | 364455 | 160.3 | 100 |
| | | | 300 | 948858 | 417.3 | 100 |

Table 33 presents results obtained in a procedure essentially as illustrated in the preceding table, but further including an additional T7 promoter-primer in the amplification reaction. The observed fluctuation in the percent reactivity trend was believed due to the very low template levels used in the procedure. The combination of two T7 promoter-primers in this instance was not believed to provide substantial benefits. Based on statistical analysis of the results, this assay was characterized by a 95% probability of detection at 378 copies/ml, and by a 50% probability of detection at 10 copies/ml of the CHIKV nucleic acid target.

TABLE 33

Alternative Amplification and Detection Assays

| T7 Primer(s) | non-T7 Primer(s) | Probe(s) | Transcript (c/ml) | Signal (Avg. RLU) | Signal/ Cutoff (Avg.) | % Reactive n = 10 |
|---|---|---|---|---|---|---|
| SEQ ID NO: 128 T7-317155 | SEQ ID NO: 148 | SEQ ID NO: 164 | 0 | 4979 | 1.0 | 0 |
| | | | 1 | 206679 | 41.5 | 30 |
| | | | 3 | 90931 | 18.3 | 20 |
| | | | 11 | 98436 | 19.8 | 50 |

Table 34 presents results from amplification and detection reactions carried out using only one of the two promoter-primers described in the preceding table. As indicated, these results showed that the T7 promoter-primer of SEQ ID NO:182 was active in the amplification reaction, but in a manner that yielded lower overall signal/noise ratios and somewhat lower assay sensitivity than other assays disclosed herein. Based on statistical analysis of the results, this assay was characterized by a 95% probability of detection at 3334 copies/ml, and by a 50% probability of detection at 302 copies/ml of the CHIKV nucleic acid target.

TABLE 33-continued

Alternative Amplification and Detection Assays

| T7 Primer(s) | non-T7 Primer(s) | Probe(s) | Transcript (c/ml) | Signal (Avg. RLU) | Signal/Cutoff (Avg.) | % Reactive n = 10 |
|---|---|---|---|---|---|---|
| SEQ ID NO:182 318982 | | | 33 | 102073 | 20.5 | 40 |
| | | | 100 | 381275 | 76.6 | 100 |
| | | | 300 | 593699 | 119.2 | 100 |

TABLE 34

Alternative Amplification and Detection Assays

| T7 Primer(s) | non-T7 Primer(s) | Probe(s) | Transcript (c/ml) | Signal (Avg. RLU) | Signal/Cutoff (Avg.) | % Reactive n = 10 |
|---|---|---|---|---|---|---|
| SEQ ID NO: 182 318982 | SEQ ID NO: 148 317157 | SEQ ID NO: 164 317158 | 0 | 2113 | 1.0 | 0 |
| | | | 1 | 1948 | 0.9 | 0 |
| | | | 3 | 1935 | 0.9 | 0 |
| | | | 11 | 3918 | 1.9 | 0 |
| | | | 33 | 53121 | 25.1 | 10 |
| | | | 100 | 65874 | 31.2 | 20 |
| | | | 300 | 33201 | 15.7 | 50 |

Table 35 presents results from amplification and detection reactions carried out using two non-T7 primers in combination with a single T7 promoter-primer. Based on statistical analysis of the results, this assay was characterized by a 95% probability of detection at 52 copies/ml, and by a 50% probability of detection at 7 copies/ml of the CHIKV nucleic acid target.

TABLE 35

Alternative Amplification and Detection Assays

| T7 Primer(s) | non-T7 Primer(s) | Probe(s) | Transcript (c/ml) | Signal (Avg. RLU) | Signal/Cutoff (Avg.) | % Reactive n = 20 |
|---|---|---|---|---|---|---|
| SEQ ID NO: 128 T7-317155 | SEQ ID NO: 148 317157 | SEQ ID NO: 164 317158 SEQ ID NO: 170 319214 | 0 | 1588 | 1.0 | 0 |
| | | | 11 | 310428 | 195.5 | 65 |
| | | | 33 | 430059 | 270.8 | 90 |

Table 36 presents results from amplification and detection reactions carried out using two non-T7 primers in combination with a single T7 promoter-primer. Based on statistical analysis of the results, this assay was characterized by a 95% probability of detection at 90 copies/ml, and by a 50% probability of detection at 16 copies/ml of the CHIKV nucleic acid target.

TABLE 36

Alternative Amplification and Detection Assays

| T7 Primer(s) | non-T7 Primer(s) | Probe(s) | Transcript (c/ml) | Signal (Avg. RLU) | Signal/Cutoff (Avg.) | % Reactive n = 20 |
|---|---|---|---|---|---|---|
| SEQ ID NO: 128 T7-317155 | SEQ ID NO: 148 317157 SEQ ID NO: 171 319217 | SEQ ID NO: 164 317158 | 0 | 1885 | 1.0 | 0 |
| | | | 11 | 312143 | 165.6 | 35 |
| | | | 33 | 681515 | 361.5 | 75 |

Table 37 presents results from amplification and detection reactions carried out using two non-T7 primers in combination with a single T7 promoter-primer. Based on statistical analysis of the results, this assay was characterized by a 95% probability of detection at 160 copies/ml, and by a 50% probability of detection at 11 copies/ml of the CHIKV nucleic acid target.

TABLE 37

Alternative Amplification and Detection Assays

| T7 Primer(s) | non-T7 Primer(s) | Probe(s) | Transcript (c/ml) | Signal (Avg. RLU) | Signal/Cutoff (Avg.) | % Reactive n = 20 |
|---|---|---|---|---|---|---|
| SEQ ID NO: 128 T7-317155 | SEQ ID NO: 148 317157 SEQ ID NO: 172 319216 | SEQ ID NO: 164 317158 | 0 | 1852 | 1.0 | 0 |
| | | | 11 | 394442 | 213.0 | 50 |
| | | | 33 | 602339 | 325.2 | 75 |

Table 38 presents results from highly sensitive amplification and detection reactions. A column showing the number of trials included in the analysis is presented for completeness. Based on statistical analysis of the results, this assay was characterized by a 95% probability of detection at 26 copies/ml, and by a 50% probability of detection at 4 copies/ml of the CHIKV nucleic acid target.

TABLE 38

Alternative Amplification and Detection Assays

| T7 Primer(s) | non-T7 Primer(s) | Probe(s) | Transcript (c/ml) | Signal (Avg. RLU) | Signal/Cutoff (Avg.) | n | % Reactive |
|---|---|---|---|---|---|---|---|
| SEQ ID NO: 128 T7-317155 | SEQ ID NO: 148 317157 SEQ ID NO: 173 319215 | SEQ ID NO: 164 317158 | 0 | 3997 | 1.0 | 3 | 0 |
| | | | 1 | 994275 | 248.8 | 100 | 17 |
| | | | 3 | 1028324 | 257.3 | 100 | 27 |
| | | | 11 | 998699 | 249.9 | 99 | 81 |
| | | | 33 | 1405729 | 351.7 | 100 | 98 |
| | | | 50 | 1482335 | 370.9 | 100 | 99 |
| | | | 75 | 1506457 | 376.9 | 90 | 100 |
| | | | 100 | 1485609 | 371.7 | 50 | 100 |
| | | | 300 | 1521260 | 380.6 | 50 | 100 |

Table 39 presents results from amplification and detection reactions carried out using as the non-T7 primer an oligonucleotide sequence (allowing for RNA and DNA equivalent bases) previously used as a hybridization probe. Success in the procedure confirmed that probe and primer sequences could serve alternative functions. Based on statistical analysis of the results, this assay was characterized by a 95% probability of detection at 88 copies/ml, and by a 50% probability of detection at 11 copies/ml of the CHIKV nucleic acid target.

TABLE 39

Alternative Amplification and Detection Assays

| T7 Primer(s) | non-T7 Primer(s) | Probe(s) | Transcript (c/ml) | Signal (Avg. RLU) | Signal/Cutoff (Avg.) | % Reactive n = 5 * n = 20 ** |
|---|---|---|---|---|---|---|
| SEQ ID NO: 128 T7-317155 | SEQ ID NO: 174 319675 | SEQ ID NO: 184 319857 SEQ ID NO: 185 319858 | 0 | 8523 | 1.0 | 0 * |
| | | | 11 | 6641800 | 779.3 | 50 ** |
| | | | 33 | 7113798 | 834.7 | 80 ** |
| | | | 300 | 6997337 | 821.0 | 100 * |

Table 40 presents results from amplification and detection reactions carried out using as the non-T7 primer an oligonucleotide sequence (allowing for RNA and DNA equivalent bases) that shares substantial sequence identity with an oligonucleotide previously used as a hybridization probe. Based on statistical analysis of the results, this assay was characterized by a 95% probability of detection at 254 copies/ml, and by a 50% probability of detection at 19 copies/ml of the CHIKV nucleic acid target.

TABLE 40

Alternative Amplification and Detection Assays

| T7 Primer(s) | non-T7 Primer(s) | Probe(s) | Transcript (c/ml) | Signal (Avg. RLU) | Signal/Cutoff (Avg.) | % Reactive n = 5 * n = 20 ** |
|---|---|---|---|---|---|---|
| SEQ ID NO: 128 T7-317155 | SEQ ID NO: 175 319676 | SEQ ID NO: 184 SEQ ID NO: 185 319858 | 0 | 6607 | 1.0 | 0 * |
| | | | 11 | 457780 | 69.3 | 40 ** |
| | | | 33 | 1409687 | 213.4 | 60 ** |
| | | | 300 | 3318324 | 502.2 | 100 * |

Table 41 presents results from amplification and detection reactions carried out using as the non-T7 primer an oligonucleotide sequence (allowing for RNA and DNA equivalent bases) that shares substantial sequence identity with an oligonucleotide previously used as a hybridization probe. Based on statistical analysis of the results, this assay was characterized by a 95% probability of detection at 45 copies/ml, and by a 50% probability of detection at 11 copies/ml of the CHIKV nucleic acid target.

TABLE 41

Alternative Amplification and Detection Assays

| T7 Primer(s) | non-T7 Primer(s) | Probe(s) | Transcript (c/ml) | Signal (Avg. RLU) | Signal/Cutoff (Avg.) | % Reactive n = 5 * n = 20 ** |
|---|---|---|---|---|---|---|
| SEQ ID NO: 128 T7-317155 | SEQ ID NO: 176 319677 | SEQ ID NO: 184 319857 SEQ ID NO: 185 319858 | 0 11 33 300 | 4747 6159224 4017942 7490778 | 1.0 1297.5 846.4 1578.0 | 0 * 50 ** 90 ** 100 * |

Table 42 presents results from amplification and detection reactions carried out using as non-T7 primers one oligonucleotide sequence (allowing for RNA and DNA equivalent bases) previously used as a hybridization probe, and a second oligonucleotide that shares substantial sequence identity with an oligonucleotide previously used as a hybridization probe. Based on statistical analysis of the results, this assay was characterized by a 95% probability of detection at 125 copies/ml, and by a 50% probability of detection at 25 copies/ml of the CHIKV nucleic acid target.

T

TABLE 44

Alternative Amplification and Detection Assays

| T7 Primer(s) | non-T7 Primer(s) | Probe(s) | Transcript (c/ml) | Signal (Avg. RLU) | Signal/Cutoff (Avg.) | % Reactive n = 5 * n = 20 ** |
|---|---|---|---|---|---|---|
| SEQ ID NO: 128 T7-317155 | SEQ ID NO: 175 319676 SEQ ID NO: 176 319677 | SEQ ID NO: 184 319857 SEQ ID NO: 185 319858 | 0 11 33 300 | 4384 5039909 6667439 7501912 | 1.0 1149.6 1520.9 1711.2 | 0 * 60 ** 90 ** 100 * |

Example 3 describes an analysis of data obtained for amplification reactions carried out using the viral lysate as the source of templates.

EXAMPLE 3

Quantifying Sensitivities for Different Amplification Systems

Using results from assays carried out using SEQ ID NO:128, SEQ ID NO:129 and SEQ ID NO:148 as amplification oligonucleotides, and using SEQ ID NO:164 as the hybridization detection probe (i.e., oligonucleotides from the original System 14 assay) it was possible to establish the nucleic acid target concentration for the viral lysate. Briefly, this was accomplished by correlating the 95% probabilities of detection for lysate samples (i.e., measured in PFU/ml) and in vitro transcript (i.e., measured in copies/ml). Notably, the in vitro transcript used in this procedure was synthesized using, as source templates, the viral lysate that was used. Accordingly, the sequence of the target in the lysate matched the sequence of the in vitro transcript. By this approach it was possible to estimate that 1 PFU corresponded to approximately 7,000 copies of the CHIKV nucleic acid target.

The original data obtained using viral lysate as the template source for assay screening, the results of these procedures being presented in Tables 12-26, was processed to determine percent reactivity using the same criterion for positive reactivity that was employed in Example 2. Next, regression analysis using the Probit function in SAS® System software (version 9.1.3) (Cary, N.C.) was used to calculate the 95% and 50% detection levels. The following table presents results of this sensitivity analysis for the various assay systems that yielded the results presented in Tables 12-26. Notably, entries are ranked from the group of most sensitive assays downward. Although all of the systems were designed with the objective of creating highly sensitive assays, the results presented in Tables 45 and 46 indicated a surprising range of sensitivities. These tables identify the concentration of CHIKV, in PFU/ml and corresponding copies/ml, required to achieve 95% probability of detection (Table 45), or 50% probability of detection (Table 46). For example, all of Systems 1-2, 5-6, 12 and 14 advantageously required no more than about 0.01 PFU/ml of CHIKV lysate, or no more than about 70 copies/ml of CHIKV target nucleic acid, to achieve a 95% probability of detection. In contrast, System 8 required nearly 7,400 fold more CHIKV target to achieve the same probability of detection. This illustrates that all of the amplification systems were not equivalent.

TABLE 45

Sensitivity of Assays Performed Using Viral Lysates

| System | PFU/ml | copies/ml |
|---|---|---|
| 95% Probability of Detection | | |
| 1 | <0.01 | <70 |
| 2 | <0.01 | <70 |
| 5 | <0.01 | <70 |
| 6 | <0.01 | <70 |
| 12 | <0.01 | <70 |
| 14 | <0.01 | <70 |
| 15 | <0.01 | <70 |
| 3 | 0.02 | 132 |
| 9 | 0.04 | 278 |
| 10 | 0.04 | 278 |
| 13 | 0.40 | 2769 |
| 7 | 1.90 | 13,272 |
| 4 | 1.95 | 13,682 |
| 8 | 73.89 | 517,219 |
| 11 | >10 | >70,000 |
| 50% Probability of Detection | | |
| 1 | <0.01 | <70 |
| 2 | <0.01 | <70 |
| 5 | <0.01 | <70 |
| 6 | <0.01 | <70 |
| 12 | <0.01 | <70 |
| 14 | <0.01 | <70 |
| 15 | <0.01 | <70 |
| 3 | 0.01 | 80 |
| 9 | 0.03 | 222 |
| 10 | 0.03 | 222 |
| 4 | 0.06 | 409 |
| 13 | 0.32 | 2,214 |
| 7 | 1.14 | 7,994 |
| 8 | 1.38 | 9,689 |
| 11 | >10 | >70,000 |

This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A method for detecting a Chikungunya virus (CHIKV) nucleic acid sequence in a test sample, said method comprising the steps of:
   (a) contacting nucleic acids of the test sample with a set of amplification oligonucleotides,
      wherein a first member of said set is up to 100 bases in length and complementary to at least 15 contiguous bases contained within SEQ ID NO:14, and
      wherein a second member of said set is up to 100 bases in length and complementary to at least 15 contiguous bases of an extension product of the first member of said set of amplification oligonucleotides when a polynucleotide consisting of SEQ ID NO:14 is the template in a template-dependent primer extension reaction;
   (b) performing an in vitro nucleic acid amplification reaction using nucleic acids of the test sample as templates together with said set of amplification oligonucleotides, whereby, if said test sample comprises said CHIKV nucleic acid sequence, there is produced an amplification product; and
   (c) detecting any of said amplification product that may have been produced in the in vitro nucleic acid amplification reaction,
      wherein detecting said amplification product in an amount greater than a cutoff value indicates that the CHIKV nucleic acid sequence is present in the test sample, and
      wherein detecting said amplification product in an amount less than the cutoff value indicates that the CHIKV nucleic acid sequence is absent from the test sample.

2. The method of claim 1, wherein the amplification product detected in step (c) is a single-stranded nucleic acid comprising 17 contiguous bases of one member of said set of amplification oligonucleotides and the complement of 17 contiguous bases of the other member of said set of amplification oligonucleotides.

3. The method of claim 1, wherein the first amplification oligonucleotide is up to 55 bases in length, and wherein the second amplification oligonucleotide comprises 19 contiguous bases of SEQ ID NO:68.

4. The method of claim 3, wherein the 3' terminal sequence of the first amplification oligonucleotide is SEQ ID NO:108.

5. The method of claim 3, wherein the second amplification oligonucleotide is selected from the group consisting of SEQ ID NO:148, SEQ ID NO:170, SEQ ID NO:172 and SEQ ID NO:173.

6. The method of claim 3, wherein the detecting step comprises detecting said amplification product using a hybridization probe.

7. The method of claim 6, wherein the hybridization probe is selected from the group consisting of SEQ ID NO:164, SEQ ID NO:184 and SEQ ID NO:185.

8. The method of claim 3, wherein step (c) comprises detecting said amplification product using a hybridization probe, and wherein the probability of detecting said amplification product in the amount greater than the cutoff value is at least 95% when the concentration of the CHIKV nucleic acid sequence in the test sample is in the range of from 26 copies/ml to about 3,400 copies/ml.

9. The method of claim 3, wherein step (c) comprises detecting said amplification product using a hybridization probe, and wherein the probability of detecting said amplification product in the amount greater than the cutoff value is at least 95% when the concentration of the CHIKV nucleic acid sequence in the test sample is in the range of from 26 copies/ml to about 200copies/ml.

10. The method of claim 3, wherein step (c) comprises detecting said amplification product using a hybridization probe, and wherein the probability of detecting said amplification product in the amount greater than the cutoff value is at least 95% only when the concentration of the CHIKV nucleic acid sequence in the test sample is between about 100 copies/ml and 3,400copies/ml.

11. The method of claim 1, wherein the 3' terminal base sequence of first amplification oligonucleotide is SEQ ID NO:108, wherein step (c) comprises detecting said amplification product using a hybridization probe, and wherein the probability of detecting said amplification product in the amount greater than the cutoff value is at least 95% when the concentration of the CHIKV nucleic acid sequence in the test sample is in the range of from 26copies/ml to about 200 copies/ml.

12. The method of claim 11, wherein the first amplification primer comprises a phage T7 promoter sequence located upstream of SEQ ID NO:108.

13. The method of claim 11, wherein the second amplification oligonucleotide comprises either 19 contiguous bases of SEQ ID NO:68, or 17 contiguous bases of SEQ ID NO:84.

14. The method of claim 11, wherein the second amplification oligonucleotide is selected from the group consisting of SEQ ID NO:148, SEQ ID NO:174 and SEQ ID NO:176.

15. The method of claim 11, wherein the hybridization probe is SEQ ID NO:164.

16. The method of claim 11, wherein the hybridization probe is SEQ ID NO:183.

17. The method of claim 1, wherein the first amplification oligonucleotide is up to 55 bases in length, and wherein the second amplification oligonucleotide comprises 17 contiguous bases of SEQ ID NO:84.

18. The method of claim 17, wherein the second amplification oligonucleotide is selected from the group consisting of SEQ ID NO:174, SEQ ID NO:175 and SEQ ID NO:176.

19. The method of claim 1, wherein the second member of said set of amplification oligonucleotides comprises 17-20 contiguous bases contained within the sequence of SEQ ID NO:186.

20. The method of claim 19, wherein the second member of said set of amplification oligonucleotides is selected from the group consisting of SEQ ID NO:148, SEQ ID NO:170, SEQ ID NO:171, SEQ ID NO:172, SEQ ID NO:173, SEQ ID NO:174, SEQ ID NO:175and SEQ ID NO:176.

21. The method of claim 1, wherein the first member of said set of amplification oligonucleotides hybridizes to a polynucleotide consisting of SEQ ID NO:14 under stringent conditions of 42° C. when the salt concentration is in the range of 0.6-0.9 M, and wherein the second member of said set of amplification oligonucleotides hybridizes to said extension product under the same stringent conditions.

22. The method of claim 1, wherein the cutoff value is determined by a statistical analysis of results obtained for (i) a plurality of amplification reactions performed using known concentrations of the CHIKV nucleic acid sequence, and (ii) a plurality of negative control amplification reactions performed in the absence of the CHIKV nucleic acid sequence.

23. The method of claim 1, wherein the cutoff value is determined by a statistical analysis using average hybridization signal readings of negative control reactions that do not comprise the CHIKV nucleic acid sequence plus three standard deviations of the negative control reactions that do not comprise the CHIKV nucleic acid sequence.

* * * * *